US010509030B2

(12) United States Patent
Nam et al.

(10) Patent No.: US 10,509,030 B2
(45) Date of Patent: Dec. 17, 2019

(54) ARTIFICIAL CELL MEMBRANE COMPRISING SUPPORTED LIPID BILAYER CONNECTED WITH PROBES HAVING CONTROLLABLE MOBILITY AND METHOD FOR ANALYZING INTERACTION BETWEEN MOLECULES USING THE SAME

(71) Applicants: Seoul National University R&DB Foundation, Seoul (KR); BioNano Health Guard Research Center, Daejeon (KR)

(72) Inventors: Jwa Min Nam, Seoul (KR); Young Kwang Lee, Goyang (KR); Sungi Kim, Seoul (KR); Keunsuk Kim, Seoul (KR)

(73) Assignees: Seoul National University R&DB Foundation, Seoul (KR); BioNano Health Guard Research Center, Daejeon (KR)

( * ) Notice: Subject to any disclaimer, the term of this patent is extended or adjusted under 35 U.S.C. 154(b) by 415 days.

(21) Appl. No.: 15/202,928
(22) Filed: Jul. 6, 2016
(65) Prior Publication Data
US 2017/0115286 A1 Apr. 27, 2017

Related U.S. Application Data

(63) Continuation-in-part of application No. PCT/KR2015/000121, filed on Jan. 6, 2015.

(30) Foreign Application Priority Data

Jan. 6, 2014 (KR) .................. 10-2014-0001466

(51) Int. Cl.
*G01N 33/554* (2006.01)
*G01N 33/553* (2006.01)
(Continued)
(52) U.S. Cl.
CPC ..... *G01N 33/554* (2013.01); *G01N 33/54373* (2013.01); *G01N 33/553* (2013.01); *C12N 5/0697* (2013.01)

(58) Field of Classification Search
None
See application file for complete search history.

(56) References Cited

U.S. PATENT DOCUMENTS

2007/0092558 A1    4/2007  Heavner et al.

FOREIGN PATENT DOCUMENTS

JP    2009/512696 A    3/2009
WO    2007/122259 A1   11/2007

OTHER PUBLICATIONS

Yang et al., "Single Nanoparticle Tracking-Based Detection of Membrane Receptor-Ligand Interactions," Analytical Chemistry, 81(7), pp. 2564-2568, Apr. 1, 2009.
(Continued)

*Primary Examiner* — Rebecca L Martinez
(74) *Attorney, Agent, or Firm* — Seed IP Law Group LLP

(57) ABSTRACT

Disclosed herein are an artificial cell membrane including a supported lipid bilayer (SLB) including a substrate and mobility-decreased metal particles bonded onto the substrate; an analysis device or kit including the artificial cell membrane and examining the interactions between molecules, in which one molecule is bonded to the surface of a mobility-decreased metal particle bonded to the artificial cell membrane and the other molecule is bonded to the surface of a mobility-increased metal particle bonded to a lipid at a low valency; a method of examining the interactions between molecules using the analysis device; a kit for quantitative or qualitative analysis of a target material including the artificial cell membrane by plasmonic scattering measurements; and a multiple analysis kit capable of detecting a plurality of target materials using a plurality of metal particles having different plasmonic scattering wavelengths and/or having mobility on a supported lipid bilayer. According to the artificial cell membrane including a supported lipid bilayer containing metal particles attached thereto, the fluidity of the metal particles on the lipid can be controlled by adjusting the number of ligands bonded to the (Continued)

metal particles. Therefore, target molecules for analyzing the interactions therebetween on two types of metal particles having different fluidity are introduced onto the artificial cell membrane, thereby monitoring the movements of the metal particles through plasmonic scattering so as to analyze the interactions between the target molecules. In this case, multiple analysis of simultaneously detecting and quantifying a plurality of target materials using the artificial cell membrane of the present invention, plasmonic scattering wavelengths, and a plurality of particles having different fluidity can be performed.

19 Claims, 33 Drawing Sheets

Specification includes a Sequence Listing.

(51) Int. Cl.
  *G01N 33/543* (2006.01)
  *C12N 5/071* (2010.01)

(56) References Cited

OTHER PUBLICATIONS

Benkoski et al., "Lateral Mobility of Tethered Vesicle-DNA Assemblies," Journal of Physical Chemistry, 109(19), pp. 9773-9779, Apr. 15, 2005.

Kaufmann et al., "A Detailed Investigation of the Formation Kinetics and Layer Structure of Poly(Ethylene Glycol) Tether Supported Lipid Bilayers," Soft Matter, 5, pp. 2804-2814, Jun. 8, 2009.

Chan et al., "Kinetics of DNA-Mediated Docking Reactions Between Vesicles Tethered to Supported Lipid Bilayers," PNAS 104(48), pp. 18913-18918, Nov. 27, 2007.

Yoshina-Ishii et al., "Controlling Two-Dimensional Tethered Vesicle Motion Using an Electric Field: Interplay of Electrophoresis and Electro-Osmosis," Langmuir 22(5), pp. 2384-2391, Jan. 26, 2006.

Chan et al., "Kinetics of DNA-mediated docking reactions between vesicles tethered to supported lipid bilayers," *PNAS* 104(48):18913-18918, 2007.

Japanese Office Action, dated Aug. 24, 2017, for Japanese Application No. 2016-544842, 13 pages (with machine generated English Translation).

Kaufmann et al., "A detailed investigation of the formation kinetics and layer structure of poly (ethylene glycol) tether supported lipid bilayers," *Soft Matter* 5:2804-2814, 2009.

Mascalchi et al., "Probing the influence of the particle in Single Particle Tracking measurements of lipid diffusion," *Soft Matter* 8:4462-4470, 2012.

Hartman et al., "Supported lipid bilayers as dynamic platforms for tethered particles," *Nanoscale* 7:66-76, 2015.

Lee et al., "Massively Parallel and Highly Quantitative Single-Particle Analysis on Interactions between Nanoparticles on Supported Lipid Bilayer," *J. Am. Chem. Soc.* 136:4081-4088, 2014.

Lee et al., "Dark-Field-Based Observation of Single-Nanoparticle Dynamics on a Supported Lipid Bilayer for In Situ Analysis of Interacting Molecules and Nanoparticles," *ChemPhysChem* 16:77-84, 2015.

FIG. 2A
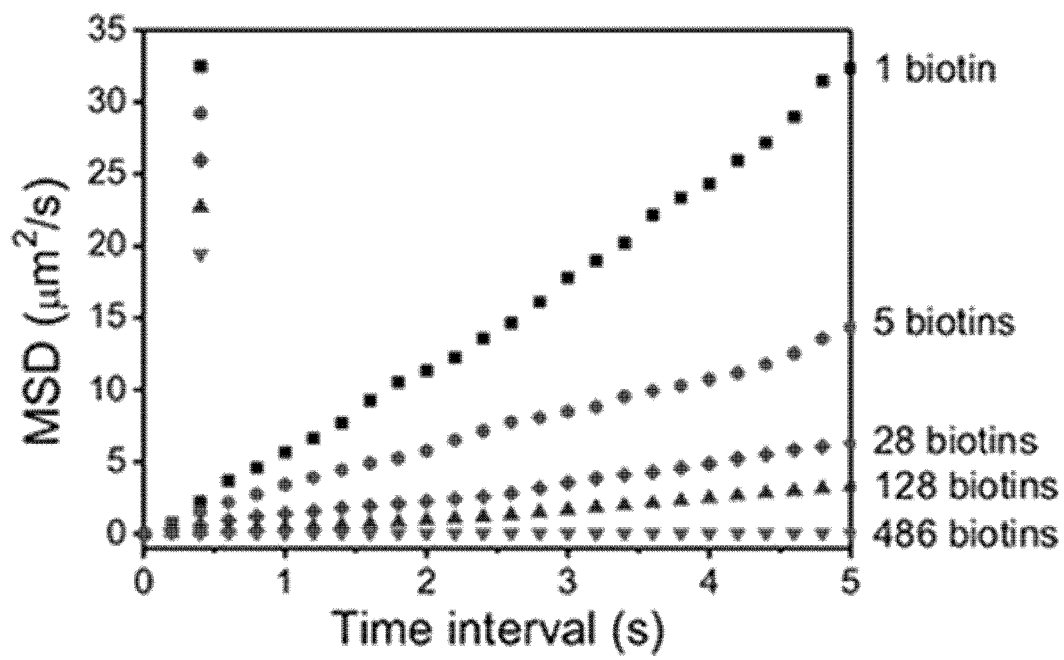
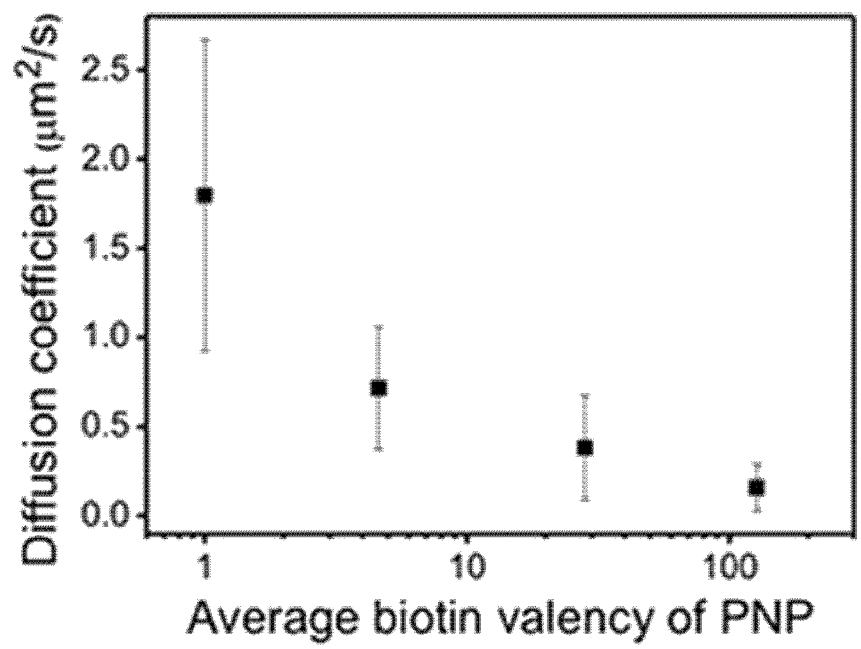
FIG. 2B

FIG. 5A
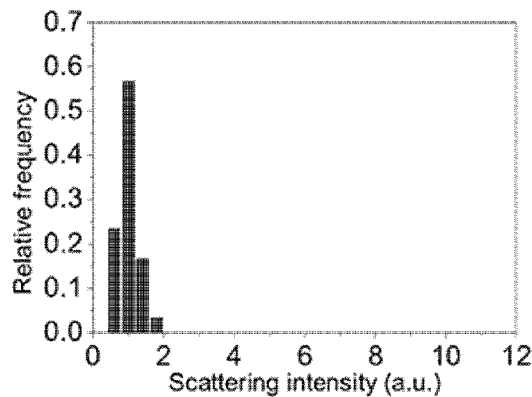
FIG. 5B
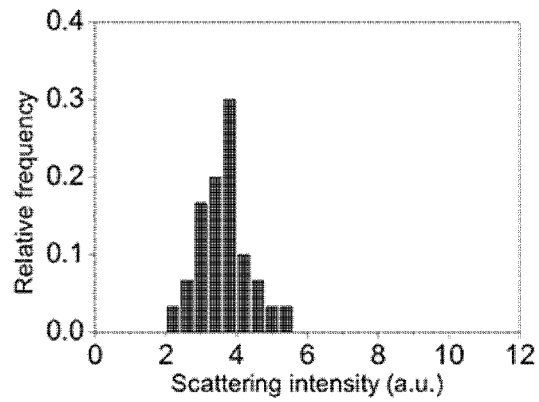
FIG. 5C
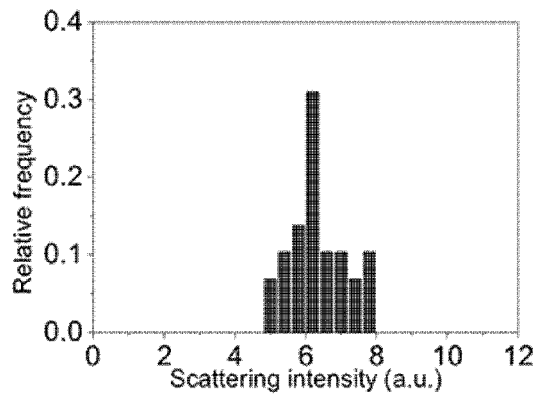
FIG. 5D
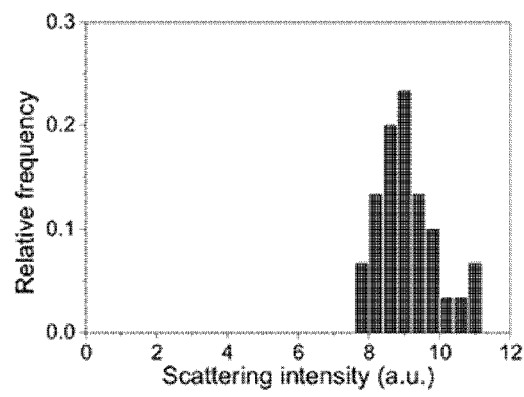
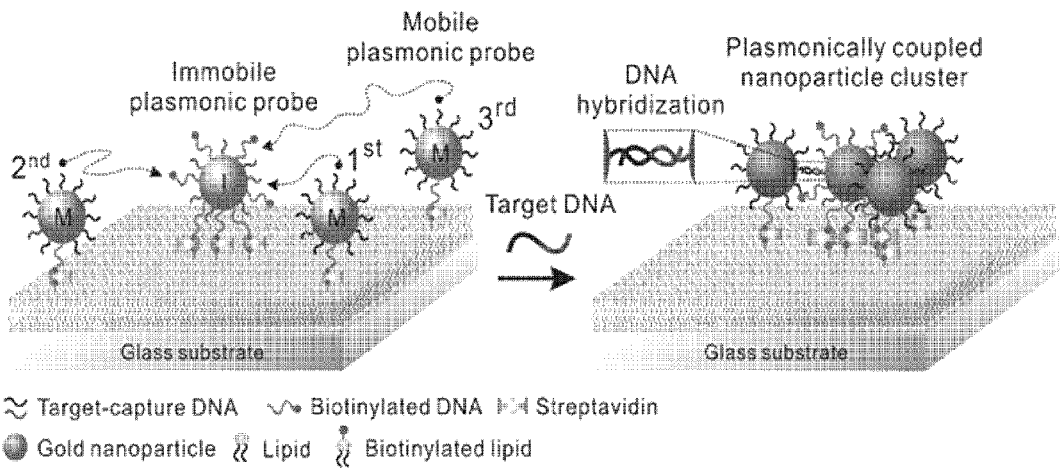
FIG. 6

FIG. 9A
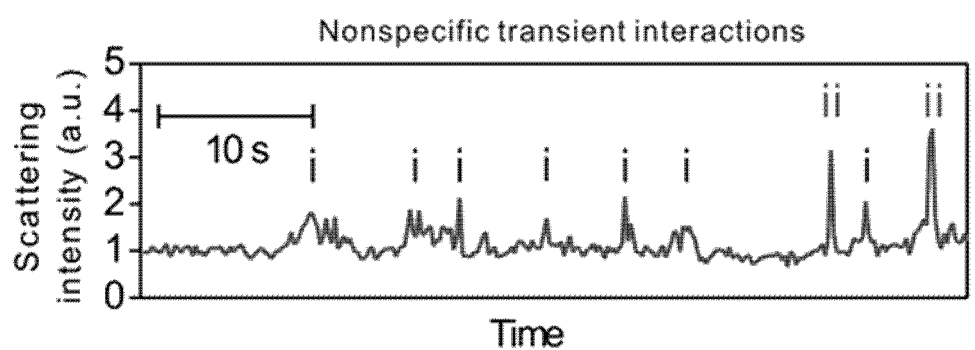
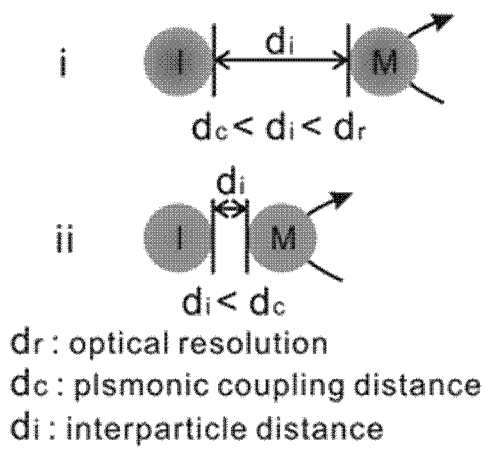
dr : optical resolution
dc : plsmonic coupling distance
di : interparticle distance
FIG. 9B

FIG. 10A
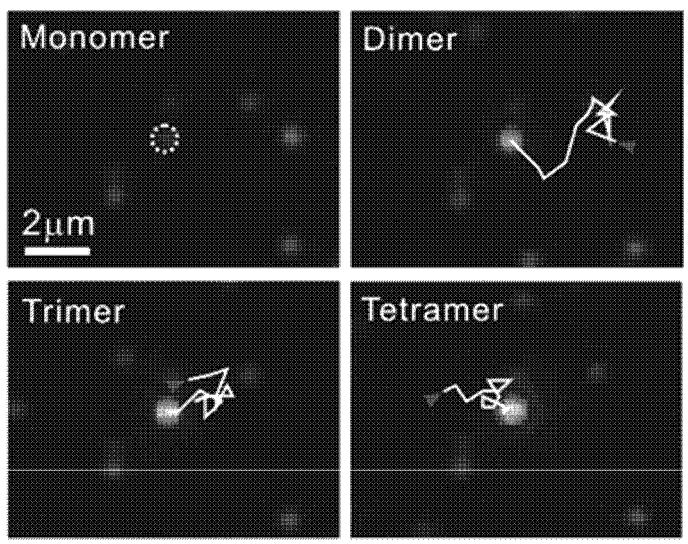
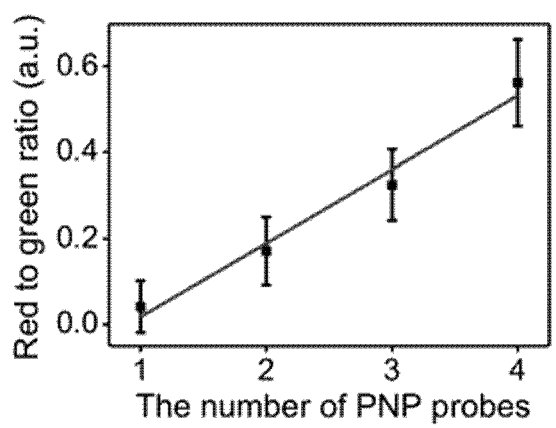
FIG. 10B
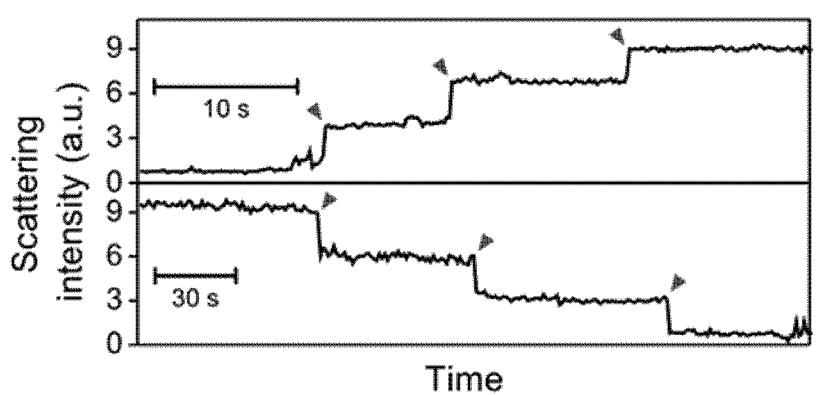
FIG. 10C

FIG. 11A   FIG. 11B   FIG. 11C   FIG. 11D   FIG. 11E
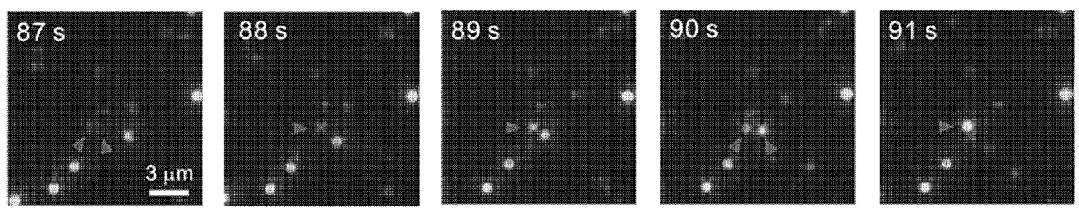
FIG. 12A
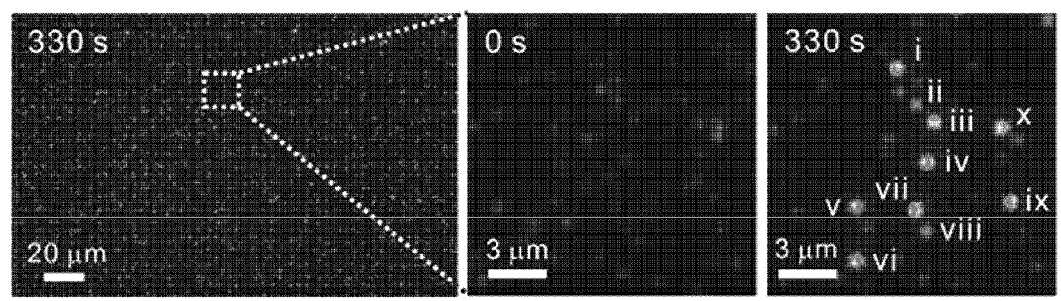
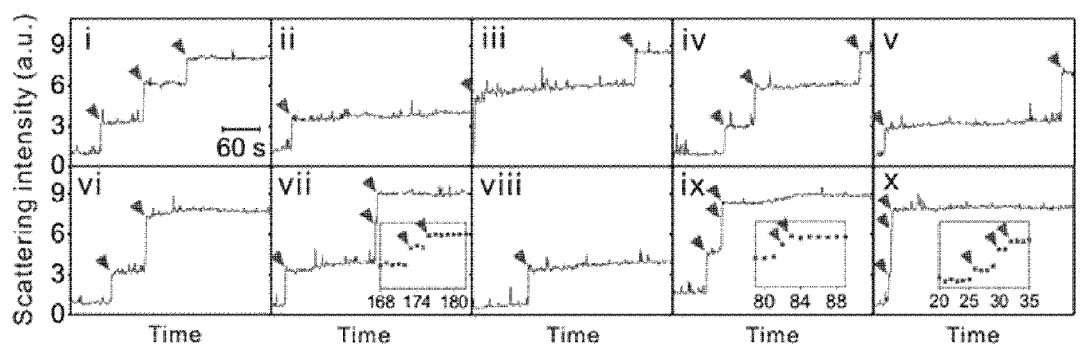
FIG. 12B FIG. 13A
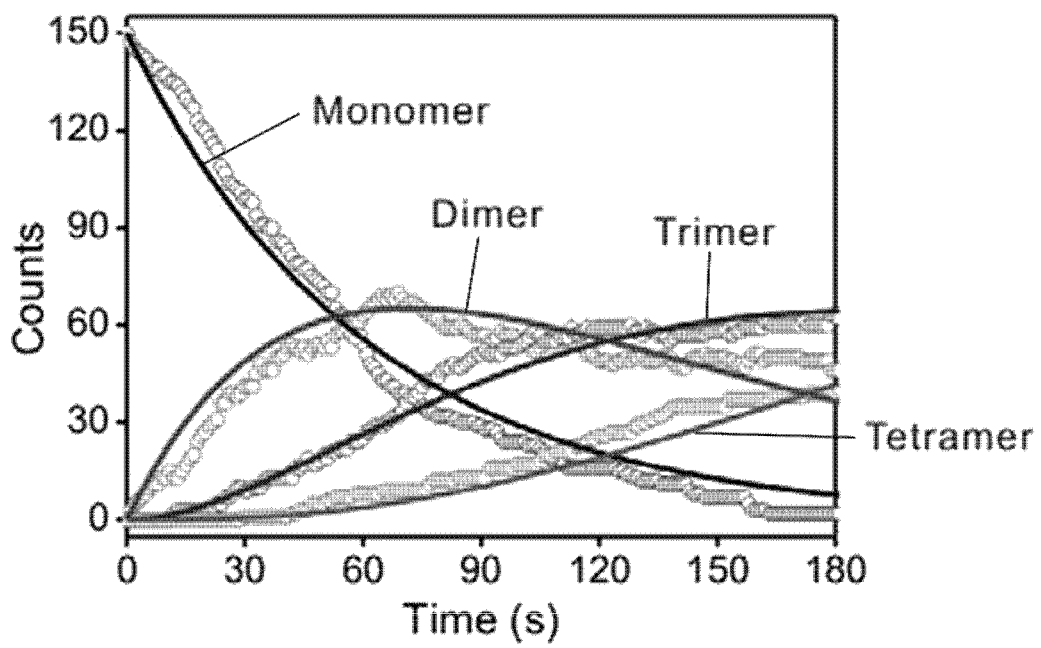
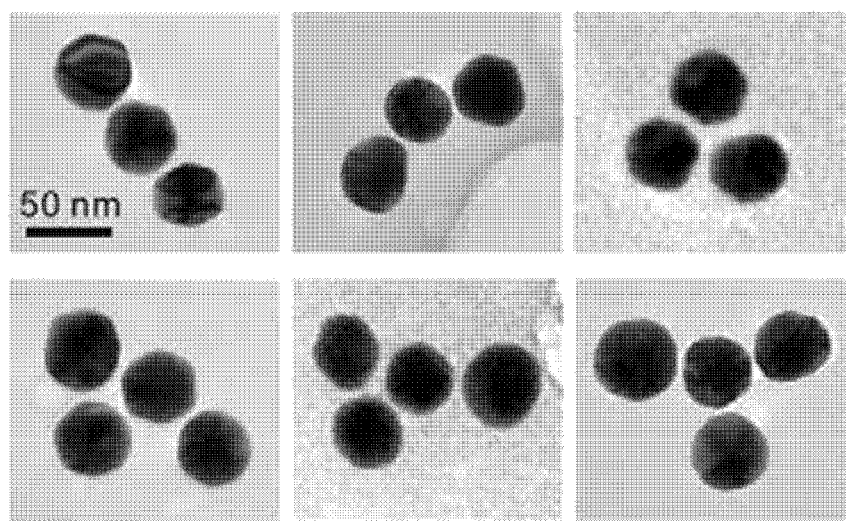
FIG. 13B Trimer formation $f_{dim}=240°/360°$
$=0.6667$ Tetramer formation FIG. 15A
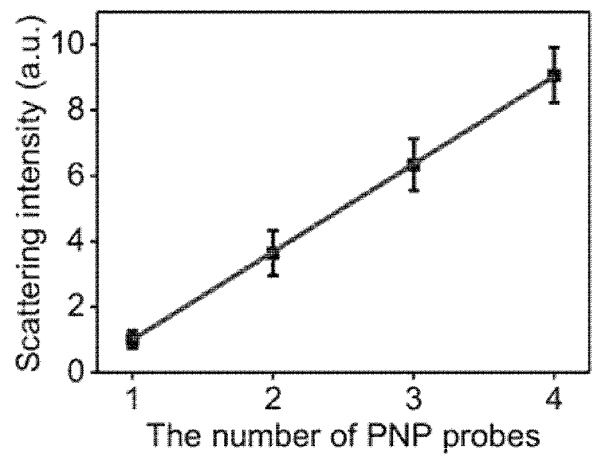
FIG. 15B
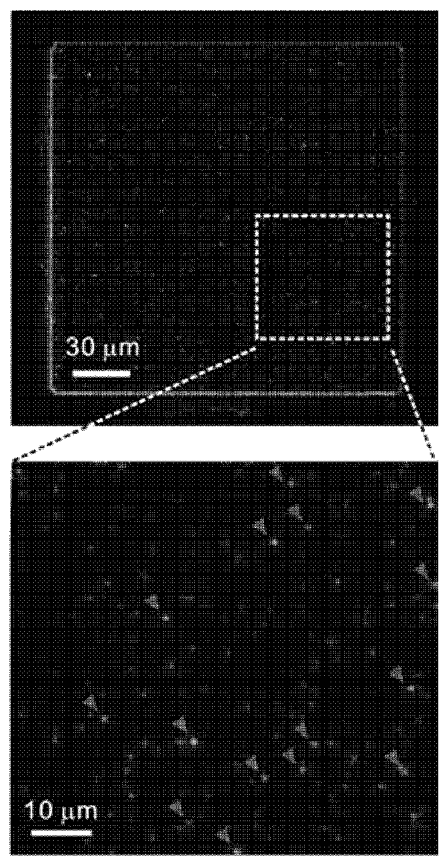
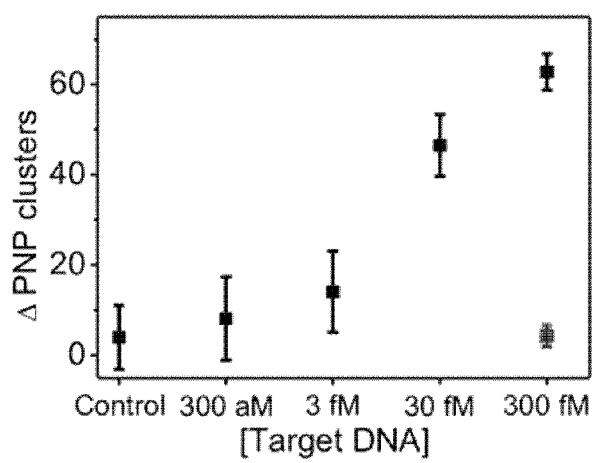
FIG. 15C FIG. 16A
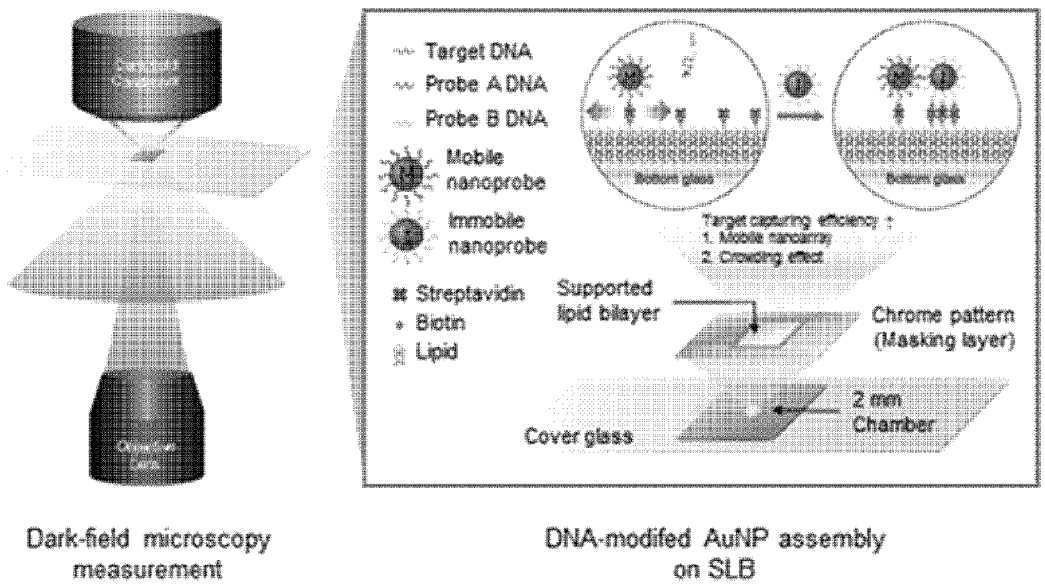
Dark-field microscopy measurement
DNA-modifed AuNP assembly on SLB
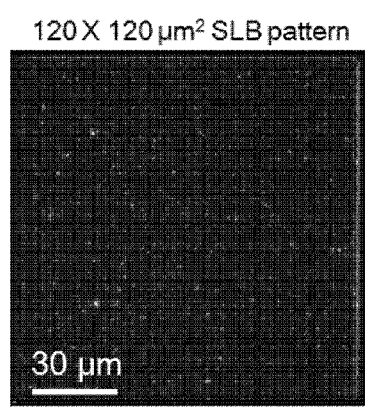
FIG. 16B
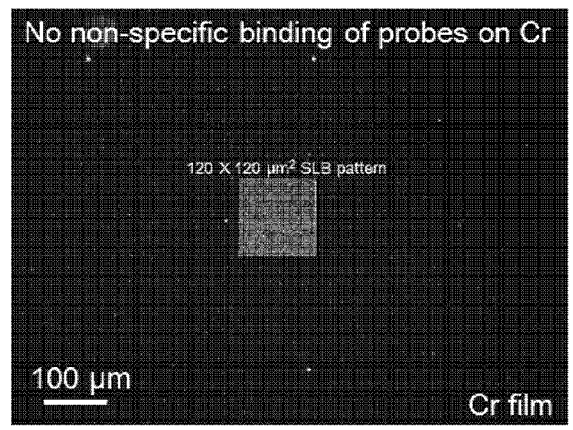
FIG. 16C

FIG. 17A
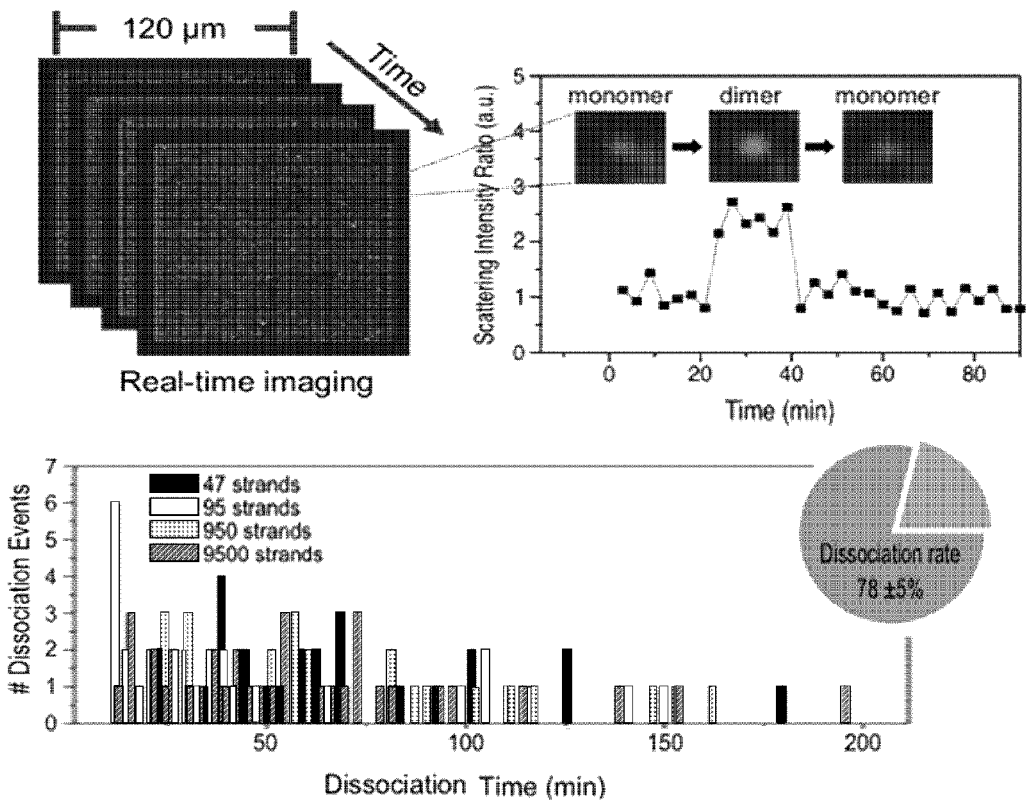
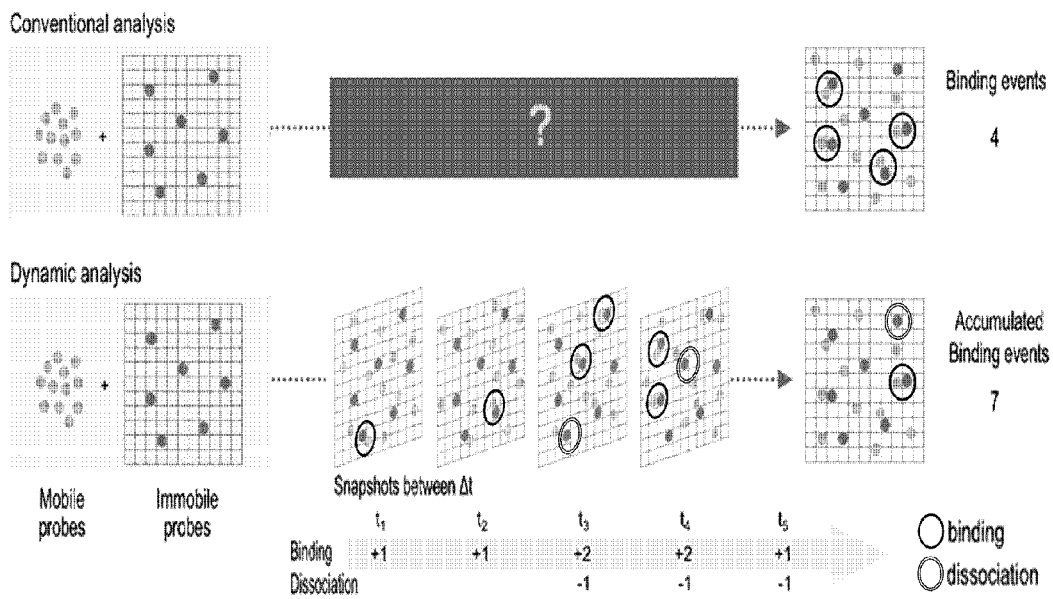
FIG. 17B

FIG. 18A
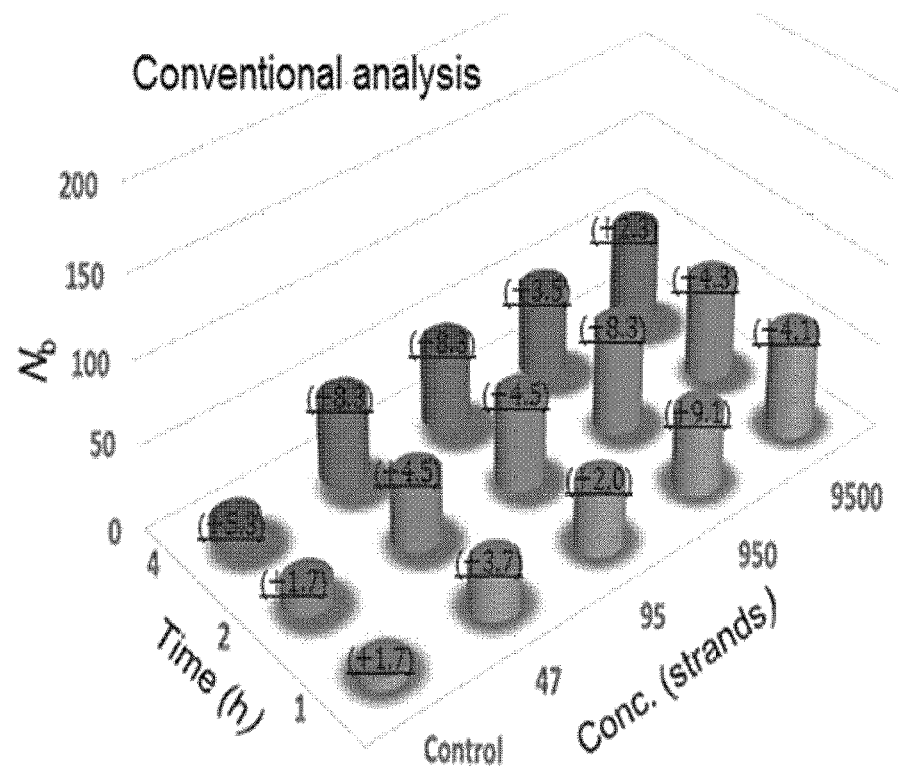
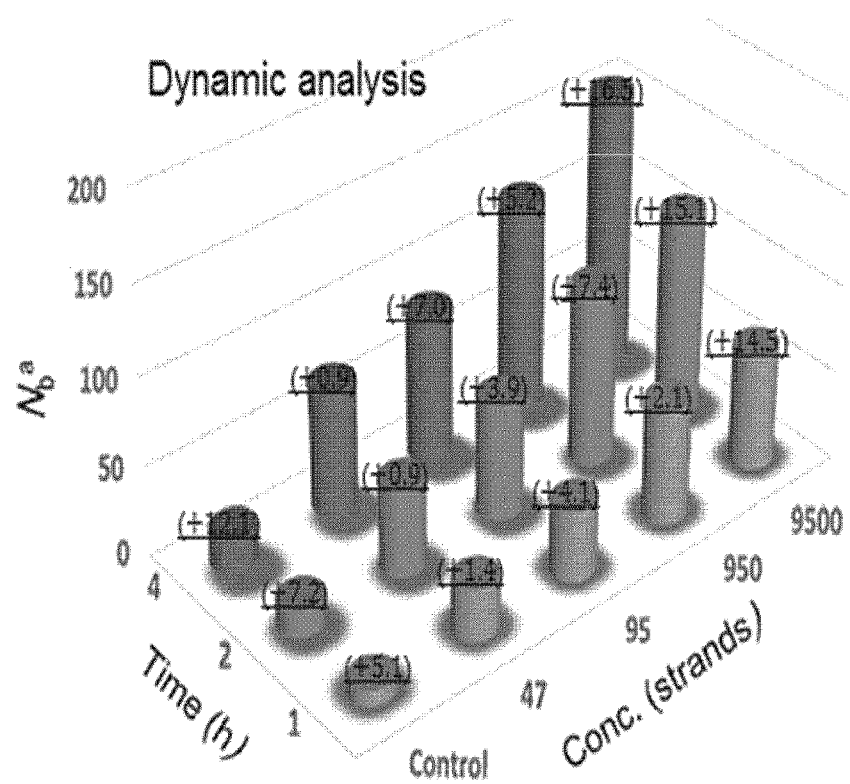
FIG. 18B

FIG. 19A
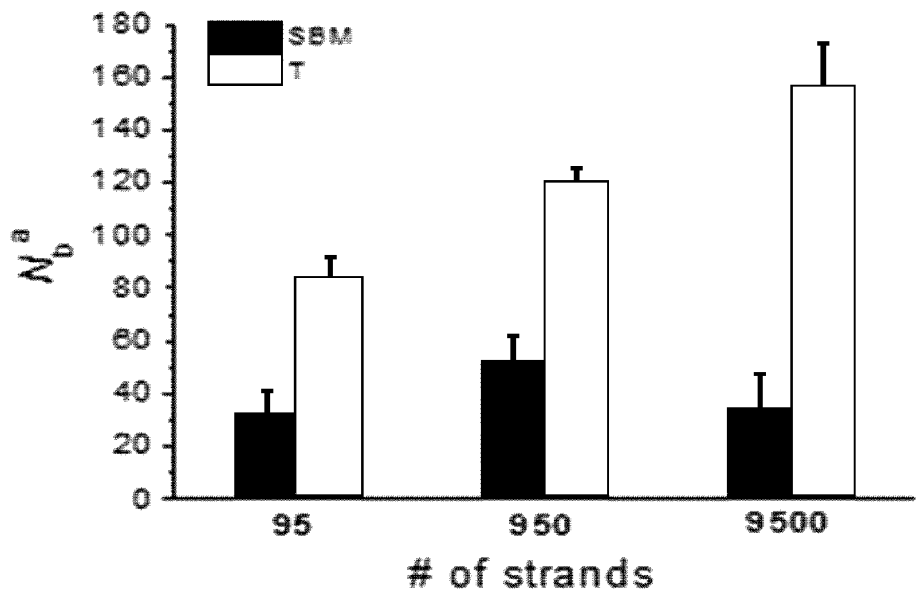
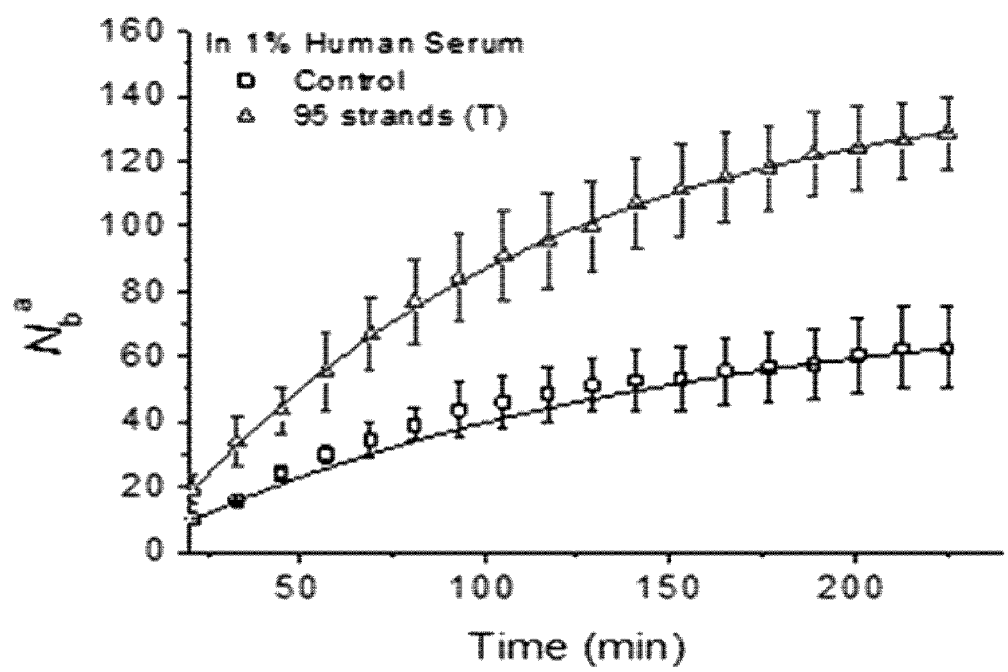
FIG. 19B

FIG. 21A
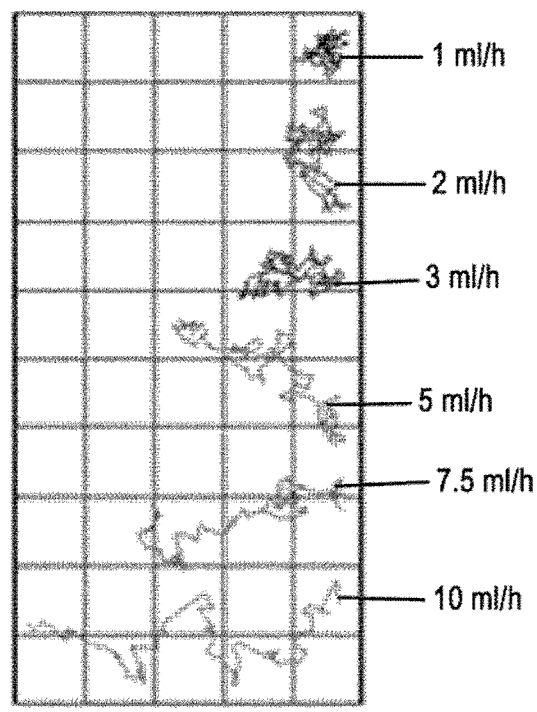
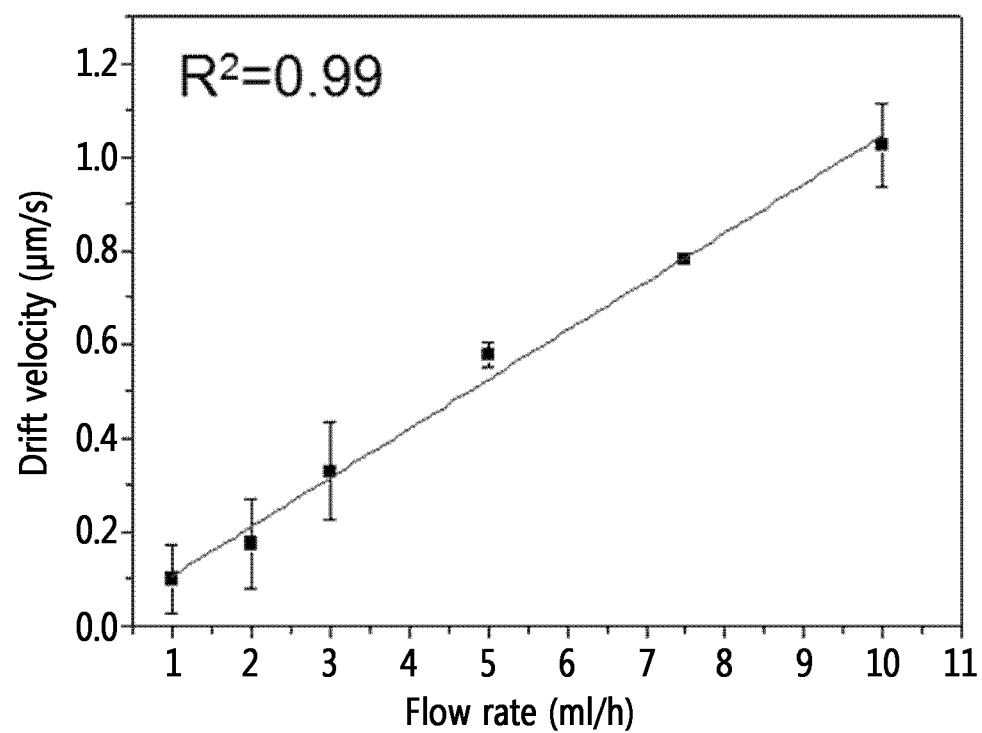
FIG. 21B

FIG. 24A
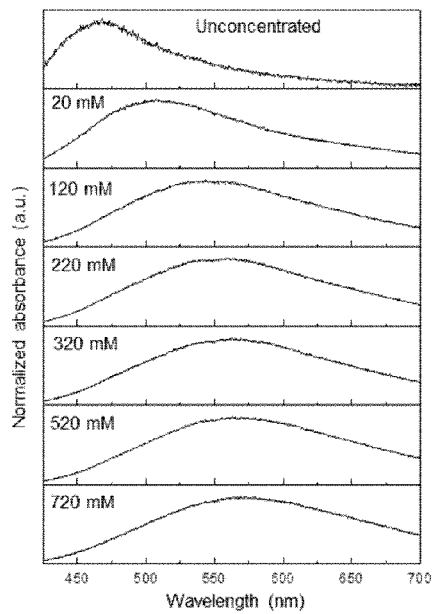
FIG. 24B
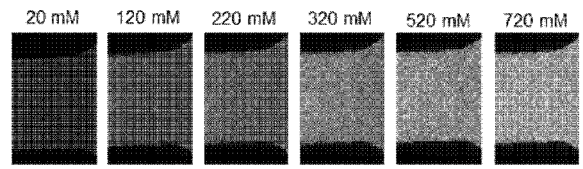
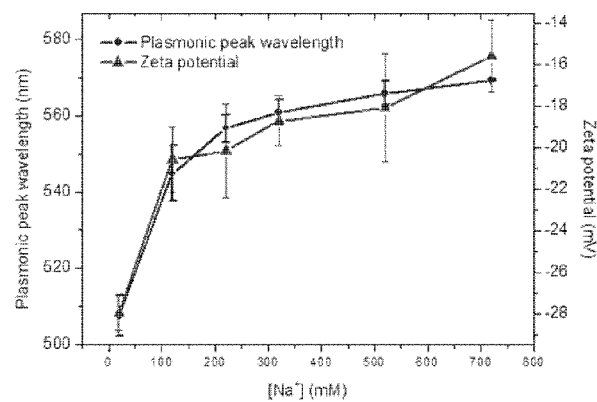
FIG. 24C
FIG. 25
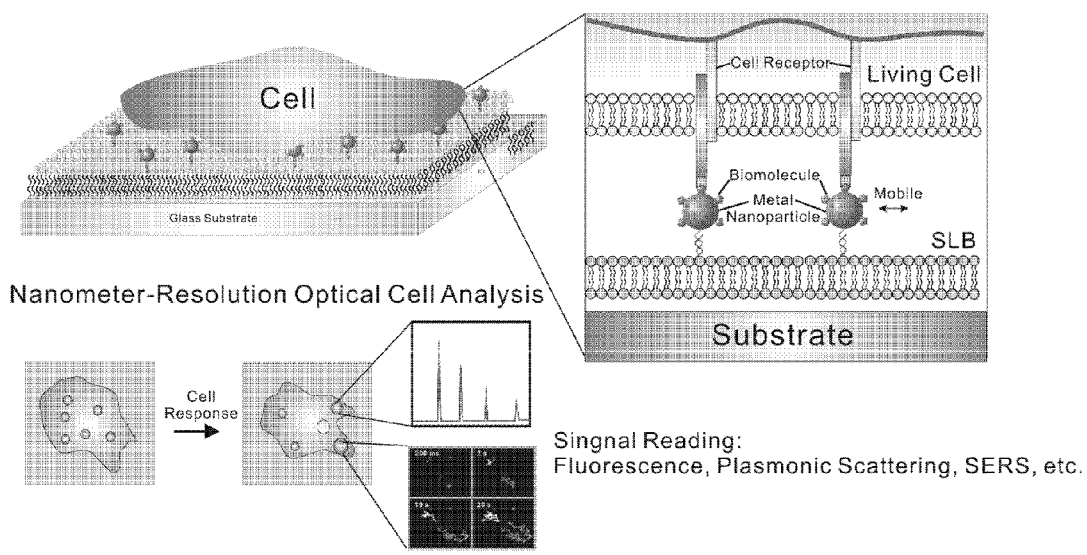

ARTIFICIAL CELL MEMBRANE COMPRISING SUPPORTED LIPID BILAYER CONNECTED WITH PROBES HAVING CONTROLLABLE MOBILITY AND METHOD FOR ANALYZING INTERACTION BETWEEN MOLECULES USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860175_408C1_SEQUENCE_LISTING.txt. The text file is 6.5, was created on Oct. 27, 2016, and is being submitted electronically via EFS-Web.

TECHNICAL FIELD

The present invention relates to an artificial cell membrane including a supported lipid bilayer (SLB) including a substrate and mobility-decreased metal particles bonded onto the substrate; an analysis device or kit including the artificial cell membrane and examining the interactions between molecules, in which one molecule is bonded to the surface of a mobility-decreased metal particle bonded to the artificial cell membrane and the other molecule is bonded to the surface of a mobility-increased metal particle bonded to a lipid at a low valency; a method of examining the interactions between molecules using the analysis device; a kit for quantitative or qualitative analysis of a target material including the artificial cell membrane by plasmonic scattering measurements; and a multiple analysis kit capable of detecting a plurality of target materials using a plurality of metal particles having different plasmonic scattering wavelengths and/or having different mobility on a supported lipid bilayer.

BACKGROUND ART

Single-nanoparticle-resolution in situ measurements provide time-dependent snapshots of the dynamic individual nanoparticles, and thus the heterogeneous interactions between nanoparticles can be elucidated and distinguished from the ensemble. This approach reveals direct and detailed information on colloidal nanocrystal growth and assembly mechanism and reaction kinetics. However, conventional high-resolution imaging methods including electron microscopy typically provide the static information of structures without in situ information and require complicated setup and procedures under harsh conditions (e.g., vacuum). For these reasons, fluorophore-based single-molecule-level optical imaging and analysis methods are mainly used in obtaining the dynamic information on intermolecular interactions, but suffer from the blinking and bleaching problems of fluorophores. Further, discerning short-range molecular interactions of multiple components with fluorophore labels is highly challenging, and even with fluorescence resonance energy transfer, the measurable distance is limited to 10 nm and interpretation becomes difficult for multi-component systems. These are serious issues for real-time studies of the interactions between molecules and nanoparticles and obtaining reproducible and reliable quantitative data for many analyses. Another important issue of these conventional high-resolution optical methods is that dynamically moving objects cannot be individually and reliably analyzed and studied in a solution state because of their uncontrollable three-dimensional movements and the inability of optics to track all of the objects of interest. It should also be noted that, when these objects are fixed on a surface for high-resolution optical analysis, the dynamic behaviors of these objects cannot be studied. For all of these reasons, it would be extremely beneficial to develop a method that allows for in situ imaging and analysis of the interactions between freely moving nanoparticles with single-particle sensitivity. To obtain more reliable information and derive new principles from studying interacting particles, one must also track interactions from multiple reaction sites simultaneously with single-particle-level quantification data.

DISCLOSURE

Technical Problem

Accordingly, the present inventors have studied and endeavored to find methods for observing the interactions between particles on a two-dimensional plane with high resolution while ensuring the free movement of the particles. As a result, they have found that the fluidity of metal particles formed on a supported lipid bilayer (SLB) by streptavidin-biotin bonds can be adjusted by adjusting the biotin valency on the particles, and that the reaction kinetics of the interactions between the particles due to the interaction between DNA strands having complementary sequences formed on the surface of the metal particles can be tracked and analyzed with high resolution at the single-particle level. Based on these findings, the present invention has been completed.

Technical Solution

In order to accomplish the above objects, a first aspect of the present invention provides an artificial cell membrane, comprising: a substrate; and a supported lipid bilayer (SLB) disposed on the substrate, wherein the supported lipid bilayer, within which some or all lipids are capable of shifting position, comprises a first lipid bound with a first ligand, and a first metal particle comprising a second ligand specifically binding to the first ligand at a density of 100 to $100,000/\mu m^2$ is bound to at least two of the first lipids through the binding between the first ligand and the second ligand, so as to decrease the mobility of the first metal particle in the supported lipid layer to 0 to $0.5 \times 10^{-8}$ $cm^2/s$.

A second aspect of the present invention provides an analysis device for examining the interaction between molecule A and molecule B using an artificial cell membrane, comprising: the artificial cell membrane of the first aspect, in which a supported lipid bilayer further comprises a third lipid bound with a third ligand which is the same as or different from the first ligand; the molecule A bound to the surface of the first metal particle in the artificial cell membrane; a second metal particle comprising a fourth ligand specifically binding to the third ligand, wherein the second metal particle binds to at least one of the third lipids through the interaction between the third ligand and the fourth ligand, and has higher mobility compared to that of the first metal particle; and the molecule B bound to the surface of the second metal particle in the artificial cell membrane, wherein the second metal particle having higher mobility approaches the first metal particle and is then confined to the first metal particle by the interaction between the molecule A and the molecule B.

A third aspect of the present invention provides a method of examining the interaction between the molecule A and the molecule B using the analysis device of the second aspect.

A fourth aspect of the present invention provides an analysis kit for determining the binding between molecule A and molecule B by determining the distance between a first metal particle and a second metal particle from plasmonic scattering signals of the first metal particle bound with the molecule A and the second metal particle bound with the molecule B on an artificial cell membrane, comprising: an artificial cell membrane comprising a substrate, a supported lipid bilayer which is disposed on the substrate and within which some or all lipids are capable of shifting position, and a first lipid bound with a first ligand and a third lipid bound with a third ligand, which is the same as or different from the first ligand, as a part of the supported lipid bilayer, a first metal particle comprising a second ligand specifically binding to the first ligand, wherein the first metal particle is able to bind to at least one of the first lipids through the interaction between the first ligand and the second ligand; and a second metal particle comprising a fourth ligand specifically binding to the third ligand, wherein the second metal particle is able to bind to at least one of the third lipids through the interaction between the third ligand and the fourth ligand.

A fifth aspect of the present invention provides a kit for qualitative or quantitative analysis of a target material capable of binding to molecule A and molecule B which is used to determine the binding between the molecule A and the molecule B by determining the distance between a first metal particle and a second metal particle from plasmonic scattering signals of the first metal particle bound with the molecule A and the second metal particle bound with the molecule B on an artificial cell membrane, comprising: an artificial cell membrane comprising a substrate, a supported lipid bilayer which is disposed on the substrate and within which some or all lipids are capable of shifting position, and a first lipid bound with a first ligand and a third lipid bound with a third ligand, which is the same as or different from the first ligand, as a part of the supported lipid bilayer, a first metal particle comprising a second ligand specifically binding to the first ligand, wherein the first metal particle is able to bind to at least one of the first lipids through the interaction between the first ligand and the second ligand; the molecule A which is bound to the surface of the first metal particle and which is specifically bound to a portion of the target material; a second metal particle comprising a fourth ligand specifically binding to the third ligand, wherein the second metal particle is able to bind to at least one of the third lipids through the interaction between the third ligand and the fourth ligand; and the molecule B which is bound to the surface of the second metal particle in the artificial cell membrane and which is specifically bound to another portion of the target material on which the molecule A is not bound.

A sixth aspect of the present invention provides a multiple analysis kit for qualitative or quantitative analysis of target materials in the amount of $i_{max} \times m_{max}$ by the plasmonic scattering measurement ($i_{max}$ and $m_{max}$ are maximum values of the following variables i and m, respectively, and are each independently an integer of 1 or more, but not $i_{max}=m_{max}=1$), comprising: an artificial cell membrane comprising a substrate, a supported lipid bilayer which is disposed on the substrate and within which some or all lipids are capable of shifting positions, and a lipid $I_i$ bound with a ligand $I_i$ and a lipid $M_m$ bound with a ligand $M_m$ (herein, the ligand $I_i$ and the ligand $M_m$ may be the same as or different from each other); a metal particle $I_i$ comprising a ligand $I'_i$ specifically binding to the ligand $I_i$, wherein the metal particle $I_i$ is bound to at least one of the lipids $I_i$ through the interaction between the ligands $I_i$ and the ligand $I'_i$; a molecule $A_i$ which is bound to the surface of the metal particle $I_i$ and is specifically bound to a portion of the target material; a metal particle $M_m$ comprising a ligand $M'_m$ specifically binding to the lipid $M_m$, wherein the metal particle $M_m$ is bound to at least one of the lipids $M_m$ through the interaction between the ligand $M_m$ and the ligand $M'_m$; and a molecule $B_m$ which is bound to the surface of the metal particle $M_m$ in the artificial cell membrane and which is specifically bound to another portion of the target material on which the molecule A is not bound, wherein the series of the metal particles $I_i$ have different plasmonic scattering wavelengths from one another, and the series of the metal particles $M_m$ have different plasmonic scattering wavelengths from one another.

A seventh aspect of the present invention provides a method of concentrating particles into a specific area of a fluid channel, comprising: preparing a supported lipid bilayer in the fluid channel, wherein the supported lipid bilayer comprises a first lipid bound with a first ligand, and some or all lipids are capable of shifting positions in the supported lipid bilayer, applying a first particle comprising a second ligand specifically binding to the first ligand onto the supported lipid bilayer, and transferring the first particles into the specific area of the fluid channel by applying a fluid flow in the fluid channel.

Advantageous Effects

According to the artificial cell membrane including a supported lipid bilayer containing metal particles attached thereto, the fluidity of the metal particles on the lipid can be controlled by adjusting the number of ligands bonded to the metal particles. Therefore, target molecules for analyzing the interactions therebetween on two types of metal particles having different fluidity are introduced onto the artificial cell membrane, thereby monitoring the movements of the metal particles through plasmonic scattering so as to analyze the interactions between the target molecules. In this case, multiple analysis of simultaneously detecting and quantifying a plurality of target materials using the artificial cell membrane of the present invention, plasmonic scattering wavelengths, and a plurality of particles having different fluidity can be performed.

DESCRIPTION OF DRAWINGS

FIGS. 2A and 2B show graphs illustrating the effects of the biotin valency on diffusive dynamics of PNP probes on the SLB. FIG. 2A shows the mean square displacements of PNPs as a function of time interval, and FIG. 2B shows the average diffusion coefficients of plasmonic probes on the SLB.

In FIGS. 3A to 3D, the biotin valencies per probe are 1 in FIG. 3A, 5 in FIG. 3B, 25 in FIG. 3C, and 128 in FIG. 3D.

FIG. 4A shows the dark-field microscope image of I-PNP with a biotin valency of 486 on the STV-coated SLB. FIG. 4B shows the fluorescence microscope image of Cy3-modified STV on the I-PNP-modified SLB. The scale bar is 10 μm.

FIGS. 5A to 5D show the graphs of the scattering intensity distributions of PNP clusters as a function of the clustering degree. FIG. 5A shows the result of a monomer, FIG. 5B shows the result of a dimer, FIG. 5C shows the result of a trimer, and FIG. 5D shows the result of a tetramer.

FIG. 6 is a schematic view illustrating the interactions between nanoparticles dynamically tethered on the SLB. Specifically, FIG. 6 shows the schematic illustration of plasmonic nanoprobe-tethered SLB with two different types of probes (mobile and immobile plasmonic probes; left), and target DNA hybridization-induced two-dimensional duster formation and plasmonic coupling (right).

FIGS. 7A and 7B show the massively parallel in situ observation and analysis of the plasmonic nanoprobe tethered on the SLB using the dark-field microscopy with a single-nanoparticle resolution (scale bar=10 μm), and FIG. 7C shows the dark-field microscope image-based analysis of the scattering intensity and color spectrum of a single plasmonic nanoprobe.

FIG. 8A shows the biotin-valency-based control of nanoparticle mobility (increased valency results in lower mobility), FIG. 8B shows the representative diffusion trajectories of plasmonic nanoparticles, and FIG. 8C shows the mobile fraction of plasmonic nanoparticles as a function of biotin valency.

FIGS. 9A and 9B shows the analysis of nonspecific interactions of particles. FIG. 9A shows the time traces and depicting diagrams of change in the scattering intensity for an immobile plasmonic probe site in the absence of a target DNA sequence, and FIG. 9B shows the schematic diagrams thereof.

FIG. 10A shows the dark-field microscopic images of target DNA hybridization-induced plasmonic nanoparticle clusters. 15-step-trajectories of mobile probes, captured within an immobile probe site (white dashed circle) are highlighted with white solid lines, and red arrows indicate the starting positions of each trajectory. The time interval for each trajectory step is 0.188 s. FIG. 10B shows the red to green ratio plot for the dark-field microscopic images of probe dusters as a function of the number of probes per duster ($R2=0.970$). FIG. 10C shows the representative time traces of the scattering intensity for the assembly (top) and disassembly (bottom) process of nanoparticle clusters.

FIGS. 11A to 11D show photographs illustrating the cluster growth through combination of monomeric PNP attachment and coalescence between PNP clusters in an M-PNP pair-modified SLB. FIG. 11A shows the two monomeric PNPs approaching each other, FIG. 11B shows the distant optical overlapping of two PNP monomers, FIG. 11C shows the DNA hybridization-mediated PNP dimer formation and consequent plasmonic coupling. FIG. 11D shows the PNP dimer and PNP trimer approaching each other, and FIG. 11E shows the coalescence between the PNP dimer and PNP trimer.

FIGS. 12A to 12B show the results of in situ imaging and analysis of plasmonic nanoparticle cluster growth kinetics.

FIG. 12A shows the massively parallel in situ monitoring of DNA hybridization-induced plasmonic coupling of nanoparticle probes in a large SLB surface area. The left image was taken at 330 s after the addition of 30 nM target DNA sequence. The magnified images of the white dashed area before (0 s) and after (330 s) the addition of the target DNA sequence are shown. FIG. 12B shows the time-dependent scattering intensity plots for 10 individual nanoparticle clustering reactions that are shown in the dark-field microscopic image in FIG. 12A. The scattering intensity was normalized to the average intensity of monomeric probes. The signal was recorded every 1 s for 330 s.

FIGS. 13A to 13B show the growth kinetics of plasmonic nanoparticle duster and the images thereof. FIG. 13A shows the reaction kinetics plot of the plasmonic duster growth at 30 nM target DNA sequence (empty circles). Each single probe addition reaction was detected by monitoring the stepwise increase in the scattering intensity of the growing dusters (N=150 particles). The duster formation kinetics were fitted to a three-step consecutive reaction model (solid lines). FIG. 13B shows the transmission electron microscope images of clustered plasmonic nanoprobes.

FIGS. 15A to 15C show the quantitative plasmonic coupling-based DNA detection assay on the SLB. FIG. 15A shows the scattering intensity calibration standards as a function of the number of plasmonic probes in the dusters ($R^2=0.999$). FIG. 15B shows the PNP-modified patterned SLB embedded in a gold film and having an area of 120×120 μm², which was reacted with 300 fM of target DNA for 4 h. FIG. 15C shows the plot of target DNA assay results as a function of DNA concentration (black dots). The assay result for a single-base-mismatched DNA sequence was plotted with a red dot.

FIGS. 16A to 16B show the optimization of an ultralow-concentration target material detection assay. FIG. 16A is a schematic view showing the dark-field microscopy measurement for detecting nanoparticles (left) and the hybridization of target DNA with a mobile nanoprobe and an immobile nanoprobe modified with DNA having a sequence complementary to that of the target DNA on a supported lipid bilayer guided to a chrome pattern on a glass substrate (right). FIG. 16B shows the measurement results of reaction with the target DNA of 45 aM (that is, 95 DNA strands) in the PNP-modified patterned SLB embedded in a chrome film and having an area of 120×120 μm². The left side of FIG. 16B shows the observation result of the PNP-modified patterned SLB embedded in the chrome film, and the right side of FIG. 16B shows the observation result of the PNP-modified patterned SLB surrounded by the chrome film. From the results, it can be found that non-specific binding of PNP probes on the chrome film other than the PNP-modified patterned SLB is not observed.

FIGS. 17A and 17B show a method of analyzing data measured over time according to the present invention. The left upper end of FIG. 17A shows the real-time dark-field microscope image snapshots of nanoprobes on a patterned lipid bilayer, the right upper end of FIG. 17A shows the change in scattering intensity due to dynamic binding event and dissociation reactions over time, and the lower end of FIG. 17A shows dissociation time distribution and total occurrence rate of dissociation after binding event. FIG. 17B is a view comparing the dynamic analysis method of the present invention with a conventional data analysis method for the binding event and dissociation reaction of nanoparticles.

FIGS. 18A and 18B show the comparison of the highly reliable results for nanoparticle cluster system obtained from the dynamic analysis method of the present invention with those obtained from the conventional analysis method, in the real sample analysis. FIG. 18A shows the results obtained from the conventional analysis method, and FIG. 18B shows the results obtained from the dynamic analysis method of the present invention.

FIGS. 19A and 19B show the analysis results of target materials in an ultralow-concentration using the detection method of the present invention. FIG. 19A is a graph showing the selectivity between single-base-mismatched DNAs (SBMs) with respect to target DNAs (T, 95, 950 or 9500 DNA strands), and FIG. 19B shows the cumulative average valence of each target material over time through the detection of 95 target DNAs existing in 1% human serum.

FIGS. 21A and 21B show the mobility of nanoparticles formed on the SLB according to the fluid flow. FIG. 21A shows the moving trajectory of the nanoparticles according to the fluid flow rate, and FIG. 21B shows the drift velocity of the nanoparticles according to the fluid flow rate.

FIGS. 22A and 22B show the dark-field microscope images of gold nanoparticles and silver nanoparticles moved and concentrated on the pattern SLB by a fluid flow, respectively.

FIG. 23A shows the scattering spectra of metal nanoparticles under various salt (NaCl) concentrations, FIG. 23B shows the dark-field microscope images of metal nanoparticles, and FIG. 23C shows the changes in plasmonic scattering peaks and zeta potentials.

FIGS. 24A to 24C show the change in the scattering spectra of metal nanoparticles concentrated on the SLB patterned with silver nanoparticles by a fluid flow. FIG. 24A shows the scattering spectra of metal nanoparticles under various salt (NaCl) concentrations, FIG. 24B shows the dark-field microscope images of metal nanoparticles, and FIG. 24C shows the changes in plasmonic scattering peaks and zeta potentials.

FIG. 25 is a schematic view illustrating a method of analyzing the signal transfer mechanism of cells using a nanoparticle-tethered artificial cell membrane-based cell interfacing platform.

BEST MODE FOR INVENTION

Figure 1:
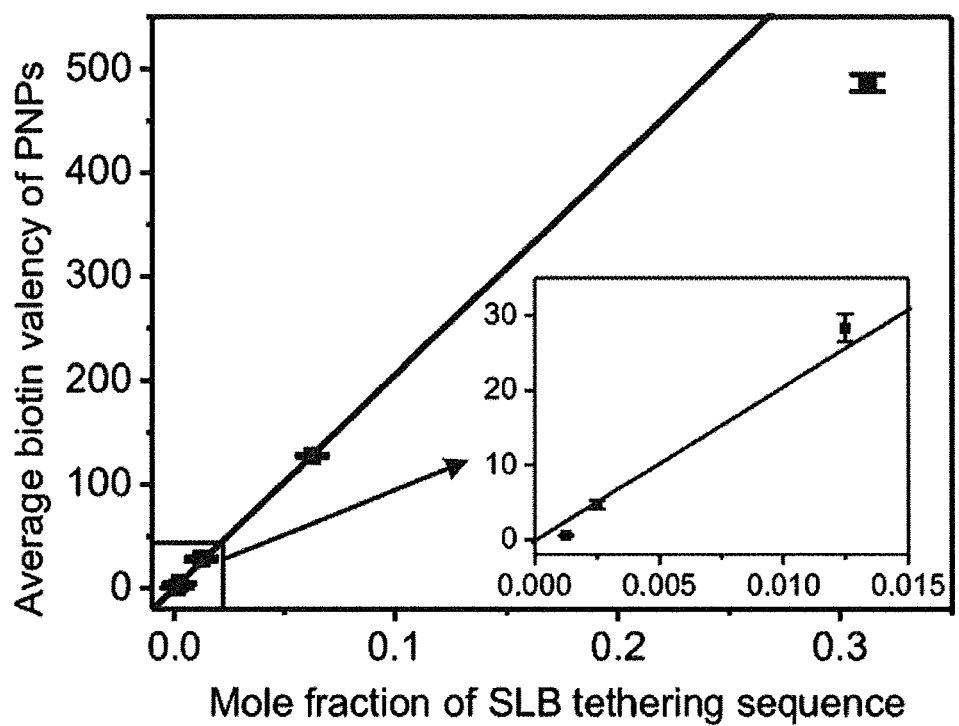
FIG. 1 is a graph illustrating the average number of biotinylated DNA sequences on PNP probes as a function of the mole fraction of the SLB tethering sequence. The values were obtained by averaging three different independently prepared samples. A linear fit was calculated with experimental values ranging from 0.00125 to 0.0625.
Figure 3A:
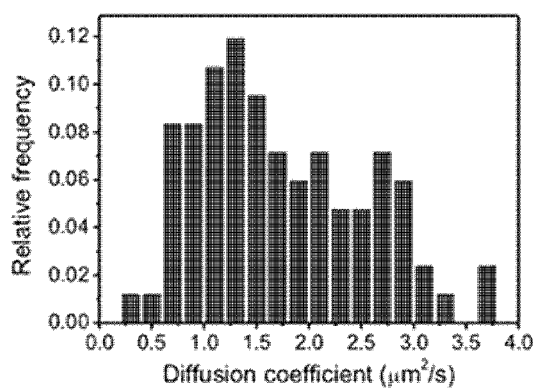
FIGS. 3A to 3D show graphs illustrating the distributions of diffusion coefficients as changing the biotin valency.
Figure 3B:
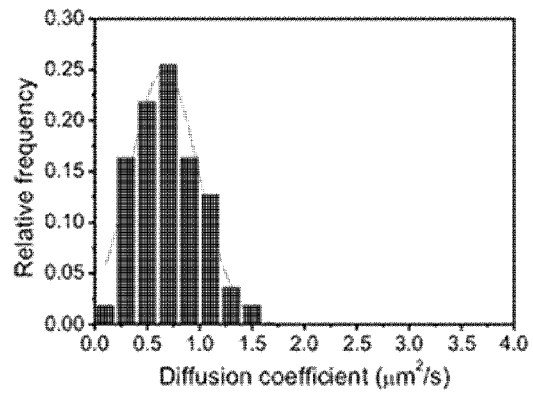
Figure 3C:
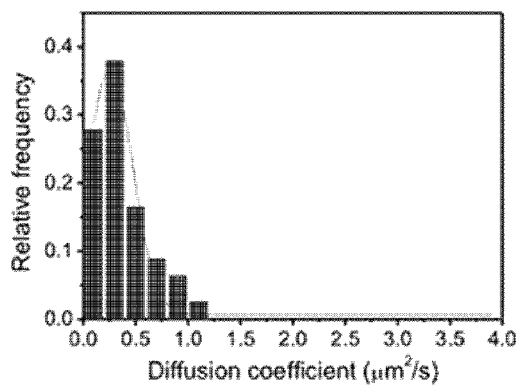
Figure 3D:
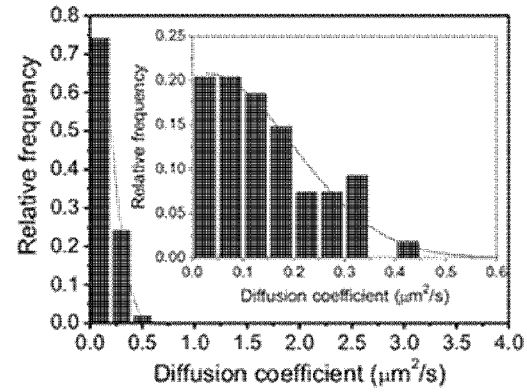

According to an aspect, the present invention provides an artificial cell membrane, comprising: a substrate; and a supported lipid bilayer (SLB) disposed on the substrate, wherein the supported lipid bilayer, within which some or all lipids are capable of shifting position, comprises a first lipid bound with a first ligand, and a first metal particle comprising a second ligand specifically binding to the first ligand at a density of 100 to 100,000/m² is bound to at least two of the first lipids through the binding between the first ligand and the second ligand, so as to decrease the mobility of the first metal particle in the supported lipid layer to 0 to $0.5 \times 10^{-8}$ cm²/s. The mobility of the first metal particle in the supported lipid layer may be decreased to 0 to $0.1 \times 10^{-8}$ cm²/s, and more preferably 0 to $0.01 \times 10^{-8}$ cm²/s, which cannot be detected by a microscope. When the mobility thereof is 0, the lipids are completely stopped.

As used herein, the term "substrate", which is a support capable of supporting a lipid bilayer, may be a solid substrate having a predetermined shape. Preferably, the substrate may be a transparent solid substrate made of glass, gold, silver, platinum, or $TiO_2$, or may be a transparent solid substrate made of an acrylic polymer, such as poly(methylmethacrylate) (PMMA), polyethylene (PE), polypropylene (PP), polystyrene (PS), polyethersulfone (PESX) polycycloolefin (PCO), polyurethane, or polycarbonate (PC). Further, as the substrate, a substrate coated with a coating agent that can be hydrated, such as cellulose, may also be used as long as the fluidity of the lipid bilayer introduced onto a coating film can be maintained.

As used herein, the term "supported lipid layer" may be an in via-assembled lipid bilayer surrounding a quasi-cell structure, such as a natural cell membrane or a nucleus, may be a kind of model lipid bilayer made of synthetic or natural lipid, and may be anchored to a solid substrate to have improved stability. Therefore, the supported lipid layer may be used as a characterization tool that cannot be used in a bulk solution. The supported lipid layer, unlike a vesicle or cell membrane obtained by combining lipid bilayers in the form of a round closed cell, is a planar structure formed on a solid substrate. Therefore, only the upper surface of the lipid bilayer is exposed to a free solution. Such a configuration has advantages and disadvantages in relation to the study of lipid bilayers. The main advantage of the supported lipid bilayer is stability. The supported lipid bilayer (SLB) is not seriously damaged even when it is exposed to rapid flow or vibration. In the supported lipid bilayer (SLB), unlike a black lipid membrane (BLM), which is another model lipid bilayer, the presence of holes does not destroy the entire bilayer. Due to such stability, SLB experiments can be carried out for several weeks to several months, whereas BLM experiments are restricted to several hours. The SLB is also advantageous in that it cannot be used for freely floating specimens or can be used as a characterization tool for providing low resolution.

The most obvious example of these advantages is that mechanical probing techniques requiring the direct physical interaction with specimens can be used. In order to image the phase separation of lipids, the formation of membrane-penetrating nanopores leading to single protein molecule adsorption, and the assembling of protein with sub-nanometer accuracy without dye labeling, atomic force microscopy (AFM) is used. Recently, in order to directly detect the mechanical properties of a single lipid bilayer, AFM is used in performing power spectroscopy on individual membrane proteins. Since the surface of a cell or vesicle is relatively soft and changes depending on time, the aforementioned study may be difficult or impossible without using SLB.

Meanwhile, even in various modern fluorescence spectroscopies, a rigidly-supported planar surface is required. Evanescent field methods, such as total internal reflection fluorescence microscopy (TIRF) and surface plasmon resonance (SPR), can measure the bonding of an analyte and the optical properties of a bilayer with high sensitivity, but can be operated only when a specimen is supported on a substrate having an optical function. Examples of other methods applicable only to the supported bilayer include fluorescence interference contrast microscopy (FLIC) and reflection interference contrast microscopy (RICM).

Generally, SLB is not directly in contact with the surface of a substrate, and is separated from the substrate through a very thin water layer. The size and properties of the water layer depend on the material of the substrate and the kind of lipid, but the thickness of the water layer is generally about 1 nm with respect to a zwitterionic lipid supported on silica, which is the most widely used experimental system. Since the water layer is very thin, extensive hydrodynamic coupling exists between the supported lipid bilayer and the substrate, and thus the supported lipid bilayer has a lower diffusion coefficient than a free lipid bilayer. A part of the lipids in SLB may be completely fixed. The fraction of the fixed lipids in SLB is 1% to 5%.

Generally, the "artificial cell membrane" may be a lipid membrane-containing system for imitating the in vivo cell membrane system in a test tube, the system being artificially fabricated in order to study the cell membrane-related phenomena occurring on the surface of cells in vivo, such as cell membrane proteins, membrane-penetrating proteins, and interactions related thereto. Examples of the model systems providing the artificial cell membrane include a black lipid membrane (BLM), a supported lipid bilayer (SLB), a tethered bilayer lipid membrane (tBLM), a vesicle, a micelle, a bicelle, and a nanodisc. In particular, SLB is a useful means for identifying biophysical cell membrane phenomena. SLB can control mobility and activity due to the change of chemical composition as well as environmental variables, such as pH and temperature.

Each of the first ligand and the second ligand may be selected from antigens, antibodies, ligands, receptors, chelates, DNA, RNA, aptamers, chemical molecules specifically binding to each other, and combinations thereof, but is not limited thereto. For example, when the first ligand is an antibody, the second ligand may be an antigen specific to the antibody. Further, the second ligand may be bonded with the first ligand by a sandwich immune reaction for forming an antibody-antigen-antibody complex by combining all antibodies additionally bonded to the antigen with the antibody. As another example, the first ligand and the second ligand may be DNA fragments having sequences complementary to each other, and in this case, the first ligand and the second ligand may be bonded to each other by the hybridization of these DNA fragments.

In an exemplary embodiment of the present invention, biotin, as the first ligand, is attached to other binding sites containing no streptavidin by using biotin as the first ligand and using a conjugate of biotin and streptavidin (receptor of biotin) as the second ligand.

The first metal particle may be bonded to a lipid by specific antigen-antibody bonding, ligand-receptor bonding, DNA hybridization, chelation, covalent bonding, electrostatic bonding, or chemical reaction bonding, between the first ligand on the lipid and the second ligand on the surface of a metal particle. In this case, the first metal particle may include the plurality of second ligands, and one metal particle may be bonded to a plurality of lipid particles depending on density. In this case, the movement of an individual lipid molecule on a lipid membrane is free.

However, in the case where the plurality of lipid molecules are bonded to one metal particle, the movement thereof is relatively restricted because the plurality of lipid molecules bonded to one metal particle should be moved organically on a 2-dimensional plane in order to move the metal particle.

According to an exemplary embodiment of the present invention, as valency per unit particle increases, the movement of particles is remarkably retarded. As a result, the movement of particles is almost not captured, as the particles are fixed, when the valency reaches 486 (refer to FIGS. 2 and 6).

The method of monitoring the movement of the first metal particle is not particularly limited, but preferably, may be performed by measuring plasmonic scattering.

Preferably, the second ligand includes a thiol group, and may be covalently bonded to the first metal particle through the thiol group.

The artificial cell membrane of the present invention is characterized in that metal particles are bonded thereto as probes. Since the metal particles are stable compared to particles, such as vesicles composed of a polymer or a lipid bilayer, they are not decomposed even under conditions of relatively low or high salt concentration or pH so as to maintain their forms and physical properties. Further, preferably, since the metal particles include plasmonic metal particles and exhibit plasmonic scattering, the metal particles themselves can be detected without additional probes, and do not cause flickering or extinction so as to perform stable monitoring for a long period of time. Moreover, since the metal particles can directly form strong covalent bonds together with a functional group, such as a thiol group, ligands can be provided to the surface thereof using this function group.

Preferably, the first lipid bound with the first ligand may be included in an amount of 0.05 mol % to 0.5 mol % with respect to the total amount of lipids in the supported lipid bilayer. The first ligand is a site at which particles are disposed by bonding with the second ligand. When the ratio of the amount of the first lipid bound with the first ligand to the total amount of lipids is less than 0.05 md/%, the frequency of the first ligands on the surface of lipid becomes low, that is, the distance between the first ligands increases, and thus one particle is bonded to the plurality of first ligands, so it is difficult for particles to be fixed on the lipid bilayer. When the ratio thereof is more than 0.5 mol %, the density of the first ligands becomes excessively high, the aggregation of first particles including the second ligands specifically binding to the first ligands is caused so as to inhibit the movement of the particles or make the analysis thereof difficult.

Preferably, the supported lipid bilayer may further include a second lipid bound with polyethylene glycol (PEG) in an amount of 1 mol % to 10 mol % with respect to the total amount of lipids. In this case, the average molecular weight of polyethylene glycol is preferably 500 to 2000, but is not limited thereto. For example, when PEG having a relatively low molecular weight of 2000 or less is used, even though the content of the second lipid bound with PEG is increased to a level of 10 mol %, which is a somewhat higher content than the content used to stabilize a lipid bilayer, a screening effect is not caused, the lipid layer is physically stabilized to increase the lifespan and stability of the lipid bilayer, and the nonspecific bonding between nanoparticles and between nanoparticles and the lipid bilayer is efficiently reduced to increase fluidity. However, when the molecular weight of PEG exceeds the above range or the content of the second lipid exceeds the above range, the approach of nanoparticles to a lipid membrane and/or the bonding between the first ligand and the second ligand may be inhibited by causing a screening effect, so it is preferable that the molecular weight of PEG used and the content of the second lipid bound with PEG are combined and selected appropriately.

According to another aspect, the present invention provides an analysis device for examining the interaction between molecule A and molecule B using an artificial cell membrane, comprising: the artificial cell membrane, in which a supported lipid bilayer further comprises a third lipid bound with a third ligand which is the same as or different from the first ligand; the molecule A bound to the surface of the first metal particle in the artificial cell membrane; a second metal particle comprising a fourth ligand specifically binding to the third ligand, wherein the second metal particle binds to at least one of the third lipids through the interaction between the third ligand and the fourth ligand, and has higher mobility compared to that of the first metal particle; and the molecule B bound to the surface of the second metal particle in the artificial cell membrane, wherein the second metal particle having higher mobility approaches the first metal particle and is then confined to the first metal particle by the interaction between the molecule A and the molecule B.

The fourth ligand may be the same as or different from the second ligand.

Each of the molecule A and the molecule B may be selected from DNA, RNA, antigens, antibodies, ligands, chelates, receptors, aptamers, polymers, organic compounds, metal ions, and polypeptides.

Therefore, the interaction between the molecule A and the molecule B to be examined by the analysis device of the present invention may be antigen-antibody bonding, ligand-receptor bonding, protein-protein bonding, nucleic acid hybridization, chelation, covalent bonding, or electrostatic bonding. The nucleic acid hybridization may include the hybridizations of DNA, RNA, PNA, and combinations thereof without limitation.

The first metal particles are fixed on the supported lipid bilayer through the bonding with a plurality of lipids, and the second metal particles can perform 2-dimensional free Brownian motion on the supported lipid bilayer in the absence of the interaction between the molecule A and the molecule B.

Therefore, when the stimulus due to the interaction between the molecule A on the first metal particle and the molecule B on the second metal particle, that is, the attractive force or repulsive force between the first metal particle and the second metal particles, is generated, the first metal particle may be fixed, and the second metal particle may be moved toward the first metal particle by attractive force or may be moved away from the first metal particle by repulsive force. Therefore, the interaction between the molecule A and the molecule B may be examined by observing the movement of the second metal particle relative to the fixed first metal particle.

According to still another aspect, the present invention provides a method of examining the interaction between the molecule A and the molecule B using the analysis device.

As described above, in the analysis device, the first metal particle is fixed on the plane of the supported lipid bilayer, and the second metal particle performs free Brownian motion as long as additional stimuli are not applied.

Therefore, the position of the first metal particle and the change in scattering intensity or wavelength due to the first metal particle may be monitored.

Further, the real-time movement trajectory or speed of the second metal particle, or the change in signal intensity or wavelength due to the second metal particle may be monitored.

Preferably, the monitoring is performed by measuring the plasmonic scattering of the first metal particle and/or the second metal particle. Nanoparticles causing plasmonic scattering can enhance scattering signal through plasmonic coupling when the distance therebetween decreases, and scattering wavelengths are shifted to long wavelengths when the distance therebetween further decreases within a predetermined distance, that is, a plasmonic coupling distance. Therefore, when particles are far away from each other, the distance between the particles can be measured from the trajectory of the particles, and when the particles are closer to each other within a predetermined distance, the distance between the particles can be estimated from the intensity and wavelength of the measured scattering signal.

In an exemplary embodiment of the present invention, gold nanoparticles labeled with complementary sequence DNA are used, and two or more DNAs are bonded to one gold nanoparticle, and thus the plurality of gold nanoparticles are closer to each other by the hybridization of DNAs. As a result, the number of the gold nanoparticles bonded to each other increases, and thus the gold nanoparticles are grown in order of dimers, trimers, and tetramers, so that scattering intensity increases stepwise, and scattering signals are continued for a long time. In contrast, the increase of signals is observed by transient non-specific interactions, but the corresponding signals are not continued even for several seconds. Therefore, it is ascertained that the increase of signals by non-specific interactions and the increase of signals by specific interactions are distinguished from each other (refer to FIG. 6). Further, it is ascertained that, due to the aggregation of the particles, signal intensity is increased, and scattering wavelengths are converted into long wavelengths.

This method is characterized in that the density of particles and the collision frequency of particles are increased by applying an additional force in a predetermined direction, thereby improving analytic sensitivity and shortening detection time. In this case, the applied force may be a magnetic field, an electric field, or a fluid flow, but is not limited thereto.

According to still another aspect, the present invention provides analysis kit for determining the binding between molecule A and molecule B by determining the distance between a first metal particle and a second metal particle from plasmonic scattering signals of the first metal particle bound with the molecule A and the second metal particle bound with the molecule B on an artificial cell membrane, comprising: an artificial cell membrane comprising a substrate, a supported lipid bilayer which is disposed on the substrate and within which some or all lipids are capable of shifting position, and a first lipid bound with a first ligand and a third lipid bound with a third ligand, which is the same as or different from the first ligand, as a part of the supported lipid bilayer, a first metal particle comprising a second ligand specifically binding to the first ligand, wherein the first metal particle is able to bind to at least one of the first lipids through the interaction between the first ligand and the second ligand, and a second metal particle comprising a fourth ligand specifically binding to the third ligand, wherein the second metal particle is able to bind to at least one of the third lipids through the interaction between the third ligand and the fourth ligand.

As described above, in order to examine the interaction between two molecules, it is preferable for the convenience of detection that an analysis device, which is configured such that the metal particle bonded with one molecule of the two molecules to be analyzed is fixed on the artificial cell membrane and the other molecule is bonded to the metal particle having relatively high mobility, is used. However, according to current optical detection techniques, since the particles freely moving on a lipid bilayer can be monitored, the individual particle can also be monitored even though these particles are able to move freely on the lipid bilayer because both molecule A and molecule B are bonded to the metal particle having high mobility. Therefore, this system can also be used as an analysis kit for examining the interaction between the molecule A and the molecule B. This analysis kit can also be applied to a commonly-known plasmonic scattering detecting system.

According to still another aspect, the present invention provides a kit for qualitative or quantitative analysis of a target material capable of binding to molecule A and molecule B which is used to determine the binding between the molecule A and the molecule B by determining the distance between a first metal particle and a second metal particle from plasmonic scattering signals of the first metal particle bound with the molecule A and the second metal particle bound with the molecule B on an artificial cell membrane, comprising: an artificial cell membrane comprising a substrate, a supported lipid bilayer which is disposed on the substrate and within which some or all lipids are capable of shifting position, and a first lipid bound with a first ligand and a third lipid bound with a third ligand, which is the same as or different from the first ligand, as a part of the supported lipid bilayer, a first metal particle comprising a second ligand specifically binding to the first ligand, wherein the first metal particle is able to bind to at least one of the first lipids through the interaction between the first ligand and the second ligand; the molecule A which is bound to the surface of the first metal particle and which is specifically bound to a portion of the target material; a second metal particle comprising a fourth ligand specifically binding to the third ligand, wherein the second metal particle is able to bind to at least one of the third lipids through the interaction between the third ligand and the fourth ligand; and the molecule B which is bound to the surface of the second metal particle in the artificial cell membrane and which is specifically bound to another portion of the target material on which the molecule A is not bound.

As described above, each of the target material, the molecule A, the molecule B, the first ligand and the second ligand may be selected from antigens, antibodies, ligands, receptors, chelates, DNA, RNA, aptamers, chemical molecules specifically binding to each other, and combinations thereof.

Although not limited thereto, when the valency is adjusted such that the first metal particle is fixed on the supported lipid bilayer and the second metal particle can conduct 2-dimensional free Brownian motion on the supported lipid bilayer through the target material at the time of absence of the interaction between the molecule A and the molecule B, the relative movement of the second metal particle to the fixed first metal particle can be tracked so as to facilitate monitoring.

In this case, the interactions between the molecule A and the target material and between the molecule B and the target material in the presence of the target material can be examined by measuring the changes in the intensity and/or wavelength of a plasmonic scattering signal at the position of the first metal particle, the changes being caused by the bonding between the molecule A and the target material and between the molecule B and the target material when the second metal particle having high mobility approaches the first metal particle.

According to still another aspect, the present invention provides a multiple analysis kit for qualitative or quantitative analysis of target materials in the amount of $i_{max} \times m_{max}$ by the plasmonic scattering measurement ($i_{max}$ and $m_{max}$ are maximum values of the following variables i and m, respectively, and are each independently an integer of 1 or more, but not $i_{max}=m_{max}=1$), comprising: an artificial cell membrane comprising a substrate, a supported lipid bilayer which is disposed on the substrate and within which some or all lipids are capable of shifting positions, and a lipid $I_i$ bound with a ligand $I_i$ and a lipid $M_m$ bound with a ligand $M_m$ (herein, the ligand $I_i$ and the ligand $M_m$ may be the same as or different from each other); a metal particle $I_i$ comprising a ligand $I'_i$ specifically binding to the ligand $I_i$, wherein the metal particle $I_i$ is bound to at least one of the lipids $I_i$ through the interaction between the ligands $I_i$ and the ligand $I'_i$; a molecule $A_i$ which is bound to the surface of the metal particle $I_i$ and is specifically bound to a portion of the target material; a metal particle $M_m$ comprising a ligand $M'_m$ specifically binding to the lipid $M_m$, wherein the metal particle $M_m$ is bound to at least one of the lipids $M_m$ though the interaction between the ligand $M_m$ and the ligand $M'_m$; and a molecule $B_m$ which is bound to the surface of the metal particle $M_m$ in the artificial cell membrane and which is specifically bound to another portion of the target material on which the molecule A is not bound, wherein the series of the metal particles $I_i$ have different plasmonic scattering wavelengths from one another, and the series of the metal particles $M_m$ have different plasmonic scattering wavelengths from one another.

Figure 28A:
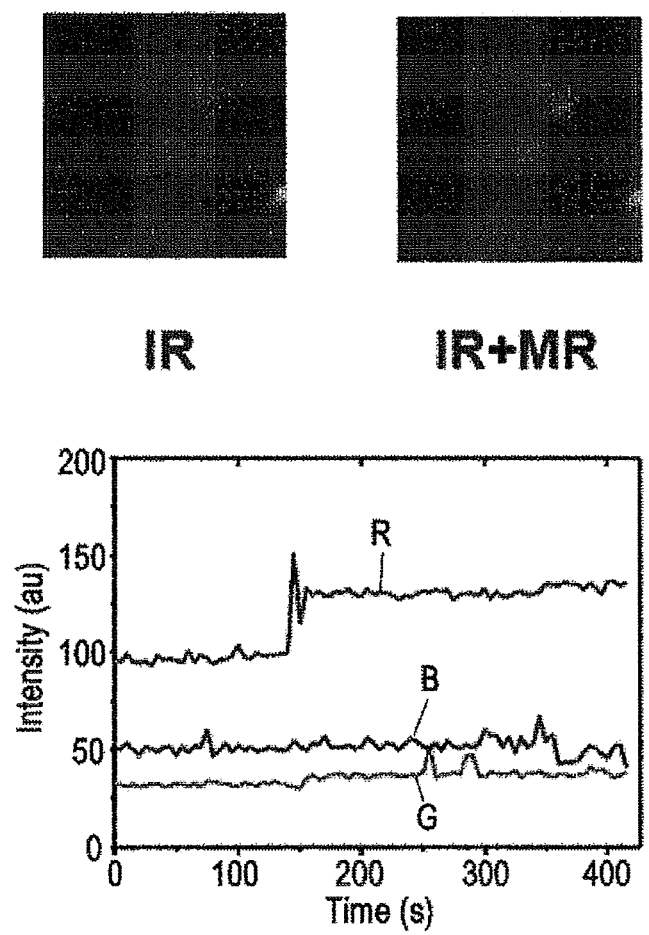
FIG. 28A shows the dark-field microscope images of fixed red nanoparticles and movable red nanoparticles interacting with the fixed red nanoparticles, and the change in intensity of three-color plasmonic scattering spectra at the position of the fixed red nanoparticles with respect to time.
Figure 29A:
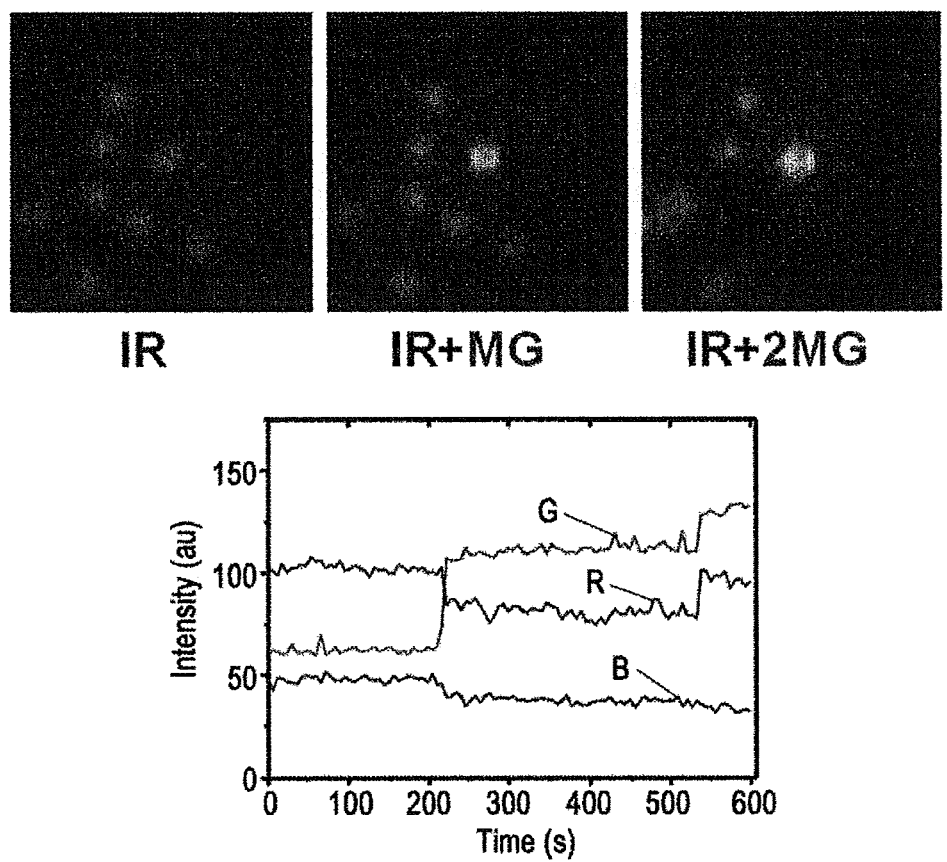
FIG. 29A shows the dark-field microscope images of fixed red nanoparticles and one or more movable green nanoparticles interacting with the fixed red nanoparticles, and the change in intensity of three-color plasmonic scattering spectra at the position of the fixed red nanoparticles with respect to time.
Figure 29B:
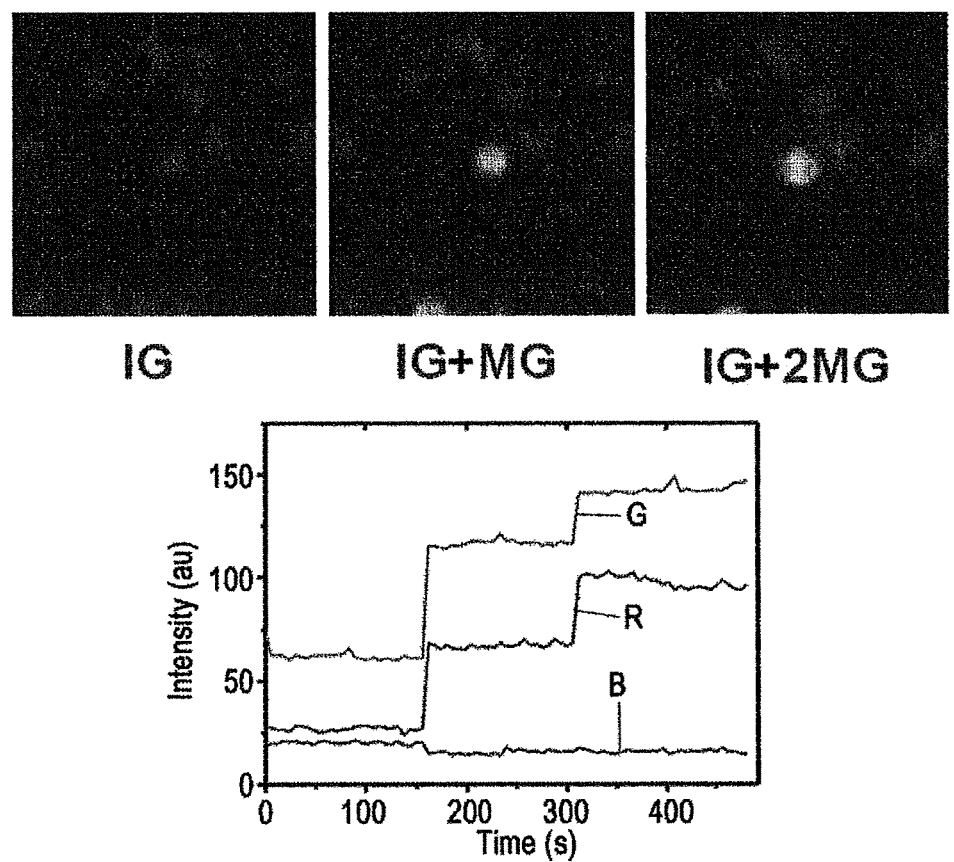
FIG. 29B shows the dark-field microscope images of fixed green nanoparticles and one or more movable green nanoparticles interacting with the fixed green nanoparticles, and the change in intensity of three-color plasmonic scattering spectra at the position of the fixed green nanoparticles with respect to time.
Figure 30A:
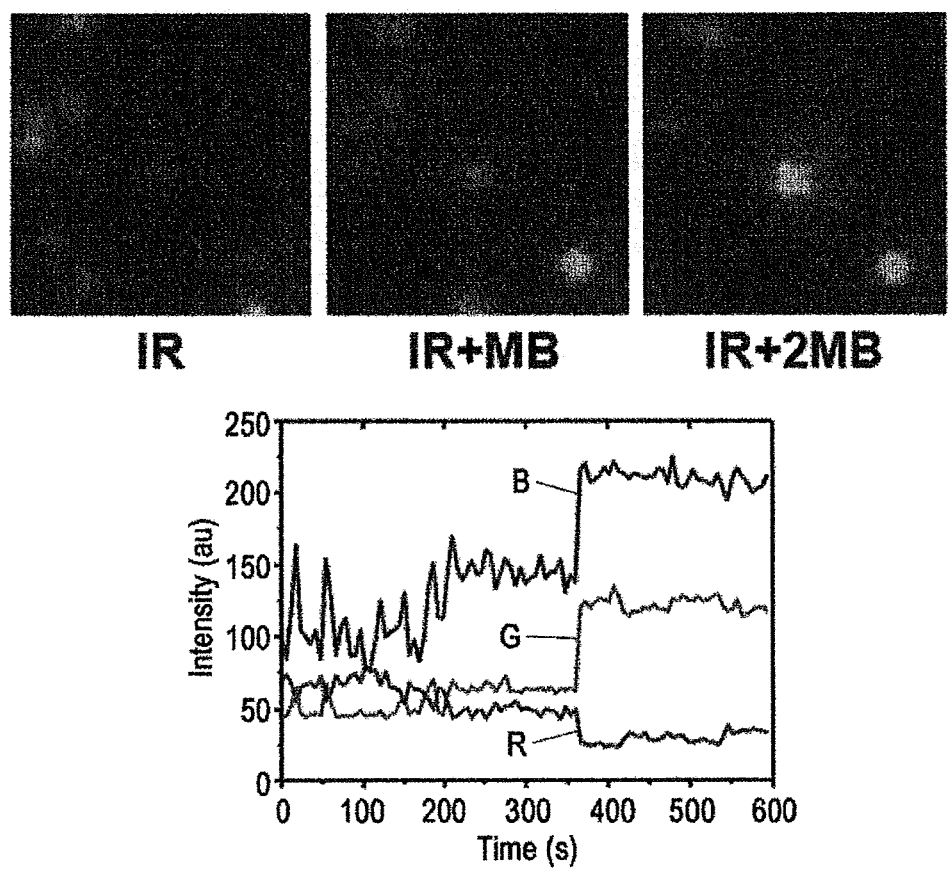
FIG. 30A shows the dark-field microscope images of fixed red nanoparticles and one or more movable blue nanoparticles interacting with the fixed red nanoparticles, and the change in intensity of three-color plasmonic scattering spectra at the position of the fixed red nanoparticles with respect to time.
Figure 30B:
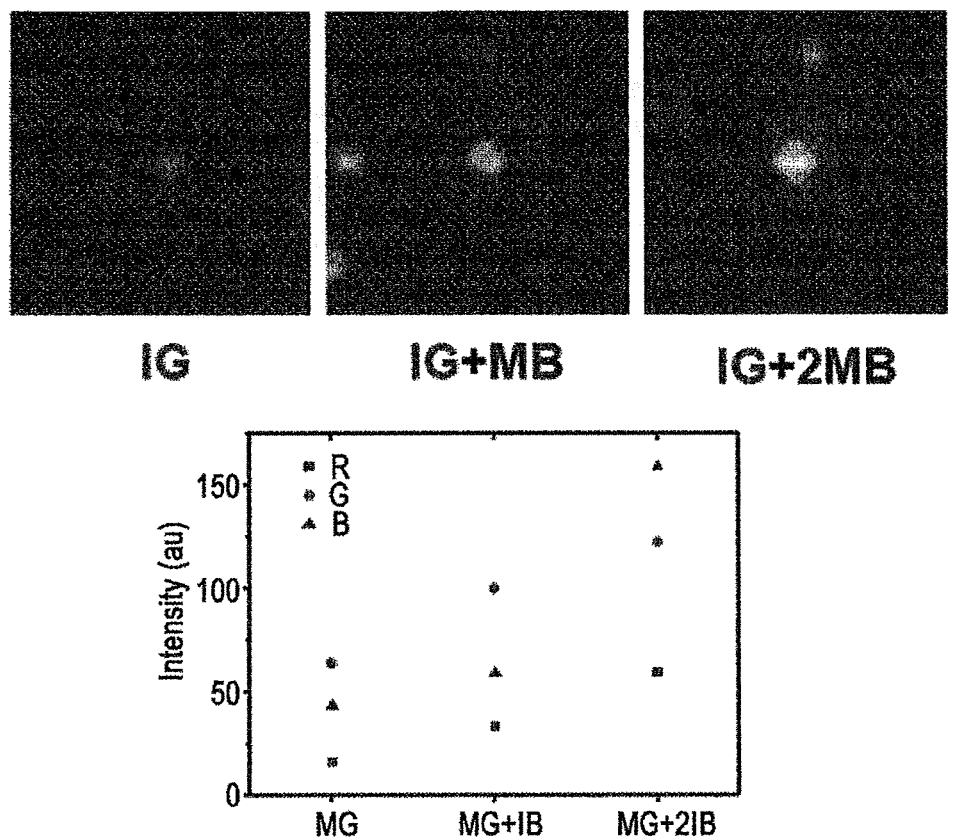
FIG. 30B shows the dark-field microscope images of fixed green nanoparticles and one or more movable blue nanoparticles interacting with the fixed green nanoparticles, and the change in intensity of three-color plasmonic scattering spectra at the position of the fixed green nanoparticles with respect to time.
Figure 30C:
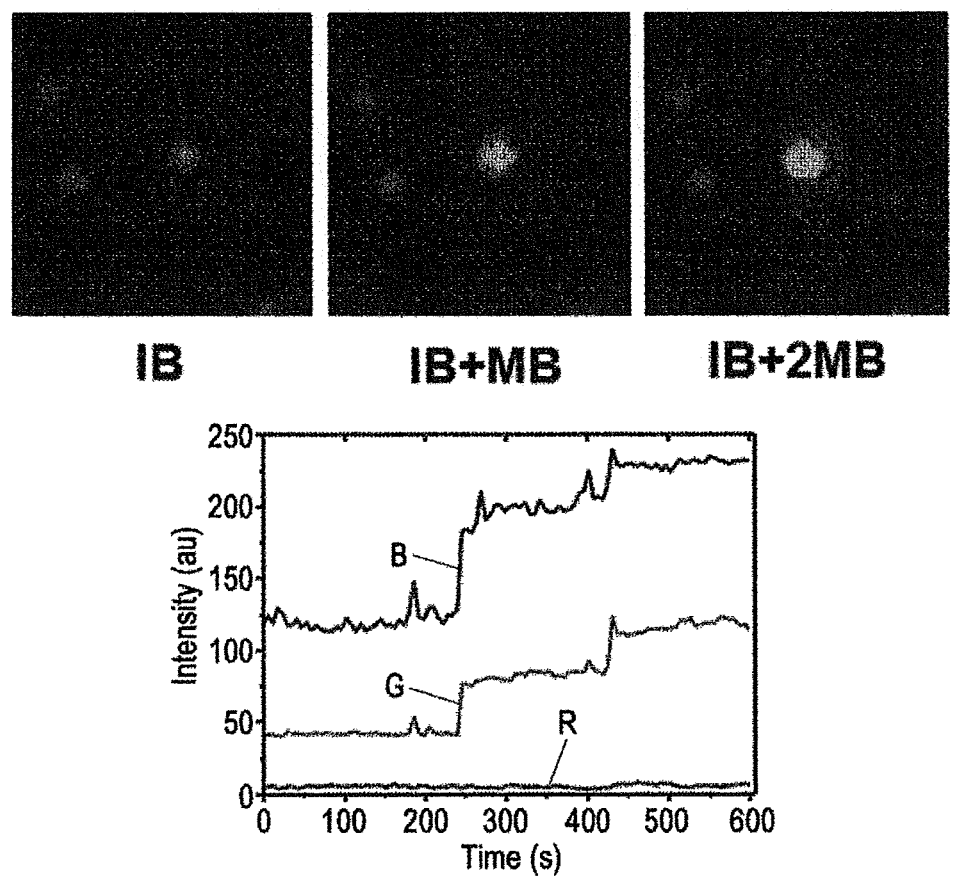
FIG. 30C shows the dark-field microscope images of fixed blue nanoparticles and one or more movable blue nanoparticles interacting with the fixed blue nanoparticles, and the change in intensity of three-color plasmonic scattering spectra at the position of the fixed blue nanoparticles with respect to time.

In an exemplary embodiment of the present invention, gold/silver nanoparticles having different colors, that is, red, green, and blue colors, are prepared, and DNAs having a capture sequence and a complementary sequence and bonded onto a lipid bilayer are provided to the surface of the gold/silver nanoparticles at a predetermined rate to control the valency with the lipid bilayer, thereby providing six types of different metal particles, that is, metal particles fixed on the lipid bilayer and metal particles moving freely on the lipid bilayer. In addition, complementary sequence DNAs that can be bonded to some of nine types of miRNAa, which are used as target materials, are provided to the surface of the gold/silver nanoparticles (refer to FIG. 27B, FIG. 32, and Table 3). In this case, for the convenience of monitoring, DNA sequences are combined such that each of the target materials is bonded to one metal particle fixed on the lipid bilayer and another metal particle moving freely on the lipid bilayer. For example, the plasmonic scattering of a red metal particle fixed on the lipid bilayer, the trajectory of another metal particle approaching this red metal particle depending on time, and the intensity of plasmonic scattering at three color wavelengths are monitored to identify the wavelength, the intensity of which is increased according to the approach of another metal particle, among the three color wavelengths so as to identify the kind of another metal particle, and the number of other metal particles bonded to one fixed red metal particle is determined by measuring the increased intensity. That is, it can be ascertained that the plasmonic scattering pattern of the fixed red metal particle is different from that of three types of metal particles capable of moving freely on the lipid bilayer being able to be bonded to the red metal particle by monitoring the position of the fixed red metal particle (refer to FIGS. 28A, 29A, and 30A). This result is obtained in a manner similar to that in the case of using fixed green metal particles and fixed blue metal particles (refer to FIGS. 28 to 30B, and 30C), and different plasmonic scattering changes are caused by the combination thereof (refer to FIG. 27D). Thus, it can be ascertained that a plurality of target materials can be simultaneously analyzed qualitatively and quantitatively by using a plurality of metal particles having different mobility and/or plasmonic scattering wavelengths.

According to still another aspect, the present invention provides a method of concentrating particles into a specific area of a fluid channel, comprising: preparing a supported lipid bilayer in the fluid channel, wherein the supported lipid bilayer comprises a first lipid bound with a first ligand, and some or all lipids are capable of shifting positions in the supported lipid bilayer, applying a first particle comprising a second ligand specifically binding to the first ligand onto the supported lipid bilayer, and transferring the first particles into the specific area of the fluid channel by applying a fluid flow in the fluid channel.

If necessary, as the first particles, particles bound with genes or proteins may be used.

When a fluid flow is applied to the fluid channel including the supported lipid layer including particles bonded onto a lipid through ligand binding, the particles can perform free Brownian motion on the supported lipid bilayer, and thus the particles move along the flow direction of fluid to be concentrated at a specific portion. Conventionally, as the method of concentrating the particles disposed on the lipid bilayer, methods of applying a stimulus, such as an electric field, have been used. However, when an electric field is applied, as exposure time increases, proteins or genes bonded to particles may be denatured, or the lipid bilayer itself may be destroyed, and thus experimental conditions, such as pH, temperature, and air bubble generation, may be changed. However, when the flow of fluid according to the present invention is used, the above disadvantages can be overcome.

In an exemplary embodiment of the present invention, a flow channel is provided on a substrate, and holes are formed in both sides of an upper slide glass so as to allow fluid to flow in a predetermined direction. The lipid bilayer bound with gold or silver nanoparticles according to the present invention is formed in the flow channel, and the movement of the metal nanoparticles is monitored while adjusting the flow rate of fluid. The metal nanoparticles are freely moved and diffused before the flow of fluid is applied, but these metal nanoparticles start to move in the same direction as the flow of fluid while the flow of fluid is applied, and the movement of the metal nanoparticles is accelerated with the increase in the flow of fluid. Further, as the metal nanoparticles move in one direction, the density of the metal nanoparticles in the specific area increases, and scattering wavelengths are shifted by plasmonic coupling (refer to FIGS. 11A to 11D and 12A to 12B).

MODE FOR INVENTION

Hereinafter, the present invention will be described in more detail with reference to the following Examples. These Examples are set forth to illustrate the present invention, and the scope of the present invention is not limited thereto.

Example 1: Materials 1,2-Dioleoyl-sn-glycero-3-phosphocholine (DOPC), 1,2-dioleoyl-sn-glycero-3-phosphoethanolamine-N-(cap biotinyl) sodium salt (biotinylated DOPE), and 1,2-dioleoyl-sn-glycero-3-phosphoethanolamine-N-[methoxy(polyethylene glycol)-1000] ammonium salt (PEG-DOPE) were purchased from Avanti Polar Lipids (Alabaster, Ala., USA). Cy3-modified streptavidin (STV) was purchased from Molecular Probes (Eugene, Oreg. USA). Carboxymethyl polyethylene glycol (M.W. 5000) was purchased from Laysan Bio Inc. (Arab, Ala., USA). Bovine serum albumin (BSA), sodium dodecyl sulfate (SDS), and dithiothreitol (DTT) were purchased from Sigma-Aldrich (St. Louis, Mo., USA). A 0.15 M phosphate-buffered saline (PBS) solution was prepared by dissolving $NaH_2PO_4$, $Na_2HPO_4$, and NaCl (Sigma-Aldrich, St. Louis, Mo., USA) in deionized water (DI water), yielding a 10 mM phosphate buffer solution with 150 mM NaCl (pH 7.4). Further, 0.025 M PBS was prepared to contain 25 mM NaCl with the same reagents. Nanopure water with the minimum resistance (>18 MΩ/cm) was used in all of the experiments. For vesicle preparation (vesicle extrusion), polycarbonate (PC) filters (Whatman, Fisher Scientific) with a pore diameter of 100 nm were used. Organic solvents such as chloroform, acetone, and ethanol were purchased from Duksan Pure Chemicals Co. Ltd. (Gyeonggi-do, South Korea). Sulfuric acid and hydrogen peroxide were purchased from Daejung Chemicals & Metals Co. Ltd. (Gyeonggi-do, South Korea). 50 nm gold nanoparticles and oligonucleotides were purchased from BBI Life Sciences (Cardiff, UK) and Integrated DNA Technology (Coralville, Iowa, USA), respectively. The target capture sequence for I-PNP (immobile PNP) is (SEQ ID NO: 1)
5'-HS-(CH$_2$)$_6$-PEG$_6$-CTTTGAGCAC<u>ATCCTTATCAATATT</u>-3' and the SLB tethering sequence for I-PNP is (SEQ ID NO: 2)
5'-HS-(CH$_2$)$_6$-PEG$_6$-CTTTGAGCACTGTTAGCGTGTGTGGAATTTTAAT-biotin-3'.

The target capture sequence for M-PNP (mobile PNP) is (SEQ ID NO: 3)
5'-<u>TAACAATAATCCCTC</u>CACGAGTTTC-PEG$_6$-(CH$_2$)$_3$-SH-3' and the SLB tethering sequence for M-PNP (mobile PNP) is (SEQ ID NO: 4)
5'-biotin-TAATTTTAAGGTGTGTGCGATTGTCACGAGTTTC-PEG$_6$-(CH$_2$)$_3$-SH-3'.

The target sequence (SEQ ID NO: 5)
5'-GAGGGATTATTGTTAAATATTGATAAGGAT-3'.

The underlined parts of target capture sequences hybridize with the target DNA sequence. As the single base pair-mismatched DNA sequence, a target DNA sequence in which A is replaced by T was used. The non-complementary DNS sequence was (SEQ ID NO: 6)
5'-CTGATTACTATTGCATCTTCCGTTACAACT-3'.

Example 2: Preparation of Small Unilamellar Vesicle (SUV)

A supported lipid bilayer (SLB) was formed on a cover glass by the diffusion of SIV containing 97.4 mol % of DOPC, 0.1 mol % of biotinylated DOPE, and 2.5 mol % of PEG-DOPE. A SUV solution was prepared by dissolving an appropriate amount of a lipid in chloroform. A lipid solution was evaporated in a 50 ml round-bottom flask using a rotary evaporator. A lipid film was completely dried under a stream of $N_2$. The dried mixture was resuspended in DI water and subjected to three repetitive free-thaw cycles. The total lipid concentration was 2 mg/ml. The solution was extruded more than 21 times through a PC membrane with a pore diameter of 100 nm at 25° C. The resulting SUV solution was kept at 4° C. until use.

Example 3: Functionalization of Gold Plasmonic Nanoprobes Using DNA and Quantification of Biotin Valency Thiolated oligonucleotides were reduced by incubation with 100 mM PB (pH 8.0) for 2 h and separated by NAP-5 columns (GE Healthcare, Buckinghamshire, UK). For DNA functionalization, freshly reduced 4 μM oligonucleotides were mixed with 50 μM AuNPs of 50 nm and incubated at room temperature overnight. For I-PNP, the molar ratio of the SLB tethering sequence to the target capture sequence was 200:600 (mole fraction of SLB tethering sequence: 0.25). For M-PNP the molar ratio was 1:799 (mole fraction of SLB tethering sequence: 0.00125). The solution was then adjusted to yield 10 mM of phosphate buffer and 0.1% (wt/vol) SDS. The adjusted solution was further incubated in an orbital shaker for 30 min and six aliquots of 2 M NaCl were added by 0.05 M increments to obtain a final NaCl concentration of 0.3 M. After each addition of 2 M NaCl, the solution was heated at 55° C. for 10 min and incubated for 30 min at room temperature. The DNA-AuNP mixture was allowed to stand overnight at room temperature and the solution was then centrifuged (4500 rpm, 10 min). The supernatant was eliminated and the precipitate was redispersed in DI water (this procedure was repeated three times). The DNA-functionalized AuNP solution was kept at 4° C. until use. For quantification of the number of SLB tethering sequences per AuNP, the Cy3-labeled oligonucleotide-modified AuNPs were dissolved with a 30 mM KCN solution. Further, measurement of fluorescence emission intensity of Cy3 was performed on an Acton spectrometer (Spectra Pro, MA, USA) with a Xe lamp (500 W) as an excitation source.

Example 4: Preparation of SLB and Gold Plasmonic Nanoparticles Tethered to SLB

Preparation of SLB and Au PNPs tethered to the SLB was conducted in a glass flow chamber. The glass flow chamber consists of top and bottom glass substrates which are separated from each other by a 100 μm-thick thermoplastic spacer. Inlet and outlet holes were drilled on both ends of the top glass substrate. The top slide glass was pre-treated with 10 mg/ml BSA in 0.15 M BPS for 1 h to make it inert to SLB deposition. The bottom cover glass was cleaned by sonicating for 10 min in chloroform, acetone, and ethanol. After sonication, the cover glass was washed with DI water and dried by a stream of $N_2$. Next, the bottom cover glass was pre-treated with 1 M NaOH for 1 h and then completely washed with DI water. The glass substrates were assembled with a sandwiched thermoplastic spacer by heating at 120°

C. on a digital hot plate. The prepared SUV solution was mixed 1:1 v/v with 0.15 M PBS and introduced into the glass flow chamber through the inlet port. Approximately 70 µl of the SUV solution was required to fill the flow channel. After 45 min of incubation at 25° C., excess and unfused SUVs were washed out with 200 µl of DI water two times. 1 nM STV in a 0.15 M PBS solution was reacted with biotinylated SLB for 1 h after replacing DI water in the flow channel with PBS. Unreacted STV was washed out with 0.15 M PBS, and then the flow channel was filled with 0.025 M PBS. Next, 2 µM of I-PNP and 15 µM of M-PNP probes were introduced and reacted for 10 min. Unbound PNPs were removed and unreacted STV binding sites were quenched by washing with 0.025 M PBS containing 1 µM of free biotins. After 15 min, the buffer was exchanged to 0.15 M PBS. Typically, this procedure resulted in SLB-tethered I-PNP and M-PNP at a ratio of 1:3.

4.1. Control and Quantification of Biotin Valency Per Gold Nanoparticle

First, the present inventors controlled the diffusion of the lipid-tethered plasmonic nanoparticles (PNPs) by changing the biotin valency of PNPs. From this, it was ascertained that the number of ligands per particle has a significant effect on the lateral mobility of nanoparticles on a lipid membrane. The present inventors adjusted the valency of the biotin molecules on AuNPs during the DNA functionalization step by varying the molar ratios between the target capture DNA sequence and the SLB tethering DNA sequence. This stoichiometric control method yielded highly reproducible results. The number of SLB tethering sequences per PNP was estimated by measuring the fluorescence emission intensity of Cy3 molecules that were modified to SLB tethering sequences after dissolving AuNPs with a KCN solution. The average biotin valency increased linearly from 0.57 to 128 as the added amount of SLB tethering DNA linker increased (refer to FIG. 1 and Table 1). The prepared PNP probes were tethered to the SLB surface through biotin-streptavidin interactions. The PNP probes on a SLB with a biotin valency of 0.57 were considered to have had one biotin because biotin-free PNPs could not bind to the SLB and could be completely washed out from the surface.

TABLE 1

| Mole fraction of SLB tethering sequence (total concentration: 4 µM) | Average biotin valency of PNPs |
| --- | --- |
| 0.00125 | 0.569 ± 0.08 (~1 for tethered PNP) |
| 0.0025 | 4.660 ± 0.564 |
| 0.0125 | 28.297 ± 1.850 |
| 0.0625 | 127.78 ± 1.351 |
| 0.3125 | 486.46 ± 8.008 |

4.2. Effects of Biotin Valency on Diffusion Kinetics of PNP Probes on SLB

Figure 4A:
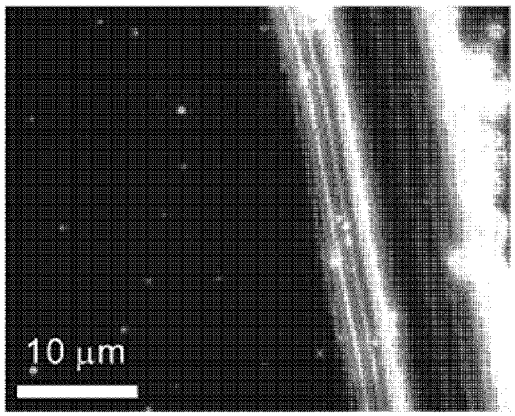
FIGS. 4A and 4B shows photographs illustrating the images of PNP probes on the SLB.
Figure 4B:
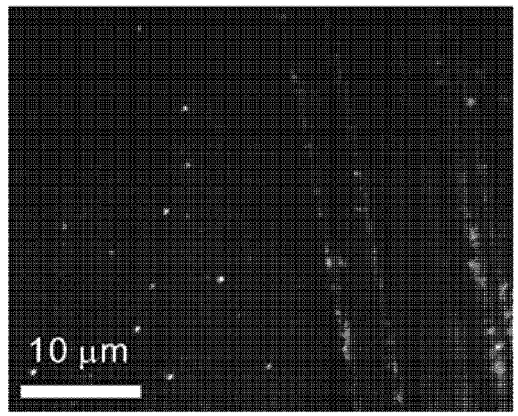

The lateral motions of SLB-tethered PNP probes were observed with a single-nanoparticle resolution using the dark-field microscopy, and their individual trajectories were analyzed by an image analysis program (ImageJ software; detailed experiments and analysis methods will be described later). The mean square displacement (MSD) values as a function of time of the SLB-tethered PNP probes with different biotin valencies are shown in FIG. 2A. Multivalent PNPs showed a tendency to diffuse much more slowly and travel a shorter distance as compared to paucivalent PNPs. The PNP with 486 biotins was nearly immobile and stayed in almost the same position. The MSD plots of these trajectories, except for the case of including 486 biotins, clearly exhibit the linear relationships between the MSD and time interval, suggesting that these nanoparticles are in random 2D Brownian motion on the SLB surface. In order to calculate the diffusion coefficients of the PNP probes, the present inventors analyzed 100 particle trajectories for each biotin valency and the corresponding MSD plots were fitted to the following equation: $<r^2>=4Dt$, where $<r>$ is the MSD, D is the diffusion coefficient, and t is the time interval. The average value of the diffusion coefficients was estimated to 1.79±0.87×10$^{-8}$, 0.72±0.35×10$^{-8}$, 0.38±0.29×10$^{-8}$, and 0.18±0.14×10$^{-8}$ cm$^2$/s for biotin valencies of 1, 5, 28, and 128, respectively (FIG. 2B). The distributions of calculated D values were plotted in FIGS. 3A to 3D, and these values are consistent with other literature results where SLBs were modified with AuNPs of 30 to 50 nm for the visualization of lipid motion. As PNPs became more multivalent, the mobile fraction was more reduced, and most particles were virtually immobile when the biotin valency reached 486. The present inventors observed and correlated a dark-field microscope image of multivalent PNPs and a fluorescence microscope image of Cy3-modified STVs on the SLB to prove the position of PNPs matches with the position of locally concentrated STVs. The results show that the two images are well matched to each other, suggesting that local accumulation of STVs under the multivalent PNP is responsible for the loss of particle mobility (FIGS. 4A and 4B).

4.3 Optical Stability Test of Gold Nanoparticles

The resonant light scattering of metal nanoparticles has a different physical origin than the fluorescence of organic dyes. The radiative damping of localized surface plasmon creates scattered photons, and this process is free of blinking and photobleaching. In order to evaluate photostability of PNPs, the 50 nm AuNPs on the SLB were continuously exposed to dark-field microscopy illumination for 30 min and the scattering intensity was recorded every 6 s (FIGS. 5A to 5D). The particles continued shining without change in the intensity over the whole experimental time. This indicates that the AuNPs are more robust optical labels for real-time optical study than fluorescence dyes that substantially lose their signals within a few minutes even when multiple dyes are employed for single-particle tracking.

Figures 7A, 7B, 7C:
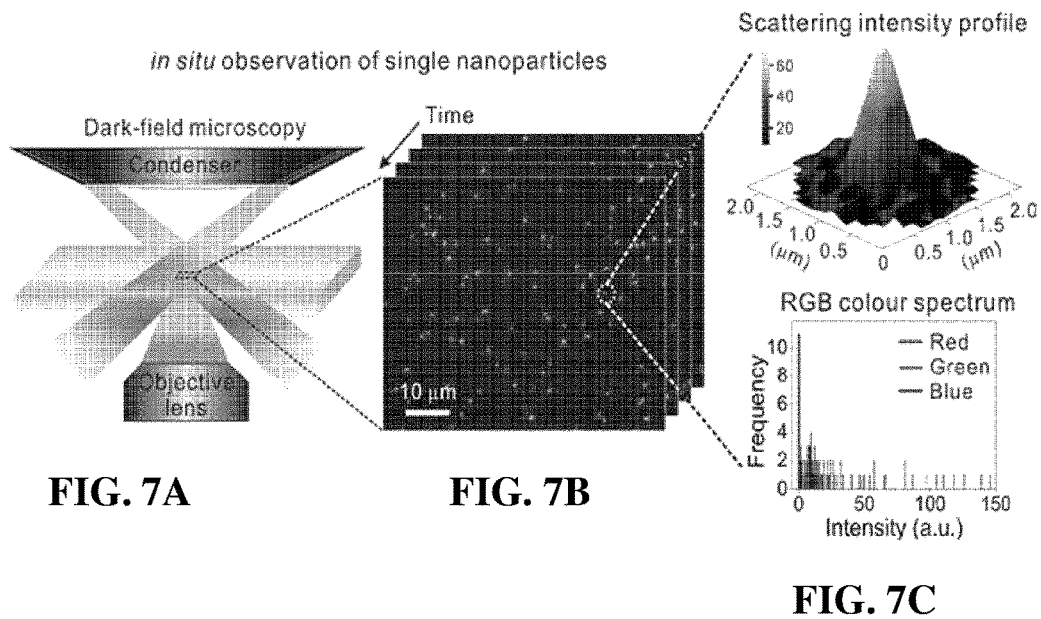
FIGS. 7A to 7C are schematic views illustrating the single-nanoparticle-resolution in situ imaging and analysis of nanoparticles dynamically tethered on the SLB.

4.4. Single-Nanoparticle-Resolution In Situ Imaging and Analysis of Nanoparticles Tethered on SLB PNPs are dynamically tethered to a fluidic SLB, and the dynamic behavior of PNP was adjusted by controlling the valency of particles. Then, the in situ DNA hybridization-induced particle duster growth dynamics were analyzed with single-particle-level resolution, and the quantitative analysis on this platform was performed using real-time plasmonic coupling between interacting PNPs (FIGS. 6 and 7). The interactions from multiple particle reaction sites were simultaneously monitored and analyzed, the kinetic studies for the formation of dimeric, trimeric, and tetrameric nanoparticle dusters were performed, and a multi-parallel single-particle-analysis-based DNA detection assay was shown as an application of this method. PNPs are used in this approach because they efficiently scatter resonant light and are insusceptible to photobleaching and blinking, which enables single-nanoparticle tracking over a long period with a good spatio-temporal resolution (over 1 h with ~1.5 nm and ~10 µs resolution). Importantly, the plasmons of individual gold or silver nanoparticles (AuNPs or AgNPs) interact with each other in a distance-dependent manner, and this forms a basic principle that underlies the measurements of molecular interactions within several tens of nanometers by monitoring change in scattering intensity or spectral response without further labeling. SLB is a very powerful platform as it allows for synthesizing and controlling a 2D fluidic surface on solid substrates and incorporating a variety of membrane species with lateral mobility. By tethering nanoparticles to the SLB, one could confine nanoparticles in the 2D focal plane of the optical microscopy for the efficient imaging and tracking of all of the nanoparticles of interest while preserving the free motions of nanoparticles due to the fluidic nature of the SLB. As tethered PNPs resonantly scatter the incident light and always travel on the planar lipid bilayer surface, 2D diffusion trajectories and optical signals can be recorded in situ using the dark-field microscopy setup (Axiovert 200M, Carl Zeiss, Göttingen, Germany) with single-particle resolution (refer to FIGS. 7A to 7C). The dark-field results proved that tethered PNPs were uniformly dispersed throughout the 2D membrane surface and showed the excellent lateral mobility with free diffusion over the membrane surface. This dynamic 2D confinement of particles and the use of PNP labels allow for facilitating efficient collisions between particles and in situ observation and analysis of nearly all of the reactions between the molecules on nanoparticles.

Example 5: Preparation of Patterned SLB

For DNA assay, SLB of 120×120 μm² was formed in a patterned gold film on a glass substrate. A gold pattern was formed by conventional photolithography and a conventional lift-off process. The SLB could be selectively deposited onto the glass surface exposed by the introduction of an SUV solution because the surface of gold is inert to the formation of SLB. After the formation of SLB, the surface of gold was passivated with 2 mg/ml BSA and 10 μm carboxymethyl polyethylene glycol dissolved in PBS in order to suppress the nonspecific binding of PNPs and target DNA. Then, PNPs were tethered for the use of DNA assay experiments.

Example 6: Dark-Field Microscopy-Based in Situ Observation of PNP Probes and Optical Analysis Thereof The movement and plasmonic coupling of SLB-tethered PNP probes were observed by the dark-field microscopy (Axiovert 200M, Carl Zeiss, Göttingen, Germany) provided with a 40× objective lens (NA 0.6). All of the image analysis procedures were conducted with ImageJ software (http://rsb.info.nih.gov/ij/). For tracking and trajectory analysis of individual SLB-tethered PNP probes, the MOSAIC plugin was used (http://www.mosaic.ethz.ch/Downloads/ParticleTracker). The scattering intensity and RGB color spectra were measured by basic intensity measurement and RGB color intensity splitting functions of ImageJ software, respectively. Cy3-modified STV was observed by epifluorescence microscopy (TE-2000, Nikon, Tokyo, Japan) provided with a 60× lens (NA 1.49) under 532 nm laser excitation.

6.1. High-Resolution Imaging Assay of Interacting Particles

Figures 8A, 8B, 8C:
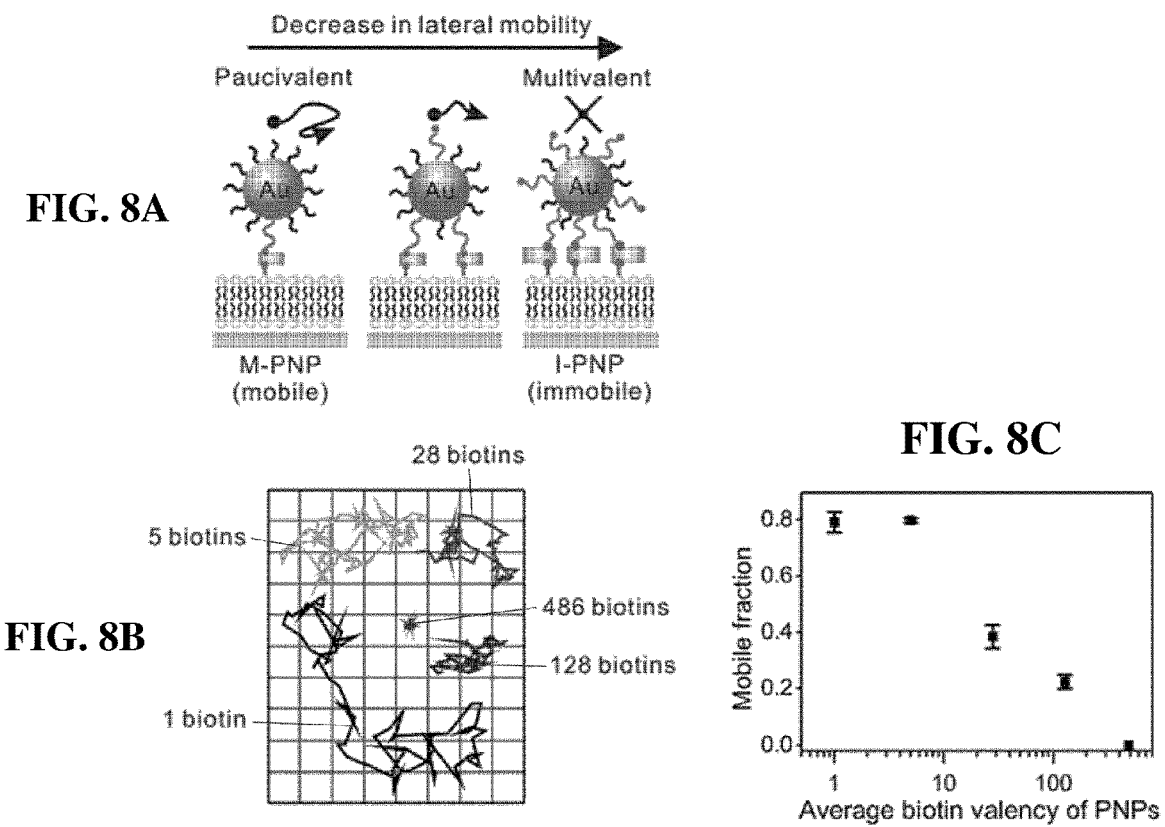
FIGS. 8A to 8C shows the results of control of diffusive dynamics and optical analysis of interacting plasmonic nanoparticles on the SLB.

Another important aspect of high-resolution imaging assay is a stable and reliable observation method of interacting particles. In order to facilitate this, two types of DNA-modified plasmonic nanoparticles (DNA-PNPs) with significant difference in lateral mobility were designed, prepared and tethered to the SLB surface, highly mobile and nearly immobile PNP (M-PNP and I-PNP) probes, respectively (refer to FIG. 6). The scattering signal from a fixed I-PNP site was stably monitored and analyzed, and M-PNPs were diffused into an I-PNP site to induce change in the plasmonic coupling-based scattering signal. I—PNP and M-PNP probes were separately prepared with 5'-thiol-modified DNA and 3'-thiol-modified DNA, respectively. Two different thiolated DNA sequences (target capture sequence and SLB tethering sequence) were used for the functionalization of each PNP probe. The SLB tethering sequence possesses a biotin group on the end opposite to thiol, and forms stable bonding to streptavidin-modified SLB. The mobility of PNP probes was controlled by the biotin valency of a probe with a different mole fraction of the SLB tethering sequence in the DNA modification procedure. As PNPs became more multivalent, diffusion coefficients and mobile fractions were further reduced, and all particles were virtually immobile when the biotin valency reached 486, which is obtained with a 0.15625 mole fraction of the SLB tethering sequence (refer to FIGS. 8A to 8C). For M-PNP probes, here, a 0.00125 mole fraction of the SLB tethering sequence was added to yield 1 biotin valency. The M-PNP probe is paucivalent and can much more freely diffuse via random 2D Brownian motion. On the other hand, multivalent I-PNP probes are almost completely immobilized on the membrane surface. The scattering intensity was analyzed with ImageJ software by averaging an I-PNP site-centered circular area with a radius of 500 nm, which is similar to the optical resolution, d, of the microscopy setup that was used in this study (d=λ/2NA; λ is the resonant scattering wavelength of 50 nm AuNPs, 530 nm; NA is the numerical aperture of a 40× objective lens, 0.6).

As M-PNP and I-PNP probes were tethered to biotinylated lipids in the SLB via streptavidin linkers, the local position and movement of the PNP-conjugated lipids could be readily tracked with a resonant light scattering signal in the dark-field microscopy. In the absence of particle-linking target DNA, M-PNP probes can approach a fixed I-PNP site and these probes could be temporarily overlapped in the dark-field microscopy. Consequently, the scattering intensity of an I-PNP site was initially constant but fluctuated as an M-PNP came within the optical diffraction limit (refer to FIGS. 9A and 9B). Interestingly, two kinds of transient sharp rises in the signal were observed. In one case, which was more frequent, the scattering intensity was about twice as high as the initial value. This can be attributed to the distant optical overlapping, where two PNPs reside within the optical resolution but are not sufficiently close to each other to cause plasmonic coupling (FIG. 9B-i). In the other case, an about 3.5-fold rise in the scattering intensity was observed, and this high enhancement originated from the near-field interaction between two plasmonically coupled PNPs (FIG. 9B-ii). It should be noted that most of these signal changes lasted for less than 0.5 s due to the absence of specific interactions between particles. Temporary intermolecular proximity between lipids was discerned at a sub-diffraction length scale by plasmonic coupling. Our strategy and results suggest that one can monitor intermolecular interactions which cause the docking and plasmonic coupling between PNP probes. In the next set of experiments, we observed in situ DNA hybridization and dehybridization events that triggered the assembly and disassembly of the DNA-modified PNP probes on the SLB and recorded the corresponding change in the scattering intensity at a single-nanoparticle resolution in real time. In the presence of the target DNA sequence, paucivalent M-PNPs were captured by a multivalent I-PNP and formed a multi-particle cluster wherein an I-PNP was fixed and monitored as a tracking center. In the dark-field microscopic image, the assembly process was successfully resolved for observing single-nanoparticle addition events. Particle-by-particle PNP cluster growths from monomer to tetramer were observed and the trajectories of M-PNP probes that have been captured are highlighted with white solid lines (refer to FIG. 10A). As the clusters evolved, we observed sudden change in both the scattering intensity and color in every single M-PNP addition step to an I-PNP site. Changes in the scattering efficiency and resonance wavelength arose from the plasmonic coupling in the clustered AuNPs. At 3 nM target DNA concentration, the reaction was finished within 15 min and many monomeric M-PNP probes were consumed to form the dusters. The duster growth was usually restricted within a tetramer and further growth beyond a tetramer was hardly observed, because there is a limited number of M-PNPs and also large steric hindrance between DNA strands on particles for the assembly of more than 4 particles in a single site on a 2D surface in this case. The utilization of fixed I-PNPs restricts a duster growth pathway to monomer attachment by effectively eliminating coalescence between small clusters that produces irregular 2D aggregates and impairs the quantitativity (please refer to supplementary FIGS. 11A to 11D for the coalescence process observed in an M-PNP pair-modified SLB). The plasmonic coupling between PNP probes caused a red-shift in a resonance wavelength and thus the plasmonically coupled green AuNPs turned red in the dark-field microscopic image. The plasmonic color change was analyzed by splitting RGB channels (FIGS. 7A to 7C). As the duster grew, green and red signals were increased while blue signal remained constant. Based on these results, we plotted a green-to-red ratio graph and a linear increase in the ratio was observed as the number of clustered particles increased (FIG. 10B). The color calibration standard should be practically useful to accurately define and quantify the state of interparticle interactions and to differentiate specific interaction-based plasmonic couplings from nonspecific optical overlaps. Importantly, the particle-by-particle addition of M-PNP probes to an I-PNP site via target DNA recognition and hybridization was shown and quantified in the time trace of the scattering intensity (top graph in FIG. 10C). The results show that the scattering signal intensity was increased in a stepwise manner when each M-PNP was added to an I-PNP probe to sequentially form a dimer, a trimer, and a tetramer. When a high-salt PBS solution (167 mM Na$^+$) was replaced with a low-salt PB solution that contained much less salt (17 mM Na$^+$) target DNA was dehybridized and M-PNPs were dissociated from I-PNP probes and freely diffused over the SLB surface again, which gave rise to a series of stepwise decreases in the scattering intensity (bottom graph in FIG. 10C). It should be noted that the scattering signal intensity underwent multiple stepwise changes for every probe addition step and remained constant until the next particle was added or freed.

6.2. Analysis of Duster Growth Kinetics

The duster growth kinetics from monomer to tetramer were fitted to the three-step first-order consecutive reactions by assuming M-PNPs are present in excess compared to I-PNPs:

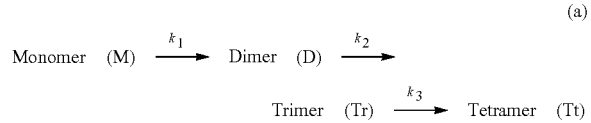

(a)

The differential forms for the rates of change of each species are as follows.

$$\frac{d[M]}{dt} = -k_1[M] \tag{b}$$

$$\frac{d[D]}{dt} = k_1[M] - k_2[D] \tag{c}$$

$$\frac{d[Tr]}{dt} = k_2[D] - k_3[Tr] \tag{d}$$

$$\frac{d[Tt]}{dt} = k_3[Tr] \tag{e}$$

Solving these differential equations yields solutions to describe time-dependent concentrations of each species:

$$[M] = [M]_0 e^{-k_1 t} \tag{f}$$

$$[D] = \frac{k_1 [M]_0}{k_2 - k_1}(e^{-k_1 t} - e^{-k_2 t}) \tag{g}$$

$$[Tr] = -\frac{k_1 k_2 [M]_0}{(k_1 - k_2)(k_3 - k_1)} e^{-k_1 t} - \frac{k_1 k_2 [M]_0}{(k_1 - k_2)(k_2 - k_3)} e^{-k_2 t} - \frac{k_1 k_2 [M]_0}{(k_2 - k_3)(k_3 - k_1)} e^{-k_3 t} \tag{h}$$

$$[Tt] = [M]_0 + \frac{k_2 k_3 [M]_0}{(k_1 - k_2)(k_3 - k_1)} e^{-k_1 t} + \frac{k_1 k_3 [M]_0}{(k_1 - k_2)(k_2 - k_3)} e^{-k_2 t} + \frac{k_1 k_2 [M]_0}{(k_2 - k_3)(k_3 - k_1)} e^{-k_3 t} \tag{i}$$

Where an initial I-PNP monomer concentration $[M]_0$ is 150, which is the number of particles analyzed here. The rate constant values of $k_1$, $k_2$, and $k_3$ were evaluated by fitting kinetic data using these equations.

Figure 14:
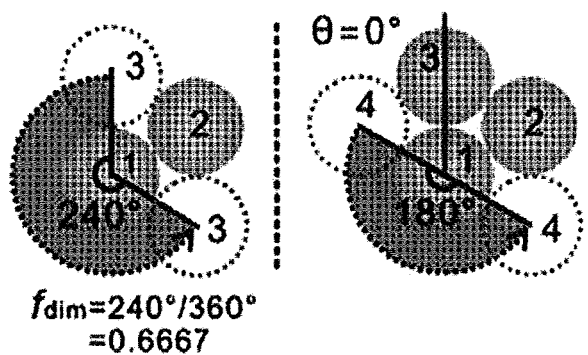
FIG. 14 shows the calculation method of 2D steric hindrance factors for the sequential addition of a plasmonic probe to a dimer to form a trimer or to a trimer to form a tetramer. The gray regions represent the possible approach angle for the next particle addition. In the tetramer formation, the steric hindrance factor is plotted as function of θ, determined by a relative position of the third particle (black solid line in the inset graph). The average ftri is 0.375 (red dashed line).
Figure 14:
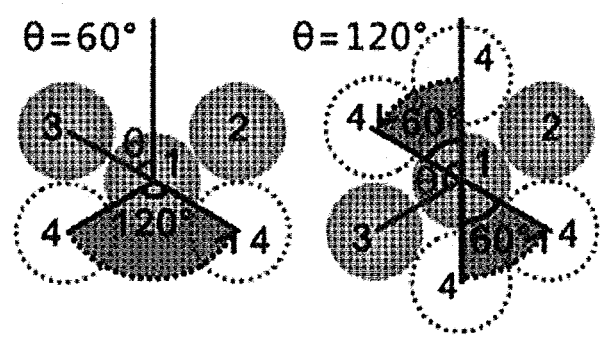
Figure 14:
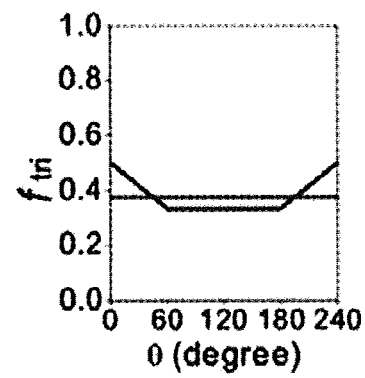

The highly parallel in situ observations of multiple interactions were realized by the simultaneous analysis of individual plasmonic coupling of PNP probes over a large surface area (typically ~30,000 μm$^2$; FIG. 12A). The in situ parallel particle cluster growth analysis results for a 330 s observation time (80 ms exposure time and 1 s time interval) according to the present invention show that, although a sequential particle-by-particle cluster growth was typically observed (FIGS. 12B-i and iv), many different clustering modes were also observed with different clustering kinetics. Some probes formed only dimers and did not grow further (FIGS. 12B-ii and iii). There is also a case in which the probe cluster grew to form a trimer without growing further to form a tetramer. Interestingly, the simultaneous addition of two probes to an I-PNP probe (FIGS. 12B-iii and vi) and back-to-back additions of two or three probes to an I-PNP probe within a very short time frame were also observed and resolved (FIGS. 12B-vii, ix, and x; please refer to the inset graphs for these cases). In the present invention, based on this in situ parallel single-particle resolution analysis capability, DNA-hybridization-induced cluster-forming reaction kinetics were studied. The scattering intensities of 150 individual I-PNP sites were simultaneously monitored for this purpose. The growth kinetics from a monomer to a tetramer (monomer-dimer-trimer-tetramer) were fitted to a three-step consecutive reaction by assuming that M-PNPs were present in excess compared to I-PNP monomers. The rate constants for dimer, trimer, and tetramer formations were estimated to be k1=0.0165, k2=0.0116, and k3=0.0061 s$^{-1}$, respectively. This model explains the nanoparticle cluster growth kinetics within 180 s. This result is direct evidence for the assumption that forming a trimer from a dimer is a more difficult and slower process than forming a dimer from a monomer, and tetramer formation is the most difficult and time-consuming process due to the steric hindrance between DNA-modified PNP probes. When the steric hindrance factor (f) is taken into account, the rate constants for trimer and tetramer formations can be expressed as $k_2=f_{dim}k_1$ and $k_3=f_{tri}k_1$, respectively. The steric factors were calculated from the fitted rate constants (0.7030 for $f_{dim}$ and 0.3697 for $f_{tri}$). Transmission electron microscopy measurement shows PNP clusters are formed into different geometric configurations (FIGS. 13A and 13B). Based on this observation, the present inventors geometrically calculated steric factors for the addition of the next PNP to a 2D dimer and a 2D trimer (geometrically calculated steric hindrance factors: $f_{dim}=0.6667$ and $f_{tri}=0.3750$; FIG. 14). These values are consistent with steric factors obtained from fitted rate constants, suggesting that the three-step consecutive reaction model describes and explains the 2D cluster growth of DNA-modified PNP probes.

Finally, the present inventors drew the optical calibration standards for the number of reacted particles in the clusters, and based on this standard curve, they performed target DNA detection and evaluated detection sensitivity of the PNP-tethered SLB platform. The calibration standard plots were obtained by analyzing 30 individual clusters simultaneously, and the number of particles in the clusters was confirmed by resolving and recording particle addition events in full. In order to avoid simultaneous addition of multiple PNP probes within a single frame acquisition, the frame rate was elevated by 5.3 frames per second in this case. The present inventors plotted the averaged scattering intensities and found a linear relationship with the number of clustered particles ($R^2$ value is 0.999, FIG. 15A). The corresponding distributions are shown in FIGS. 5A to 5D. Notably, the results exhibited narrow standard deviations, and the present inventors can clearly distinguish the clustered states.

6.3. Target DNA Detection Limit Using Interaction with Complementary DNA-Modified PNPs Tethered to SLB The gold nanoparticle cluster formed by the interaction of target DNA and complementary sequence thereof can be used as a biosensor for detecting DNA in the case of quantifying the degree of cluster formation, because the intensity of scattering signals of the gold nanoparticle cluster is clearly increased and this gold nanoparticle cluster can be observed at a single-nanoparticle level. Therefore, since the gold nanoparticle cluster is formed depending on the concentration of target DNA, the detectable concentration range of target DNA was determined by analyzing the brightness of dark-field microscope images. The DNA detection was performed on a 120×120 $\mu m^2$ SLB pattern embedded in a gold film (FIG. 15B). PNP-modified SLBs were reacted for 4 h with different concentrations of target DNA ranging from 300 aM to 300 fM. All of the samples, including the control sample, contained 300 fM of a non-complementary DNA sequence to validate the assay selectivity according to the present invention. PNPs formed only a dimer without further growth to a trimer and a tetramer in the concentration range of target DNA used in the present invention. I-PNP sites representing coupled dimer scattering intensity (>3.5-fold enhancement; refer to FIG. 15A) were counted only as an optical signal for a target DNA sequence (FIG. 15B). Assay results show the limit of detection of 30 fM without optimization processes (FIG. 15C). Notably, a single-base-pair-mismatched DNA sequence was also clearly discriminated (FIG. 15C).

Through the optimization procedures of the assay, the present inventors intended to decrease the detection limit and increase the sensitivity. Thus, it was found that ultralow-concentration target DNA of 47, 95, 950, and 9500 strands was quantified, and as a result, target DNA having a very small number of 95, 950, and 9500 strands can also be clearly discriminated from single-base-pair-mismatched DNA. Specifically, for this purpose, the volume of sample was reduced to 1 µL to 3.5 µL by using a small sticker chamber having a radius of 1 mm to block the random diffusion of target materials, so as to exhibit the effect of concentrating the sample (FIG. 16A). Thus, PNPs were specifically bonded to only the 120×120 $\mu m^2$ SLB pattern embedded in a chrome film, thereby improving the efficiency of detection (FIGS. 16B and 16C).

Moreover, the repetitive conversion of target DNA hybridization-induced plasmonic nanoparticle cluster into monomers and dimmers through the assembly and disassembly procedures of the cluster over time was confirmed from the trend of scattering intensity change over time (FIG. 17A). This result indicates that a primary dynamic reaction is accompanied within a system as well as by a change in an external condition. The lower end of FIG. 17A shows the dissociation events over dissociation time, where the dissociation procedure is performed at a dissociation rate of about 78±5%. Meanwhile, it was found in FIG. 17B that valences are measured from all images measured within an observation time defined by an imaging time interval Δt in consideration of the dissociation time in the target DNA hybridization-induced plasmonic nanoparticle cluster system repeating assembly and disassembly, and cumulative valences are calculated, thereby enabling data analysis without loss (dynamic analysis, lower end of FIG. 17B). Unlike this dynamic analysis, in the conventional analysis, where valences are determined by analyzing only first and final images in the observation time, it was found that some data is lost, and thus this conventional analysis is disadvantageous for more sensitive detection (conventional analysis, upper end of FIG. 17B).

Meanwhile, FIGS. 18A and 18B show the comparison of analysis results of data using the dynamic analysis of the present invention with those of data using the conventional analysis, with respect to different ultralow-concentration samples (47, 95, 950, and 9500 DNA strands) and observation time (1, 2, and 4 hours). In the dynamic analysis of the present invention, an image analysis time interval is set in consideration of average dissociation time and minimum dissociation time. As shown in FIGS. 18A and 18B, when the dynamic analysis is used, it was found that as the observation increases, the difference in concentration becomes remarkable, and thus qualitative analysis is possible. FIG. 19A shows the selectivity between an analyte containing ultralow-concentration target DNA (95, 950, and 9500 DNA strands) and single-base-mismatched DNA, and shows that single-base-mismatched DNA can be distinguished with high resolution by the detection method of the present invention. Moreover, it was found in FIG. 19B that detection was attempted using the sample prepared by spiking target DNA of 95 strands into 1% human serum in order to provide conditions similar to those of human blood, and that the trend of cumulative valences in the experimental group containing a target material and the control group not containing the target material is completely distinguished. From the above results, it can be ascertained that a trace of DNA can also be detected by the combination of the detection method of the present invention and the dynamic analysis method of the present invention.

Such high sensitivity means that M-PNPs mobile on the SLB and I-PNPs immobile on the SLB are moved and reacted on the two-dimensional plane, and thus collision probability increases so as to cause a rapid reaction. In reality, it was observed that a very slow and inefficient reaction was caused when the M-PNPs were dispersed in a solution without being introduced into a supported lipid bilayer (SLB) and were reacted with the I-PNPs fixed on the SLB.

Figure 20:
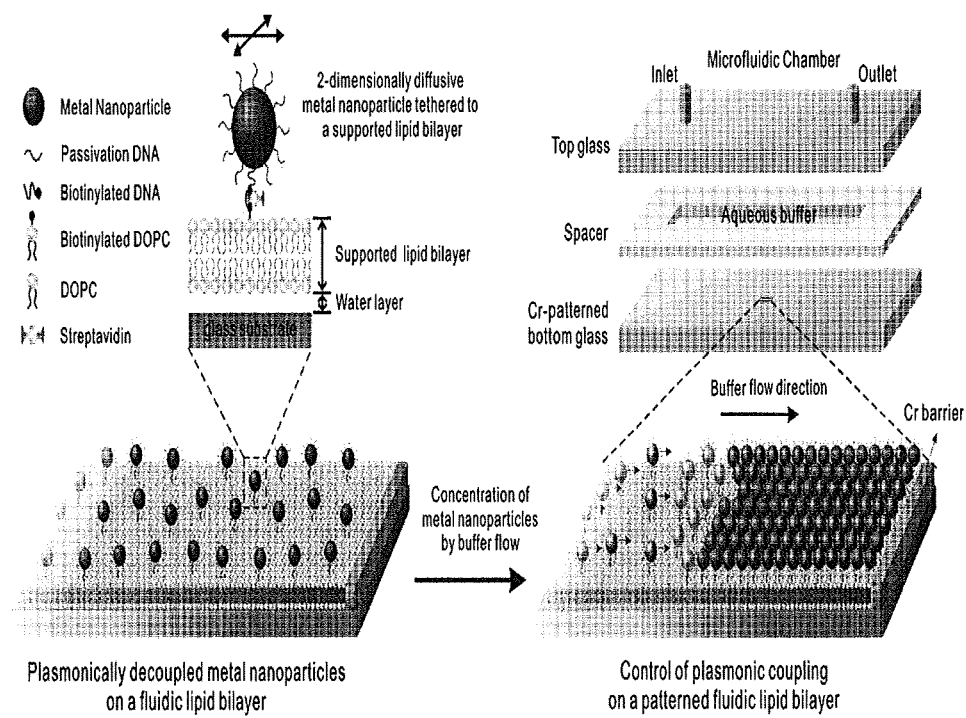
FIG. 20 is a schematic view showing a method of controlling the interactions between nanoparticles by adjusting the mobility of metal nanoparticles on the patterned SLB using a fluid.

6.4. Adjustment of Distribution of Nanoparticles Tethered to SLB by External Stimuli and Induction of Plasmonic Coupling When the biotin valency of metal nanoparticles tethered on SLB is appropriately adjusted, the metal nanoparticles have fluidity on the SLB. The fluidic metal nanoparticles conduct a free two-dimensional diffusion movement, and can be adjusted such that they are moved on the SLB in a desired direction by external stimuli (for example, electric field and fluid flow). In this case, the moving speed of the metal nanoparticles can also be adjusted by changing electric field intensity or flow rate. As shown in FIG. 20, when the spatial distribution of nanoparticles is adjusted in the patterned SLB, the density of the nanoparticles in a specific portion can be increased, and the collision frequency between the nanoparticles can be greatly improved. Therefore, when the interaction between the nanoparticles is increased on the SLB, reaction rate is increased, and thus the sensitivity of a biosensor is improved so as to shorten detection time. Further, the distance between the nanoparticles is adjusted so as to form a platform for adjusting plasmonic coupling.

Figure 22:
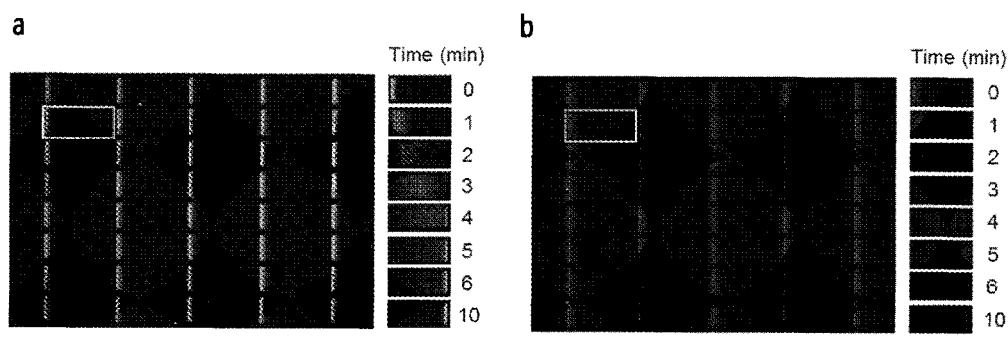
FIGS. 22 A and 22B show the mobility of nanoparticles formed on the SLB.

Specifically, in order to adjust the movement of the metal nanoparticles introduced in the SLM platform, a flow channel is provided on a glass substrate. Holes are formed in both sides of an upper slide glass to introduce a buffer solution for forming a fluid flow. When the fluid flow is introduced in the flow channel in this way, the metal nanoparticles move in a specific direction during the free two-dimensional diffusion movement while gradually changing the mute of movement. As flow rate increased, such a movement tendency was observed dearly (FIGS. 21A and 21B). In the case where the SLB is patterned with chromium (Cr), the metal nanoparticles are confined in a Cr barrier without going out of the Cr barrier (bottom right of FIG. 20). In this case, when the direction of movement of the metal nanoparticles is adjusted in one direction by a fluid flow, a phenomenon in which the metal nanoparticles move in the same direction as the fluid flow to be concentrated can be observed (FIGS. 22A and 22B). It was found that both gold nanoparticles and silver nanoparticles are accumulated in one direction to exhibit colors of specific surface plasmon resonance wavelengths. Further, it was observed that, when the fluid flow is changed in the opposition direction, the accumulated metal nanoparticles move in the opposite direction to be concentrated.

Figure 23:
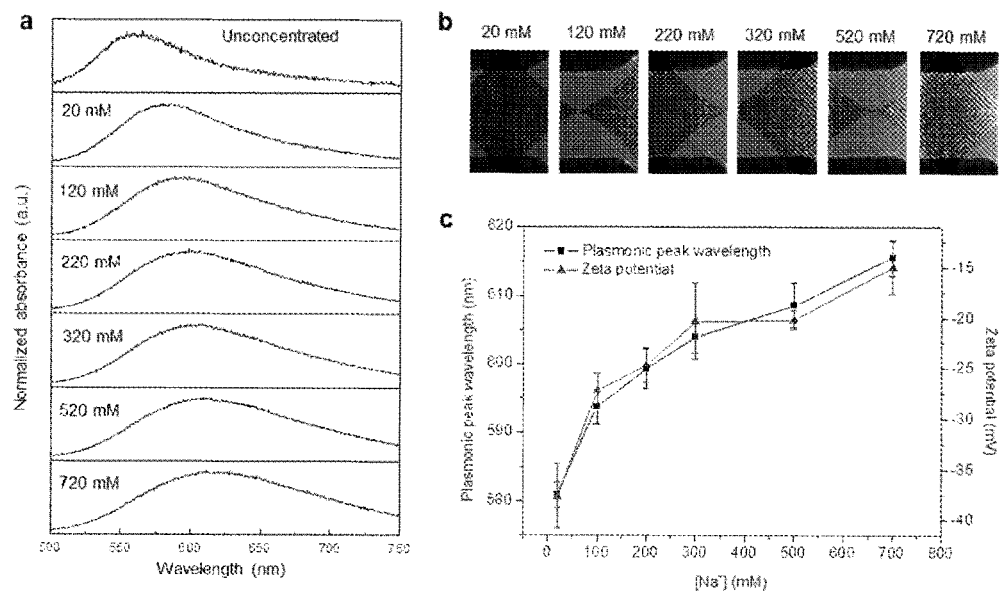
FIGS. 23A to 23C show the change in the scattering spectra of metal nanoparticles concentrated on the SLB patterned with gold nanoparticles by a fluid flow.

When the SLB pattern is fabricated to a large size of several square millimeters (mm$^2$), a larger number of metal nanoparticles can be accumulated in one place. In order to accumulate a larger number of metal nanoparticles, a trapezoidal pattern was fabricated, and metal nanoparticles were concentrated at a flow rate of 6 ml/h for about 30 min. It was found that the concentrated metal nanoparticles have specific plasmonic scattering colors at ends of the trapezoidal pattern. In this case, the metal nanoparticles maintain an equilibrium by fluid flow force, Van der Waals interactions between DNA-modified nanoparticles, steric repulsion between DNA molecules, and electrostatic repulsion. In order to reduce the distance between metal nanoparticles, in this study, the concentration of NaCl contained in the fluid was increased. It was found that, with the increase in the concentration of NaCl, the electrostatic repulsion between the metal nanoparticles is decreased, and thus the distance between the metal nanoparticles becomes closer so as to induce plasmonic coupling. The scattering spectra at this time were measured and analyzed (FIGS. 23A, 23B, 24A, and 24B). The maximum peak of the scattering spectra represents red shift with the increase in the concentration of a salt. From the results of measurement of zeta potential of metal nanoparticles, it was found that the surface charge of the metal nanoparticles decreases with the increase in the concentration of a salt, and thus the electrostatic repulsion between the metal nanoparticles decreases so as to decrease the distance therebetween (FIGS. 23C and 24C).

6.5. Development of Biomimetic Artificial Membrane Platform

The cell membrane, which is a structure separating the inside and outside of a cell, is a thin phospholipid bilayer composed of phospholipid and protein molecules. The cell membrane has selective permeability, and functions to maintain cell functions and cell tissues through various proteins. Like this, various biological phenomena for maintaining the homeostasis and essential functions of cells occur in the cell membrane. Therefore, biological and cytological understandings of the cell membrane are very important.

From this viewpoint, the behaviors of cells can be observed by using the SLB platform disclosed in Example 6.4., which is an electrically or hydrodynamically adjustable artificial cell membrane structure. A marker material, such as metal nanoparticles, including a biomaterial is introduced into the SLB, which is an artificial membrane, by using a chemical or biological method, and the optical properties of the marker material are detected, thereby monitoring the behavior of cells. The biomaterial introduced into the SLB can induce signal transfer intracellularly or can induce a phenotype modulation reaction extracellularly. Such observation can help to identify new biological mechanisms not yet disclosed in that it is similar to a biological reaction occurring in the real cell membrane.

Metal nanoparticles having optical properties, such as plasmon resonance, may be hybridized depending on the distance between the metal nanoparticle and adjacent metal particles. Due to such characteristics, these metal nanoparticles exhibit different colors depending on the distance between the metal nanoparticle and adjacent metal particles and the clustering degree of the metal nanoparticles at the time of observation with a dark-field microscope. Further, the metal nanoparticles can be observed at a high signal-to-noise ratio (S/N ratio) for a period of time due to strong plasmonic scattering. Cell responses can be observed by introducing cell monitoring probes generating multiply-detectable surface-enhanced Raman scattering signals as well as plasmonic scattering signals into a cell membrane.

Therefore, the metal nanoparticles including biomaterials are introduced into the surface of SLM, cells are cultured, and the movement of the metal nanoparticles due to the cells can then be optically analyzed. Accordingly, cell signal transfer mechanisms can be more precisely analyzed in that the behavior of cells can be observed in real time and the interactions between cells and biomaterials can be monitored at the nanoscale in real time (FIG. 25).

Example 7: Multiple Detection Using Three-Color (Red/Green/Blue (RGB)) Nanoprobes Noble metal nanoparticles, such as silver nanoparticles and gold nanoparticles, are characterized in that they exhibit a variety of colors depending on the shape and/or size thereof because they cause plasmonic resonance. Due to these characteristics, nanoparticles emitting red, blue, or green light can be provided by changing the composition, shape, and/or size thereof since these nanoparticles exhibit different colors from one another, they can be distinguished from one another by a dark-field microscope. Therefore, the applicability of these different three-color nanoparticles to the multiple detection of miRNA was found by enabling the distinction between different combinations. Meanwhile, since miRNA, which is a short RNA strand controlling the in vivo function, is known to be incorrectly expressed in patients having diseases such as cancers, it may serve as a biomarker for diagnosing diseases such as cancers. Examples of incorrectly expressed miRNA found in various cancers are shown in Table 2 below.

TABLE 2

|  | Lung | Breast | Colon | Pancreas | Prostate | Stomach |
|---|---|---|---|---|---|---|
| miR-21 | + | + | + | + | + | + |
| miR-25 |  |  |  | + | + | + |
| miR-125b | + |  |  | + |  | + |
| miR-141 | + | + | + |  | + |  |
| miR-146a |  | + |  |  | + | + |
| miR-155 | + | + | + |  |  |  |
| miR-191 | + |  | + | + | + | + |
| miR-205 | + |  |  |  |  |  |
| miR-221 |  |  | + | + | + | + |

+ indicates the presence of incorrectly expressed miRNA found in various cancers.

7.1. Preparation of Three-Color (RGB) Nanoparticles

Figure 26:
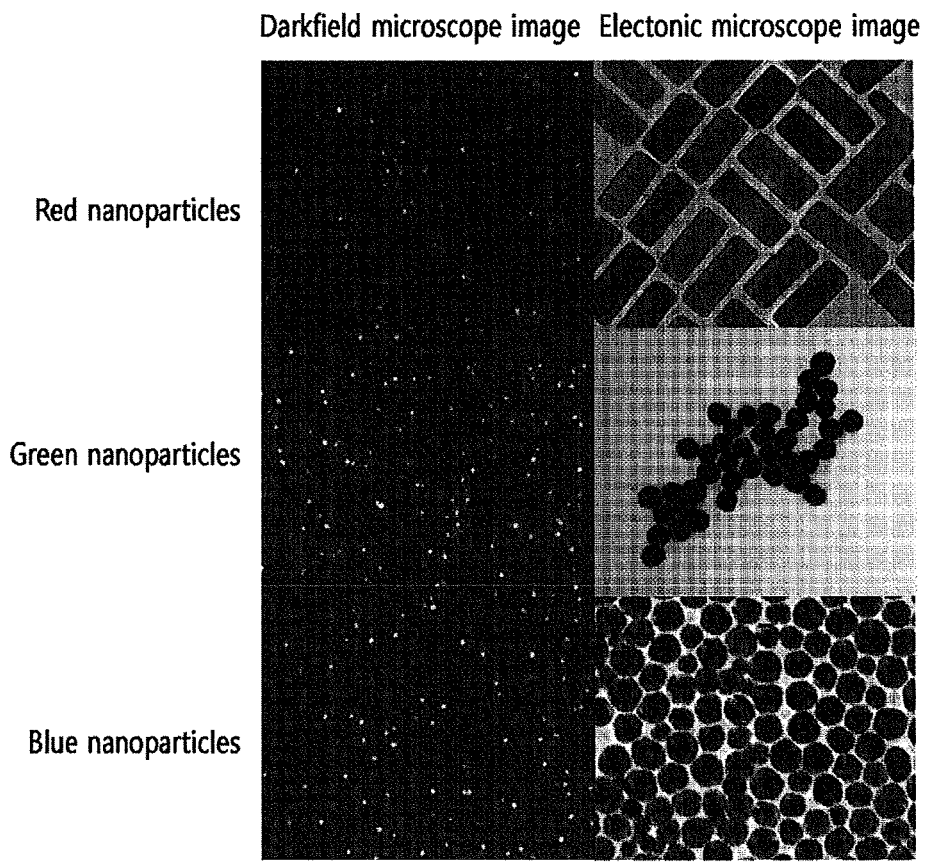
FIG. 26 shows the dark-field microscope and electron microscope images of nanoparticles respectively fabricated in different sizes and different shapes to exhibit different colors, and the absorbing/scattering spectra thereof.
Figure 26:
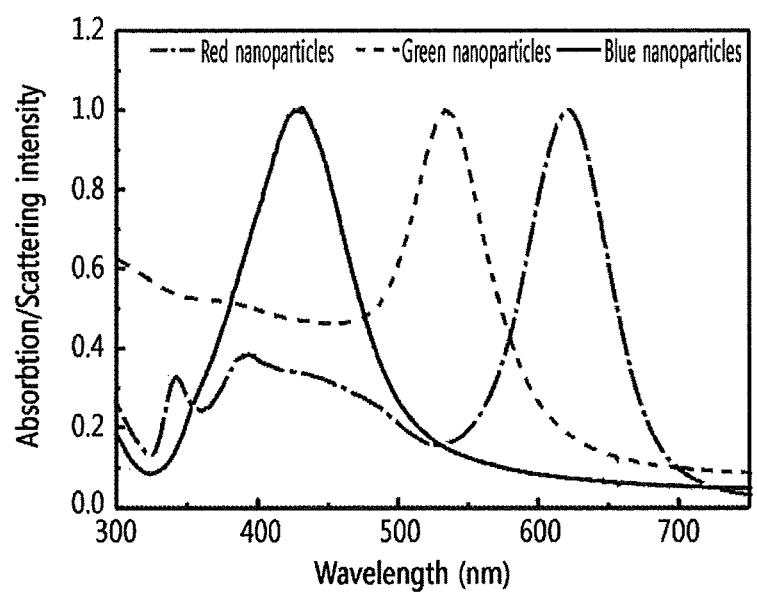

Red nanoparticles were prepared by coating gold nanorods having a size of 15 nm×15 nm×45 nm with a silver shell to a thickness of about 5 nm. As green nanoparticles, spherical gold nanoparticles having a diameter of 50 nm were used. Blue nanoparticles were prepared by coating spherical gold nanoparticles having a diameter of 20 nm with a silver shell to a thickness of about 10 nm. The color and shape of each of the prepared nanoparticles were observed by using a dark-field microscope and an electron microscope, and the results thereof were shown in FIG. 26. Further, the absorbing/scattering spectra of each of the nanoparticles were measured, and the results thereof were also shown in FIGS. 29A and 29B (tight).

Figure 27A:
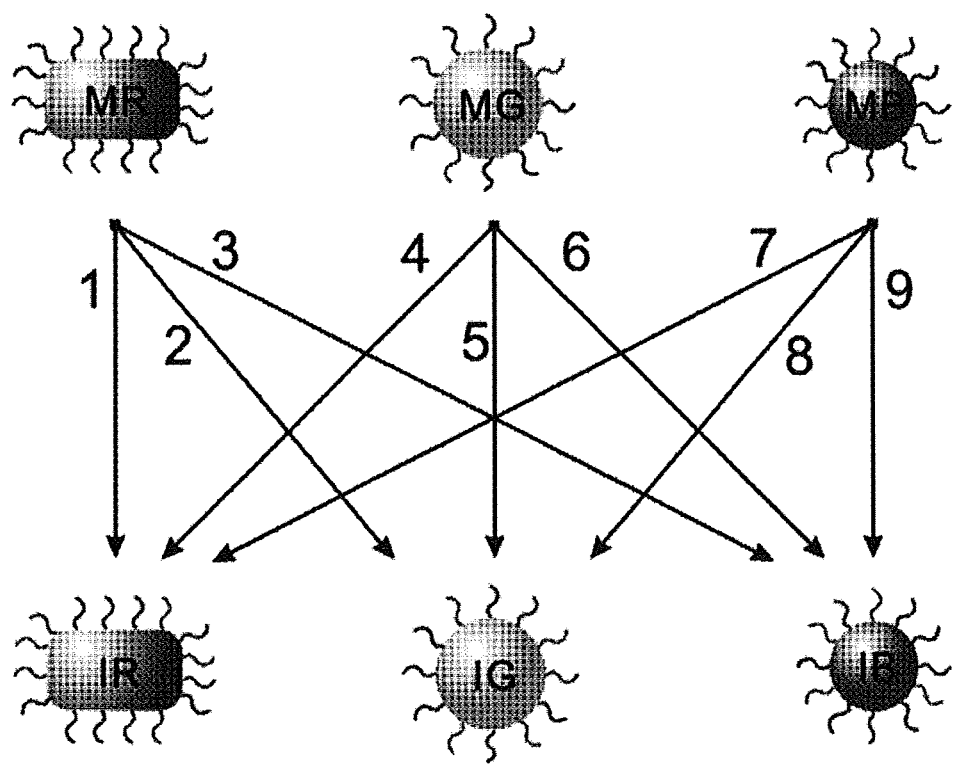
FIG. 27A shows the nine combinations of three-color metal particles fabricated to be respectively fixed on the supported lipid bilayer or moved freely by adjusting valencies.
Figure 27B:
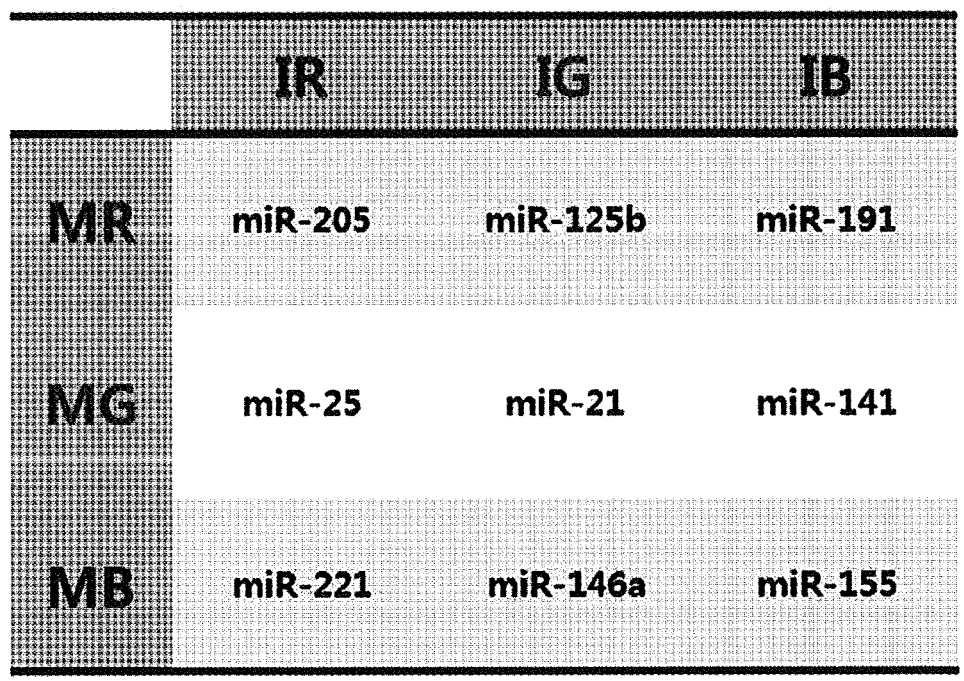
FIG. 27B shows the particle pairs nonspecifically bonded to respective target molecules selected from fixed three-color metal particles and freely movable three-color metal particles for the simultaneous detection of nine types of miRNAs.
Figure 27C:
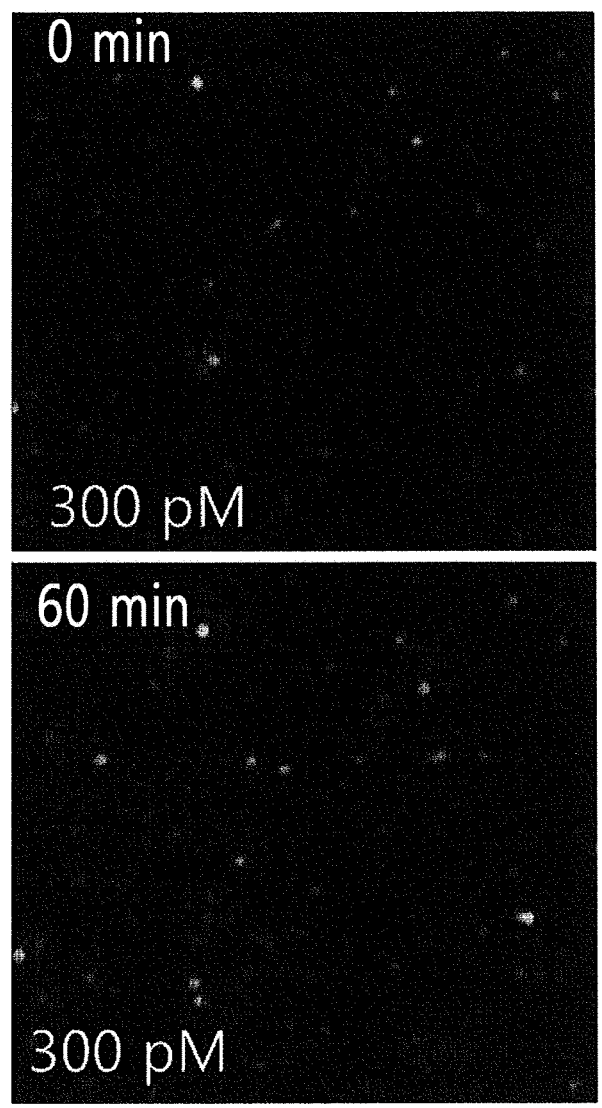
FIG. 27C shows the dark-field microscope images of three-color metal particles at different times (0 min and 60 min), as an example of multiple analysis using the three-color metal particles.
Figure 27D:
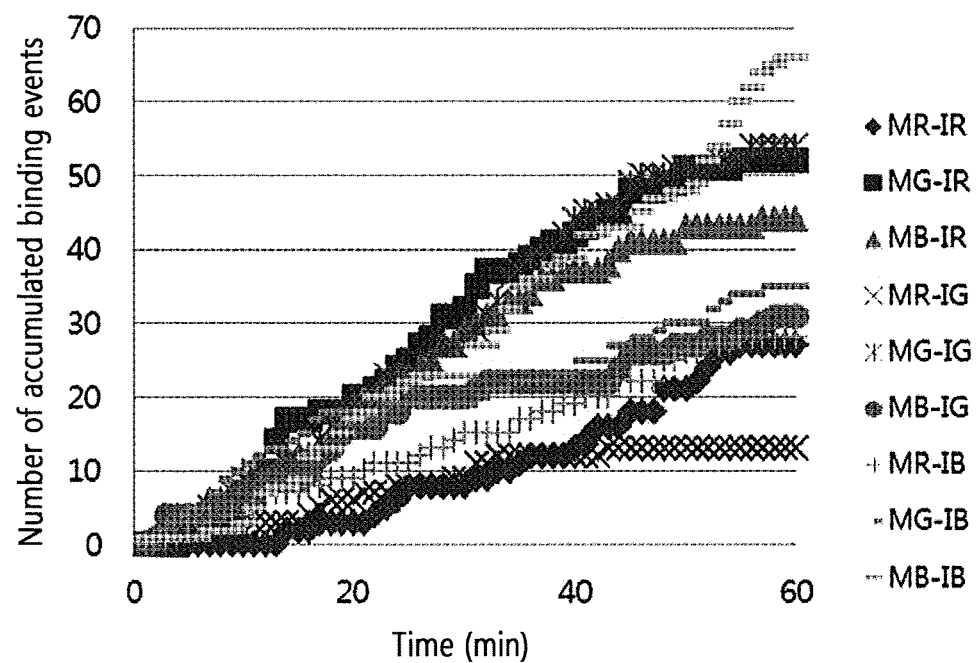
FIG. 27D is a graph showing the cumulative valencies of each target material with respect to time through the simultaneous detection of nine types of miRNAs.
Figure 28B:
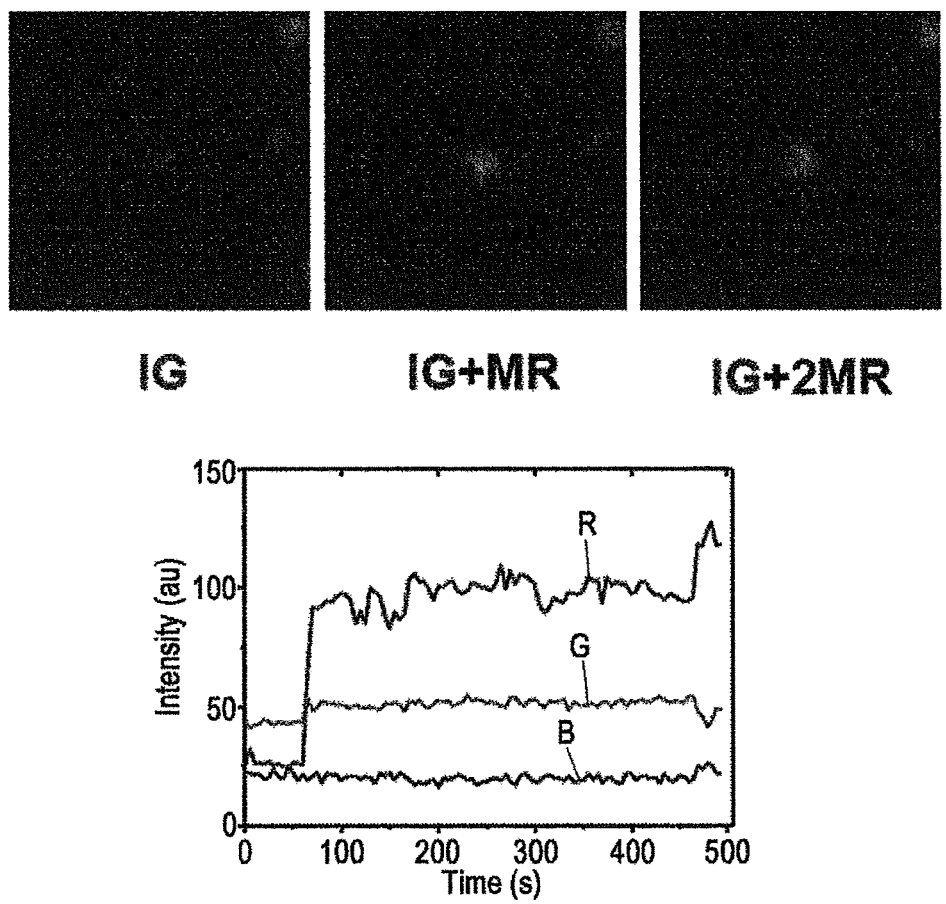
FIG. 28B shows the dark-field microscope images of fixed green nanoparticles and one or more movable red nanoparticles interacting with the fixed green nanoparticles, and the change in intensity of three-color plasmonic scattering spectra at the position of the fixed green nanoparticles with respect to time.
Figure 28C:
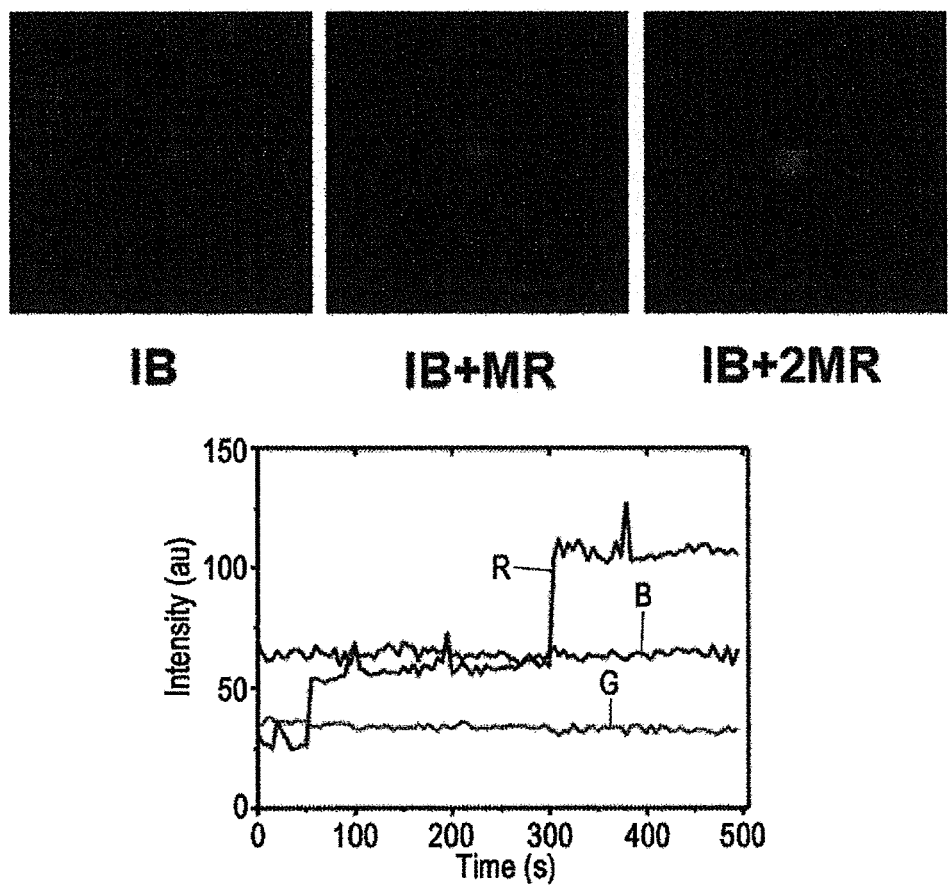
FIG. 28C shows the dark-field microscope images of fixed blue nanoparticles and one or more movable red nanoparticles interacting with the fixed blue nanoparticles, and the change in intensity of three-color plasmonic scattering spectra at the position of the fixed blue nanoparticles with respect to time.
Figure 31:
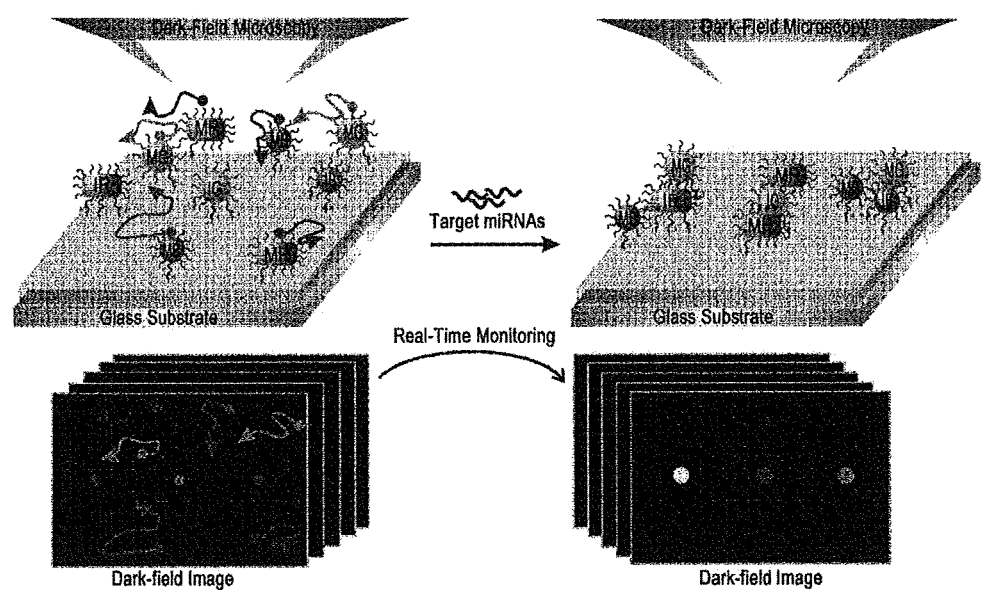
FIG. 31 is a schematic view showing the behaviors of a plurality of particles having different colors (different plasmonic scattering wavelengths) and/or having mobility and the monitoring procedure thereof using a dark-field microscope.

7.2. Multiple Detection of Micro-RNA Through Combination of Three-Color Nanoprobes DNA was introduced into each of the nanoparticles obtained from Example 7.1. in the same manner as in Example 3, and these nanoparticles were functionalized so as to synthesize three-color nanoprobes. The mobility of the three-color nanoprobes was adjusted in the same manner as in Example 4, thereby introducing a total of six types of nanoprobes of I-PNPs (hereinafter, expressed as IR, IG, and IB) and M-PNPs (hereinafter, expressed as MR, MG, and MB) onto SLB. As described in Example 6.1., metal nanoparticles causing plasmonic resonance scattering approach one another according to the hybridization of complementary sequence DNA bonded to the metal nanoparticles to form a cluster of two or more metal nanoparticles, and thus plasmonic scattering intensity as well as plasmonic color is changed (FIGS. 5 to 7). Therefore, when three metal nanoparticles exhibiting different colors are applied, a total of nine types of changes can be expected to be caused by combinations thereof (FIG. 27A), and these changes were confirmed by exemplary embodiments (FIGS. 27B to 27D). Specifically, it was confirmed that the nanoprobes are combined, and are modified with complementary DNA so as to be coupled with nine types of miRNAs (FIG. 27B), and thus each coupling can be analyzed in real time and the nine types of miRNAs can be quantitatively analyzed. Dark-field microscope images measured in the same frame before bonding (0 min) and after reaction for 60 min are shown in FIG. 27C, and the change in cumulative valencies with respect to reaction time is shown in FIG. 27D. The changes in plasmonic scattering spectra by the coupling with the same or different particles in the fixed individual particles (IR, IG, and IB) with respect to time are shown in FIGS. 28 to 30, and the behavior of a plurality of particles having different colors (different plasmonic scattering wavelengths) and mobility and the monitoring procedure thereof using a dark-field microscope are shown in FIG. 31. Therefore, since the multiple detection method of the present invention can simultaneously analyze nine or more types of miRNAs qualitatively and/or quantitatively, this multiple detection method can be used to classify and diagnose six or more types of different cancers.

Figure 32:
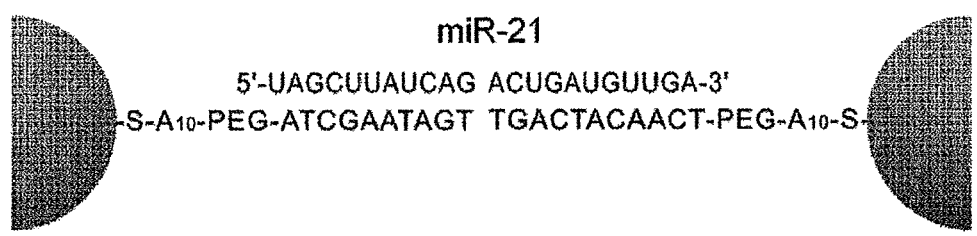
FIG. 32 is a view showing an example (miR-21) (SEQ ID NO: 7) of miRNA detection by complementary sequence (SEQ ID NOS: 8 and 9) recognition.

An example of miRNA detection by complementary sequence recognition is shown in FIG. 32. The sequences of nine types of miRNAs used to confirm the above multiple detection applicability and the DNA sequences introduced into the respective particles in order to detect the miRNA sequences are given in Table 3 below.

TABLE 3

| First target material | miR21 | UAGCUUAUGAGACUGAUGUUGA (SEQ ID NO: 7) |
|---|---|---|
| Molecule $A_1$ | 21_Probe A | TGACTACAACT-PEG-$A_{10}$-3'thiol (SEQ ID NO: 8) |
| Molecule $B_1$ | 21_Probe B | 5'thiol-$A_{10}$-PEG-ATCGAATAGT (SEQ ID NO: 9) |
| Second target material | miR25 | CAUUGCAUUGUCUCGGUCUGA (SEQ ID NO: 10) |
| Molecule $A_2$ | 25_Probe A | CAAGTGCAATG-PEG-$A_{10}$-3'thiol (SEQ ID NO: 11) |
| Molecule $B_2$ | 25_Probe B | 5'thiol-$A_{10}$-PEG-TCAGACCGAGA (SEQ ID NO: 12) |
| Third target material | miR125b | UCCCUGAGACCCUAACUUGUGA (SEQ ID NO: 13) |

TABLE 3-continued

| | | |
|---|---|---|
| Molecule $A_3$ | 125b_Probe A | GGTCTCAGGGA-PEG-$A_{10}$-3'thiol (SEQ ID NO: 14) |
| Molecule $B_3$ | 125b_Probe B | 5'thiol-$A_{10}$-PEG-TCACAAGTTAG (SEQ ID NO: 15) |
| Fourth target material | miR141 | UAACACUGUCUGGUAAAGAUGG (SEQ ID NO: 16) |
| Molecule $A_4$ | 141_Probe A | AGACAGTGTTA-PEG-$A_{10}$-3'thiol (SEQ ID NO: 17) |
| Molecule $B_4$ | 141_Probe B | 5'thiol-$A_{10}$-PEG-CCATCTTTACC (SEQ ID NO: 18) |
| Fifth target material | miR146a | UGAGAACUGAAUUCCAUGGGUU (SEQ ID NO: 19) |
| Molecule $A_5$ | 146a_Probe A | TTCAGTTCTCA-PEG-$A_{10}$-3'thiol (SEQ ID NO: 20) |
| Molecule $B_5$ | 146a_Probe B | 5'thiol-$A_{10}$-PEG-AACCCATGGAA (SEQ ID NO: 21) |
| Sixth target material | miR155 | UUAAUGCUAAUCGGUGAUAGGGG (SEQ ID NO: 22) |
| Molecule $A_6$ | 155_Probe A | ATTAGCATTAA-PEG-$A_{10}$-3'thiol (SEQ ID NO: 23) |
| Molecule $B_6$ | 155_Probe B | 5'thiol-$A_{10}$-PEG-CCCCTATCACG (SEQ ID NO: 24) |
| Seventh target material | miR191 | CAACGGAAUCCCAAAAGCAGCU (SEQ ID NO: 25) |
| Molecule $A_7$ | 191_Probe A | GGATTCCGTTG-PEG-$A_{10}$-3'thiol (SEQ ID NO: 26) |
| Molecule $B_7$ | 191_Probe B | 5'thiol-$A_{10}$-PEG-AGCTGCTTTTG (SEQ ID NO: 27) |
| Eighth target material | miR205 | UCCUUCAUUCCACCGGACUCUG (SEQ ID NO: 28) |
| Molecule $A_8$ | 205_Probe A | GGAATGAAGGA-PEG-$A_{10}$-3'thiol (SEQ ID NO: 29) |
| Molecule $B_8$ | 205_Probe B | 5'thiol-$A_{10}$-PEG-CAGACTCCGGT (SEQ ID NO: 30) |
| Ninth target material | miR221 | AGCUACAUUGUCUGCUGGGUUC (SEQ ID NO: 31) |
| Molecule $A_9$ | 221_Probe A | GACAATGTAGCT-PEG-$A_{10}$-3'thiol (SEQ ID NO: 32) |
| Molecule $B_9$ | 221_Probe B | 5'thiol-$A_{10}$-PEG-GAAACCCAGCA (SEQ ID NO: 33) |

The invention claimed is:

1. An artificial cell membrane, comprising:

a substrate; and a supported lipid bilayer (SLB) disposed on the substrate, wherein the supported lipid bilayer, within which some or all lipids are capable of shifting position, comprises a plurality of molecules of a first lipid bound with a first ligand and a third lipid bound with a plurality of molecules of a third ligand which is the same as or different from the first ligand, a first metal particle comprising a second ligand specifically binding to the first ligand at a density of 100 to 100,000/$\mu m^2$, wherein the first metal particle is bound to at least two of the plurality of molecules of the first lipids through the binding between the first ligand and the second ligand, so as to decrease the mobility of the first metal particle in the supported lipid layer to 0 to 0.5×10$^{-8}$ cm$^2$/s, and a second metal particle comprising a fourth ligand specifically binding to the third ligand, wherein the second metal particle binds to at least one of the plurality of molecules of the third lipids through the interaction between the third ligand and the fourth ligand, and has higher mobility than that of the first metal particle.

2. The artificial cell membrane according to claim 1, wherein the first metal particle is bound to the lipid by antigen-antibody interaction, ligand-receptor interaction, nucleic acid hybridization, chelation, covalent bonding, or electrostatic bonding between the first ligand and the second ligand.

3. The artificial cell membrane according to claim 1, wherein the first metal particle generates plasmonic scattering at an intrinsic wavelength depending on the size or shape thereof.

4. The artificial cell membrane according to claim 1, wherein the first lipid bound with the first ligand is included in an amount of 0.05 to 0.5 mol % with respect to the total amount of lipids in the supported lipid bilayer.

5. The artificial cell membrane according to claim 1, wherein the supported lipid bilayer further comprises a second lipid bound with polyethylene glycol in an amount of 1 to 10 mol % with respect to the total amount of lipids in the supported lipid bilayer.

6. An analysis device for examining the interaction between molecule A and molecule B using an artificial cell membrane, comprising:
the artificial cell membrane of claim 1, molecule A, and molecule B,
wherein the molecule A bound to the surface of the first metal particle in the artificial cell membrane;
wherein the molecule B bound to the surface of the second metal particle in the artificial cell membrane, and
wherein the second metal particle having higher mobility approaches the first metal particle and is then confined to the first metal particle by the interaction between the molecule A and the molecule B.

7. The analysis device according to claim 6, wherein the interaction between the molecule A and the molecule B is selected from the group consisting of antigen-antibody interaction, ligand-receptor interaction, nucleic acid hybridization, chelation, covalent bonding, and electrostatic bonding.

8. The analysis device according to claim 6, wherein the first metal particle is fixed on the supported lipid bilayer, and the second metal particle may carry out 2-dimensional free Brownian motion on the supported lipid bilayer in the absence of the interaction between the molecule A and the molecule B.

9. A method, comprising examining the interaction between the molecule A and the molecule B using the analysis device of claim 6.

10. The method of claim 9, wherein the position of the first metal particle and the change in scattering intensity or wavelength due to the first metal particle are monitored.

11. The method of claim 9, wherein the real-time movement trajectory or speed of the second metal particle, or the change in signal intensity or wavelength due to the second metal particle is monitored.

12. The method of claim 10, wherein the monitoring is accomplished by measuring the plasmonic scattering of the first metal particle.

13. The method of claim 11, wherein the monitoring is accomplished by measuring the plasmonic scattering of the second metal particle.

14. The method of claim 9, wherein the density of particles and the collision frequency between the first metal particles and the second metal particles are increased by additionally applying force in a predetermined direction.

15. An analysis kit for determining the binding between molecule A and molecule B by determining the distance between a first metal particle and a second metal particle from plasmonic scattering signals of the first metal particle bound with the molecule A and the second metal particle bound with the molecule B on an artificial cell membrane, comprising:
an artificial cell membrane comprising a substrate, a supported lipid bilayer which is disposed on the substrate and within which some or all lipids are capable of shifting position, and a plurality of molecules of a first lipid bound with a first ligand and a plurality of molecules of a third lipid bound with a third ligand, which is the same as or different from the first ligand, as a part of the supported lipid bilayer;
a first metal particle comprising a second ligand specifically binding to the first ligand, wherein the first metal particle is able to bind to at least one of the plurality of molecules of the first lipids through the interaction between the first ligand and the second ligand; and
a second metal particle comprising a fourth ligand specifically binding to the third ligand, wherein the second metal particle is able to bind to at least one of the plurality of molecules of the third lipids through the interaction between the third ligand and the fourth ligand, and has higher mobility than that of the first metal particle.

16. A kit for qualitative or quantitative analysis of a target material capable of binding to molecule A and molecule B which is used to determine the binding between the molecule A and the molecule B by determining the distance between a first metal particle and a second metal particle from plasmonic scattering signals of the first metal particle bound with the molecule A and the second metal particle bound with the molecule B on an artificial cell membrane, comprising:
an artificial cell membrane comprising a substrate, a supported lipid bilayer which is disposed on the substrate and within which some or all lipids are capable of shifting position, and a plurality of molecules of a first lipid bound with a first ligand and a plurality of molecules of a third lipid bound with a third ligand, which is the same as or different from the first ligand, as a part of the supported lipid bilayer;
a first metal particle comprising a second ligand specifically binding to the first ligand, wherein the first metal particle is able to bind to at least one of the plurality of molecules of the first lipids through the interaction between the first ligand and the second ligand;

the molecule A which is bound to the surface of the first metal particle and which is specifically bound to a portion of the target material;

a second metal particle comprising a fourth ligand specifically binding to the third ligand, wherein the second metal particle is able to bind to at least one of the plurality of molecules of the third lipids through the interaction between the third ligand and the fourth ligand, and has higher mobility than that of the first metal particle; and the molecule B which is bound to the surface of the second metal particle in the artificial cell membrane and which is specifically bound to another portion of the target material on which the molecule A is not bound.

17. The kit according to claim 16, wherein the first metal particle is fixed on the supported lipid bilayer, and the second metal particle may carry out 2-dimensional free Brownian motion on the supported lipid bilayer in the absence of the interaction through the target material between the molecule A and the molecule B.

18. The kit according to claim 17, wherein the kit measures the changes in the intensity or wavelength of a plasmonic scattering signal or both at the position of the first metal particle where the second metal particle having higher mobility approaches the first metal particle due to the interactions between the molecule A and the target material and between the molecule B and the target material in the presence of the target material.

19. A multiple analysis kit for qualitative or quantitative analysis of target materials in the amount of $i_{max} \times m_{max}$ by the plasmonic scattering measurement, wherein $i_{max}$ and $m_{max}$ are maximum values of the following variables i and m, respectively, and are each independently an integer of 1 or more, but not $i_{max}=m_{max}=1$, comprising:

an artificial cell membrane comprising a substrate, a supported lipid bilayer which is disposed on the substrate and within which some or all lipids are capable of shifting positions, and a plurality of molecules of a lipid $I_i$ bound with a plurality of molecules of a ligand $I_i$ and a lipid $M_m$ bound with a ligand $M_m$, wherein the ligand $I_i$ and the ligand $M_m$ may be the same as or different from each other;

a metal particle $I_i$ comprising a ligand $I'_i$ specifically binding to the ligand $I_i$, wherein the metal particle $I_i$ is bound to at least one of the plurality of molecules of the lipid $I_i$ through the interaction between the ligands $I_i$ and the ligand $I'_i$;

a molecule $A_i$ which is bound to the surface of the metal particle $I_i$ and is specifically bound to a portion of the target material;

a metal particle $M_m$ comprising a ligand $M'_m$ specifically binding to the ligand $M_m$, wherein the metal particle $M_m$ is bound to at least one of the plurality of molecules of the lipid $M_m$ through the interaction between the ligand $M_m$ and the ligand $M'_m$, and has higher mobility compared to that of the metal particle $I_i$; and a molecule $B_m$ which is bound to the surface of the metal particle $M_m$ in the artificial cell membrane and which is specifically bound to another portion of the target material on which the molecule A is not bound, wherein the series of the metal particles $I_i$ have different plasmonic scattering wavelengths from one another, and the series of the metal particles $M_m$ have different plasmonic scattering wavelengths from one another.

* * * * *

UNITED STATES PATENT AND TRADEMARK OFFICE
CERTIFICATE OF CORRECTION

PATENT NO. : 10,509,030 B2
APPLICATION NO. : 15/202928
DATED : December 17, 2019
INVENTOR(S) : Nam et al.

It is certified that error appears in the above-identified patent and that said Letters Patent is hereby corrected as shown below:

Item (72), Inventors:
"Young Kwang Lee, Goyang (KR)" should read --Young Kwang Lee, Goyang-si (KR)--

Claim 1, Column 43, Line 3:
"lipids through the binding between the first ligand and" should read --lipid through the binding between the first ligand and--

Claim 1, Column 43, Line 10:
"molecules of the third lipids through the interaction" should read --molecules of the third lipid through the interaction--

Claim 15, Column 33, Line 37:
"molecules of the first lipids through the interaction" should read --molecules of the first lipid through the interaction--

Claim 15, Column 44, Line 42:
"plurality of molecules of the third lipids through the" should read --plurality of molecules of the third lipid through the--

Claim 16, Column 44, Line 66:
"molecules of the first lipids through the interaction" should read --molecules of the first lipid through the interaction--

Claim 16, Column 45, Line 7:
"plurality of molecules of the third lipids through the" should read --plurality of molecules of the third lipid through the--

Signed and Sealed this
First Day of September, 2020

Andrei Iancu
*Director of the United States Patent and Trademark Office*

SEQUENCE LISTING

<160> NUMBER OF SEQ ID NOS: 33

<210> SEQ ID NO 1
<211> LENGTH: 25
<212> TYPE: DNA
<213> ORGANISM: Artificial Sequence
<220> FEATURE:
<223> OTHER INFORMATION: Target capture sequence for I-PNP

<400> SEQUENCE: 1
ctttgagcac atccttatca atatt                                    25

```
<210> SEQ ID NO 2
<211> LENGTH: 34
<212> TYPE: DNA
<213> ORGANISM: Artificial Sequence
<220> FEATURE:
<223> OTHER INFORMATION: SLB tethering sequence for I-PNP

<400> SEQUENCE: 2
ctttgagcac tgttagcgtg tgtggaattt taat                                34

<210> SEQ ID NO 3
<211> LENGTH: 25
<212> TYPE: DNA
<213> ORGANISM: Artificial Sequence
<220> FEATURE:
<223> OTHER INFORMATION: Target capture sequence for M-PNP

<400> SEQUENCE: 3
taacaataat ccctccacga gtttc                                         25

<210> SEQ ID NO 4
<211> LENGTH: 34
<212> TYPE: DNA
<213> ORGANISM: Artificial Sequence
<220> FEATURE:
<223> OTHER INFORMATION: SLB tethering sequence for M-PNP

<400> SEQUENCE: 4
taattttaag gtgtgtgcga ttgtcacgag tttc                               34

<210> SEQ ID NO 5
<211> LENGTH: 30
<212> TYPE: DNA
<213> ORGANISM: Artificial Sequence
<220> FEATURE:
<223> OTHER INFORMATION: Target sequence

<400> SEQUENCE: 5
gagggattat tgttaaatat tgataaggat                                    30

<210> SEQ ID NO 6
<211> LENGTH: 30
<212> TYPE: DNA
<213> ORGANISM: Artificial Sequence
<220> FEATURE:
<223> OTHER INFORMATION: Non-complementary DNS sequence

<400> SEQUENCE: 6
ctgattacta ttgcatcttc cgttacaact                                    30

<210> SEQ ID NO 7
<211> LENGTH: 22
<212> TYPE: RNA
<213> ORGANISM: Artificial Sequence
<220> FEATURE:
<223> OTHER INFORMATION: miR21 sequence

<400> SEQUENCE: 7
uagcuuauga gacugauguu ga                                            22

<210> SEQ ID NO 8
<211> LENGTH: 11
<212> TYPE: DNA
<213> ORGANISM: Artificial Sequence
<220> FEATURE:
<223> OTHER INFORMATION: 21_Probe A
```

```
<400> SEQUENCE: 8
tgactacaac t                                                    11

<210> SEQ ID NO 9
<211> LENGTH: 10
<212> TYPE: DNA
<213> ORGANISM: Artificial Sequence
<220> FEATURE:
<223> OTHER INFORMATION: 21_Probe B

<400> SEQUENCE: 9
atcgaatagt                                                      10

<210> SEQ ID NO 10
<211> LENGTH: 21
<212> TYPE: RNA
<213> ORGANISM: Artificial Sequence
<220> FEATURE:
<223> OTHER INFORMATION: miR25 sequence

<400> SEQUENCE: 10
cauugcauug ucucggucug a                                         21

<210> SEQ ID NO 11
<211> LENGTH: 11
<212> TYPE: DNA
<213> ORGANISM: Artificial Sequence
<220> FEATURE:
<223> OTHER INFORMATION: 25_Probe A

<400> SEQUENCE: 11
caagtgcaat g                                                    11

<210> SEQ ID NO 12
<211> LENGTH: 11
<212> TYPE: DNA
<213> ORGANISM: Artificial Sequence
<220> FEATURE:
<223> OTHER INFORMATION: 25_Probe B

<400> SEQUENCE: 12
tcagaccgag a                                                    11

<210> SEQ ID NO 13
<211> LENGTH: 22
<212> TYPE: RNA
<213> ORGANISM: Artificial Sequence
<220> FEATURE:
<223> OTHER INFORMATION: miR125b sequence

<400> SEQUENCE: 13
ucccugagac ccuaacuugu ga                                        22

<210> SEQ ID NO 14
<211> LENGTH: 11
<212> TYPE: DNA
<213> ORGANISM: Artificial Sequence
<220> FEATURE:
<223> OTHER INFORMATION: 125b_Probe A

<400> SEQUENCE: 14
ggtctcaggg a                                                    11
```

<210> SEQ ID NO 15
<211> LENGTH: 11
<212> TYPE: DNA
<213> ORGANISM: Artificial Sequence
<220> FEATURE:
<223> OTHER INFORMATION: 125b_Probe B

<400> SEQUENCE: 15
tcacaagtta g                                                          11

<210> SEQ ID NO 16
<211> LENGTH: 22
<212> TYPE: RNA
<213> ORGANISM: Artificial Sequence
<220> FEATURE:
<223> OTHER INFORMATION: miR141 sequence

<400> SEQUENCE: 16
uaacacuguc ugguaaagau gg                                              22

<210> SEQ ID NO 17
<211> LENGTH: 11
<212> TYPE: DNA
<213> ORGANISM: Artificial Sequence
<220> FEATURE:
<223> OTHER INFORMATION: 141_Probe A

<400> SEQUENCE: 17
agacagtgtt a                                                          11

<210> SEQ ID NO 18
<211> LENGTH: 11
<212> TYPE: DNA
<213> ORGANISM: Artificial Sequence
<220> FEATURE:
<223> OTHER INFORMATION: 141_Probe B

<400> SEQUENCE: 18
ccatctttac c                                                          11

<210> SEQ ID NO 19
<211> LENGTH: 22
<212> TYPE: RNA
<213> ORGANISM: Artificial Sequence
<220> FEATURE:
<223> OTHER INFORMATION: miR146a sequence

<400> SEQUENCE: 19
ugagaacuga auccaugggu uu                                              22

<210> SEQ ID NO 20
<211> LENGTH: 11
<212> TYPE: DNA
<213> ORGANISM: Artificial Sequence
<220> FEATURE:
<223> OTHER INFORMATION: 146a_Probe A

<400> SEQUENCE: 20
ttcagttctc a                                                          11

<210> SEQ ID NO 21
<211> LENGTH: 11
<212> TYPE: DNA
<213> ORGANISM: Artificial Sequence
<220> FEATURE:
<223> OTHER INFORMATION: 146a_Probe B

<400> SEQUENCE: 21
aacccatgga a                                                            11

<210> SEQ ID NO 22
<211> LENGTH: 23
<212> TYPE: RNA
<213> ORGANISM: Artificial Sequence
<220> FEATURE:
<223> OTHER INFORMATION: miR155 sequence

<400> SEQUENCE: 22
uuaaugcuaa ucggugauag ggg                                               23

<210> SEQ ID NO 23
<211> LENGTH: 11
<212> TYPE: DNA
<213> ORGANISM: Artificial Sequence
<220> FEATURE:
<223> OTHER INFORMATION: 155_Probe A

<400> SEQUENCE: 23
attagcatta a                                                            11

<210> SEQ ID NO 24
<211> LENGTH: 11
<212> TYPE: DNA
<213> ORGANISM: Artificial Sequence
<220> FEATURE:
<223> OTHER INFORMATION: 155_Probe B

<400> SEQUENCE: 24
cccctatcac g                                                            11

<210> SEQ ID NO 25
<211> LENGTH: 22
<212> TYPE: RNA
<213> ORGANISM: Artificial Sequence
<220> FEATURE:
<223> OTHER INFORMATION: miR191 sequence

<400> SEQUENCE: 25
caacggaauc ccaaaagcag cu                                                22

<210> SEQ ID NO 26
<211> LENGTH: 11
<212> TYPE: DNA
<213> ORGANISM: Artificial Sequence
<220> FEATURE:
<223> OTHER INFORMATION: 191_Probe A

<400> SEQUENCE: 26
ggattccgtt g                                                            11

<210> SEQ ID NO 27
<211> LENGTH: 11
<212> TYPE: DNA
<213> ORGANISM: Artificial Sequence
<220> FEATURE:
<223> OTHER INFORMATION: 191_Probe B

<400> SEQUENCE: 27
agctgctttt g                                                            11

```
<210> SEQ ID NO 28
<211> LENGTH: 22
<212> TYPE: RNA
<213> ORGANISM: Artificial Sequence
<220> FEATURE:
<223> OTHER INFORMATION: miR205 sequence

<400> SEQUENCE: 28
uccuucauuc caccggacuc ug                                              22

<210> SEQ ID NO 29
<211> LENGTH: 11
<212> TYPE: DNA
<213> ORGANISM: Artificial Sequence
<220> FEATURE:
<223> OTHER INFORMATION: 205_Probe A

<400> SEQUENCE: 29
ggaatgaagg a                                                          11

<210> SEQ ID NO 30
<211> LENGTH: 11
<212> TYPE: DNA
<213> ORGANISM: Artificial Sequence
<220> FEATURE:
<223> OTHER INFORMATION: 205_Probe B

<400> SEQUENCE: 30
cagactccgg t                                                          11

<210> SEQ ID NO 31
<211> LENGTH: 22
<212> TYPE: RNA
<213> ORGANISM: Artificial Sequence
<220> FEATURE:
<223> OTHER INFORMATION: miR221 sequence

<400> SEQUENCE: 31
agcuacauug ucugcugggu uc                                              22

<210> SEQ ID NO 32
<211> LENGTH: 12
<212> TYPE: DNA
<213> ORGANISM: Artificial Sequence
<220> FEATURE:
<223> OTHER INFORMATION: 221_Probe A

<400> SEQUENCE: 32
gacaatgtag ct                                                         12

<210> SEQ ID NO 33
<211> LENGTH: 11
<212> TYPE: DNA
<213> ORGANISM: Artificial Sequence
<220> FEATURE:
<223> OTHER INFORMATION: 221_Probe B

<400> SEQUENCE: 33
gaaacccagc a                                                          11
```